(12) United States Patent
Dunn-Coleman et al.

(10) Patent No.: US 7,510,831 B2
(45) Date of Patent: Mar. 31, 2009

(54) *TRICHODERMA REESEI* PHYTASE ENZYMES, NUCLEIC ACIDS ENCODING SUCH PHYTASE ENZYMES, VECTORS AND HOST CELLS INCORPORATING SAME AND METHODS OF MAKING AND USING SAME

(75) Inventors: Nigel Dunn-Coleman, Los Gatos, CA (US); Frits Goedegebuur, Vlaardingen (NL); Michael Ward, San Francisco, CA (US)

(73) Assignee: Genencor International, Inc., Palo Alto, CA (US)

( * ) Notice: Subject to any disclaimer, the term of this patent is extended or adjusted under 35 U.S.C. 154(b) by 397 days.

(21) Appl. No.: 10/492,783

(22) PCT Filed: Oct. 9, 2002

(86) PCT No.: PCT/US02/32379

§ 371 (c)(1),
(2), (4) Date: Apr. 14, 2004

(87) PCT Pub. No.: WO03/038035

PCT Pub. Date: May 8, 2003

(65) Prior Publication Data

US 2005/0130148 A1 Jun. 16, 2005

Related U.S. Application Data

(60) Provisional application No. 60/339,475, filed on Oct. 26, 2001.

(51) Int. Cl.
*C12Q 1/68* (2006.01)
*C12P 21/00* (2006.01)
*C12N 9/00* (2006.01)
*C07K 14/00* (2006.01)
*C12N 15/63* (2006.01)

(52) U.S. Cl. .......................... 435/6; 435/71.1; 435/183; 530/350

(58) Field of Classification Search ........................ None
See application file for complete search history.

(56) References Cited

U.S. PATENT DOCUMENTS

| | | | |
|---|---|---|---|
| 4,469,863 A | 9/1984 | Ts'o et al. | |
| 4,683,202 A | 7/1987 | Mullis | |
| 5,034,506 A | 7/1991 | Summerton et al. | |
| 5,216,141 A | 6/1993 | Benner | |
| 5,235,033 A | 8/1993 | Summerton et al. | |
| 5,268,526 A | 12/1993 | Hershey et al. | |
| 5,386,023 A | 1/1995 | Sanghvi et al. | |
| 5,510,471 A | 4/1996 | Lebrun et al. | |
| 5,538,880 A | 7/1996 | Lundquist et al. | |
| 5,571,706 A | 11/1996 | Baker et al. | |
| 5,589,615 A | 12/1996 | De Clercq et al. | |
| 5,597,945 A | 1/1997 | Jaynes et al. | |
| 5,602,240 A | 2/1997 | De Mesmaeker et al. | |
| 5,610,049 A | 3/1997 | Clark | |
| 5,637,684 A | 6/1997 | Cook et al. | |
| 5,644,048 A | 7/1997 | Yau | |
| 5,677,175 A | 10/1997 | Hodges et al. | |
| 5,750,386 A | 5/1998 | Conkling et al. | |
| 5,750,871 A | 5/1998 | Moloney et al. | |
| 5,773,269 A | 6/1998 | Somers et al. | |
| 5,780,292 A * | 7/1998 | Nevalainen et al. | 435/256.8 |
| 5,780,708 A | 7/1998 | Lundquist et al. | |
| 5,907,080 A | 5/1999 | Karatzas et al. | |
| 5,942,435 A | 8/1999 | Wheeler | |
| 5,998,697 A | 12/1999 | Devlin | |
| 6,066,725 A | 5/2000 | DeBoer et al. | |
| 6,262,336 B1 | 7/2001 | Lubon et al. | |
| 6,268,545 B1 | 7/2001 | Houdebine et al. | |
| 6,271,436 B1 | 8/2001 | Piedrahita et al. | |
| 6,475,762 B1 * | 11/2002 | Stafford et al. | 435/196 |
| 6,514,495 B1 * | 2/2003 | Svendsen et al. | 424/94.6 |

FOREIGN PATENT DOCUMENTS

| | | | |
|---|---|---|---|
| EP | 0684313 A2 | 11/1995 | |
| EP | 0420358 B1 | 5/1999 | |

OTHER PUBLICATIONS

Mullaney et al.. The term phytase comprises several different classes of enzymes. Biochem. and Biophys. Res. Comm. 312: 179-184. 2003.*

Henikoff, Steven et al., << Amino acid substitution matrices from protein blocks, >> Proc. Natl. Acad. Sci., USA, vol. 89, pp. 10915-10919, 1992.

Higgins, Desmond G. et al., << Clustal V : improved software for multiple sequence alignment, >> Comput. Appl. Biosci., vol. 8, No. 2, pp. 189-191, 1992.

Hopp, Thomas P. et al., << A Short Polypeptide Marker Sequence Useful for Recombinant Protein Identification and Purification, >> Bio/Technology, vol. 6, pp. 1204-1210, 1988.

(Continued)

*Primary Examiner*—David Guzo
*Assistant Examiner*—Michele K Joike
(74) *Attorney, Agent, or Firm*—Danisco US Inc., Genencor Division

(57) ABSTRACT

A novel DNA is provided which encodes an enzyme having phytase activity isolated from *Trichoderma*. Also provided for is a method of isolating DNA encoding an enzyme having phytase activity from organisms which possess such DNA, transformation of the DNA into a suitable host organism, expression of the transformed DNA and the use of the expressed phytase protein in feed as a supplement.

12 Claims, 6 Drawing Sheets

OTHER PUBLICATIONS

Jenkins, Gareth N. et al., << The Biosynthesis of Carbocyclic Nucleosides, >> Chemical Society Reviews, pp. 169-176, 1995.

Jung, Paul M. et al., << Hybridization of Alternating Cationic/Anionic Oligonucleotides to RNA Segments' >> Nucleosides & Nucleotides, vol. 13, Nos. 6 & 7, pp. 1597-1605, 1994.

Karlin, Samuel et al., << Applications and statistics for multiple high-scoring segments in molecular sequences, >> Proc. Natl. Acad. Sci., USA, vol. 90, pp. 5873-5877, 1993.

Kerovuo, Janne et al., << Isolation, Characterization, Molecular Gene Cloning, and Sequencing of a Novel Phytase from *Bacillus subtilis*, >> Applied and Environmental Microbiology, vol. 64, No. 6, pp. 2079-2085, 1998.

Kornegay, E. T. et al., << Response of broilers to graded levels of Microbial phytase added to maize-soyabean-meal-based diets containing three levels of non-phytate phosphorus, >> British Journal of Nutrition, vol. 75, pp. 839-852, 1996.

Letsinger, Robert L. et al., << Cationic Oligonucleotides, >> J. Am. Chem. Soc. vol. 110, pp. 4470-4471, 1988.

Letsinger, Robert L. et al., << Effects of pendant groups at phosphorus on binding properties of d-ApA analogues, >> Nucleic Acids Research, vol. 14, No. 8, pp. 3487-3499, 1986.

Letsinger, Robert L. et al., << Phosphoramidate Analogs of Oligonucleotides, >> J. Org. Chem., vol. 35, No. 11, pp. 3800-3803, 1970.

Leung, David W.. et al., << A Method for Random Mutagenesis of a Defined DNA Segment Using a Modified Polymerase Chain Reaction, >> Technique—A Journal of Methods in Cell and Molecular Biology, vol. 1, No. 1, pp. 11-15, 1989.

Lutz-Greyermuth, Carol et al., << Quantitative determination that one of two potential RNA-binding domains of the A protein component of the U1 small nuclear ribonucleoprotein complex binds with high affinity to stem-loop II of U1 RNA, >> Proc. Natl. Acad. Sci., USA, vol. 87, pp. 6393-6397, 1990.

Madden, Thomas L. et al., << Applications of Network BLAST Server, *Methods in Enzymology*, Academic Press, vol. 266, pp. 131-141, 1996.

Al-Batshan, H.A. et al., <<Duodenal Calcium Uptake, Femur Ash, and Eggshell Quality Decline with Age and Increase Following Molt, >>, Poultry Science, vol. 73, No. 10, pp. 1590-1596, 1994.

Altschul, Stephen F. et al., << Basic Local Alignment Search Tool, >> J. Mol. Biol., vol. 215, pp. 403-410, 1990.

Altschul, Stephen F. et al., << Gapped BLAST and PSI-BLAST : a new generation of protein database search programs, >> Nucleic Acids Research, vol. 25, No. 17, pp. 3389-3402, 1997.

Aplin, John D. et al., << Preparation, Properties, and Applications of Carbohydrate Conjugates of Proteins and Lipids, >> Crit. Rev. Biochem., pp. 259-306, May 1981.

Beaton, Graham et al., << Synthesis of oligonucleotide phosphorodithioates, >> *Oligonucleotides and Analogues, A Practical Approach*, F. Eckstein, ed., Oxford University Press, pp. 109-134, 1991.

Beaucage, Serge et al., << The Functionalization of Oligonucleotides via Phosphoramidite Derivatives, >> Tetrahedron Report No. 329, Tetrahedron, vol. 49, No. 10, pp. 1925-1963, 1993.

Bennett & Lasure, *More Gene Manipulations in Fungi*, Academic Press, San Diego, pp. 70-76, 1991.

Benton, W. et al., << Screening Agt Recombinant Clones by Hybridization to Single Plaques in situ, >> Science, vol. 196, pp. 180-182, 1977.

Birnboim, H.C. et al., << A rapid alkaline extraction for screening recombinant plasmid DNA, >> Nucleic Acids Research, vol. 7, No. 6, pp. 1513-1523, 1979.

Botstein, David et al., << Strategies and Applications of in Vitro Mutagenesis, >> Science, vol. 229, No. 4719, pp. 1193-1201, Sep. 20, 1985.

Brill, Wolfgang K. D., et al., <<Synthesis of Oligodeoxynucleoside Phosphorodithioates via Thioamidtes, >> J. A. Chem. Soc., vol. 111, pp. 2321-2322, 1989.

Brisson, N. et al., << Expression of a bacterial gene in plants by using a viral vector, << Nature, vol. 310, pp. 511-514, Aug. 9, 1984.

Broglle, Richard et al., << Light-Regulated Expression of a Pea Ribulose-1,5-Bisphosphate Carboxylase Small Subunit Gene in Transformed Plant Cells, >> Science, vol. 224, pp. 838-843, 1984.

Cadwell, R.C., et al., << Randomization of Genes by PCR Mutagenesis, >> PCR Methods and Applications, vol. 2, pp. 28-33, 1992.

Carlsson, Christina et al., << Screening for genetic mutations, >> Nature, vol. 380, pp. 207, Mar. 21, 1996.

Clunies, M. et al., << Effect of dietary calcium level on plasma proteins and calcium flux occurring during a 24 h ovulatory cycle, >> Canadian Journal of Animal Science, vol. 75, No. 3, pp. 439-444, 1995.

Coruzzi, Gloria et al., << Tissue-specific and light-regulated expression of a pea nuclear gene encoding the small subunit of ribulose-1,5-biphosphate carboxylase, >> The EMBO Journal, vol. 3, No. 8, pp. 1671-1679, 1984.

Creighton, T. E., *Proteins : Structure and Molecular Principles*, W. H. Freeman and Company, San Francisco, pp. 79-86, 1983.

Cromwell, G.L. et al., << Efficacy of Phytase in Improving the Bioavailability of Phosphorus in Soybean Meal and Corn-Soybean Meal Diets for Pigs, >> J. Anim. Sci., vol. 71, pp. 1831-1840, 1993.

Damron, B. L. et al., << Calcium Supplementation of Hen Drinking Water, >> Poultry Science, vol. 74, No. 5, pp. 784-787, 1995.

Dayhoff, M. O. et al., << A Model of Evolutionary Change in Proteins, >> *Atlas of Protein Sequence and Structure*, vol. 5, suppl. 3, Dayhoff, M. O. ed., Natl. Biomed. Res. Foundation, Washington, D.C., vol. 5, suppl. 3, pp. 345-352, 1978.

De Groot, Marcel et al., << Agrobacterium tumefaciens-mediated transformation of filamentous fungi, >> Nature Biotechnology, vol. 16, pp. 839-842, 1998.

De Mesmaeker, Alain et al., Bioorganic & Medicinal Chemistry Letters, vol. 4, No. 3, pp. 395-398, 1994.

Dempcy, Robert O. et al., << Synthesis of a thymidyl pentamer of deoxyribonucleic guanidine and binding studies with DNA homopolynucleotides, >> Proc. Natl. Acad. Sci., USA, vol. 92, pp. 6097-6101, 1995.

Deutscher, Murray P., << Rethinking Your Purification Procedure, >> *Methods in Enzymology*, Academic Press, vol. 182, pp. 779-780, 1990.

Eckert, Kristin A. et al., << DNA Polymerase Fidelity and the Polymerase Chain Reaction, >> PCR Methods and Applications, Cold Spring Harbor Laboratory Press, pp. 17-24-, 1991.

Edge, Albert S. et al., << Deglycosylation of Glycoproteins by Trifluoromethanesulfonic Acid, >> Analytical Biochemistry, vol. 118, pp. 131-137, 1981.

Egholm, Michael et al., << Peptide Nucleic Acids (PNA). Oligonucleotide Analogues with an Achiral Peptide Backbone, >> J. A. Chem. Soc., vol. 114, pp. 1895-1897, 1992.

Egholm, Michael et al., << PNA hybridizes to complementary oligonucleotides obeying the Watson-Crick hydrogen-bonding rules, >> Nature, vol. 365, pp. 566-568, Oct. 7, 1993.

Ehrlich, Kenneth C. et al., << Identification and cloning of a second phytase gene (*phyB*), from *Aspergillus niger* (*ficuum*) >> Biochemical and Biophysical Research Communications, vol. 195, No. 1, pp. 53-57, Aug. 31, 1993.

Elander, R. P., Microbial Screening, Selection and Strain Improvement, << *Basic Biotechnology*, Academic Press, Harcourt, Brace Jovanovich, Pub., Bulock, John et al. Ed., New York, pp. 217-251, 1987.

Evan, Gerard I. et al., << Isolation of Monoclonal Antibodies Specific for Human c-myc Proto-Oncogene Product, >> Molecular and Cellular Biology, vol. 5, No. 12, pp. 3610-3616, Dec. 1985.

Field, Jeffrey et al., << Purification of a RAS-Reponsive Adenylyl Cyclase Complex from *Saccharomyces cerevisiae* by Use of an Epitope Addition Method, >> Molecular and Cellular Biology, vol. 8, No. 5, pp. 2159-2165, May 1988.

Finkelstein, David B. et al., << Biotechnology of Filamentous Fungi, Technology and Products, Butterworth-Heinemann, David Finkelstein, ed., pp. 113-156, 1992.

Fiske, Cyrus H. et al., << The Colorimetric Determination of Phosphorus, >> The Journal of Biological Chemistry, vol. 66, No. 2, pp. 375-392, 1925.

Fungaro, Maria H. P. et al., << Transformation of *Aspergillus nidulans* by microprojectile bombardment on intact conidia, >> FEMS Microbiology Letters, vol. 125, pp. 293-298. 1995.

Gao, Xiaolian et al., << Unusual conformation of a 3'-thioformacetal linkage in a DNA duplex, >> Journal of Biomolecular NMR, vol. 4, pp. 17-34, 1994.

Gelvin, Stanton B. et al., << vir Genes Influence Conjugal Transfer of the Ti Plasmid of *Agrobacterium tumefaciens*, >> Journal of Bacteriology, vol. 172, No. 3, pp. 1600-1608, 1990.

Gish, Warren et al., << Identification of protein coding regions by database similarity search, >> Nature Genetics, vol. 3, pp. 266-272, 1993.

Grunstein, Michael et al., << Colony hybridization : A method for the isolation of cloned dans that contain a specific gene, >> Proc. Nat. Acad. Sci, USA, vol. 72, No. 10, pp. 3961-3965, 1975.

Mag, Matthias et al., << Synthesis and selective cleavage of an oligodeoxynucleotide containing a bridged internucleotide 5'-phosphorothioate linkage, >> Nucleic Acids Research, vol. 19, No. 7, pp. 1437-1441, 1991.

Martin, George et al., << GAP Domains Responsible for Ras p21-Dependent Inhibition of Muscarinic Atrial $K^+$ Channel Currents, >> Science, vol. 255, pp. 192-194, 1992.

Meier, Chris et al., << Peptide Nucleic Acids (PNAs)—Unusual Properties of Nonionic Oligonucleotide Analogues, >> Angew. Chem. Into. Ed. Engl., vol. 31, No. 8, pp. 1008-1010, 1992.

The Merck Veterinary Manual, Merck & Co., Inc., Rahway, N.J., 7th ed., p. 1268-1269, 1991.

Mitchell, David B. et al., << The phytase subfamily of histidine acid phosphatases : isolation of genes for two novel phytases from the fungi *Aspergillus terreus* and *Myceliophthora thermophila*, >> Microbiology, vol. 143, pp. 245-252, 1997.

Murray, Lynn, McGraw Hill Yearbook of Science and Technology, McGraw Hill, New York, NY, pp. 191-196, 1992.

Myers, Richard M. et al., << A General Method for Saturation Mutagenesis of Cloned DNA Fragments, >> Science, vol. 229, pp. 242-247, 1985.

Needleman, Saul B. et al., << A General Method Applicable to the Search for Similarities in the Amino Acid Sequence of Two Proteins, >> J. Mol. Biol. vol. 48, pp. 443-543, 1970.

Oakley, Berl R. et al., <<Cloning, mapping and molecular analysis of the pyrG (orotidine-5'-phosphate decarboxylase) gene of *Aspergillus nidulans*, >> Gene, vol. 61, pp. 385-399, 1987.

Paborsky, Lisa R. et al., <<Mammalian cell transient expression of tissue factor for the production of antigen, >> Protein Engineering, vol. 3, No. 6, pp. 547-553, 1990.

Pasamontes, Luis et al., << Cloning of the phytases from *Emericella nidulans* and the thermophilic fungus *Talaromyces thermophilus*, >> Biochimeca et Biophysica Acta 1353, pp. 217-223, 1997.

Pasamontes, Luis et al., << Gene Cloning, Purification, and Characterization of a Heat-Stable Phytase from the Fungus *Aspergillus fumigatus*, <<Applied and Environmental Microbiology, vol. 63, No. 5, pp. 1696-1700, 1997.

Pauwels, R. et al., << Biological Activity of New 2-5A Analogues, Chemica Scripta, vol. 26, pp. 141-145, 1986.

Pearson, William R. et al., << Improved tools for biological sequence comparison, >> Proc. Natl. Acad. Sci. USA, vol. 85, pp. 2444-2448, 1988.

Piddington, C.S. et al., << The cloning and sequencing of the genes encoding phytase (phy) and pH 2.5-optimum acid phosphatase (aph) from *Aspergillus niger* var. *awamori*, >> Gene, vol. 133, pp. 55-62, 1993.

Powar, V. K. et al., << Purification and Properties of Phytate-Specific Phosphatase from *Bacillus subtilis*, >> Journal of Bacteriology, vol. 151, No. 3, pp. 1102-1108, 1982.

Rawls, Rebecca L., << Optimistic about Antisense, >> C&E News, pp. 35-39, Jun. 2, 1997.

Rogers, Stephen G. et al., << Gene Transfer in Plants : Production of Transformed Plants Using Ti Plasmid Vectors, >>Methods for Plants Molecular Biology, Academic Press, New York, NY pp. 421-463, 1988.

Roland, D. A., Sr. et al., Influence of Calcium and Environmental Temperature on Performance of First-Cycle (Phase 1) Commerical Leghorns, >> Poultry Science, vol. 75, No. 1, pp. 62-68, 1996.

Sanchez, Olivia et al., << Efficient Transformation of *Aspergillus nidulans* by Electroporation of Germinated Conidia, >> Fungal Genetics Newsletter, vol. 43, pp. 48-51, 1996.

Sanger, F. et al., << DNA sequencing with chain-terminating inhibitors, << Proc. Natl. Acad. Sci. USA, vol. 74, No. 12, pp. 5463-5467, 1977.

Sanghvi, Yogesh S. et al., ed., , *Carbohydrate Modifications in Antisense Research*, ACS Symposium Series 580, Chapters 2, 3, 6 and 7, American Chemical Society, Washington, DC, 1994.

Sawal, Hiroaki, << Synthesis and Proteins of Oligodenylic Acids Containing 2'-5' Phosphoramide Linkage, >> Chem. Lett., pp. 805-808, 1984.

Schwartz, R. M. et al., << Matrices for Detecting Distant Relationships, >> Atlas of Protein Sequence and Structure, Dayhoff, M., ed., vol. 5, Supplement 3, 1978.

Shimizu, Mikio, << Purification and Characterization of Phytase from *Bacillus subtilis* (natto) N-77, >>Biosci. Biotech. Biochem., vol. 56, No. 8, pp. 1266-1269, 1992.

Skinner, Richard H. et al., << Use of the Glu-Glu-Phe C-terminal Epitope for Rapid Purification of the Catalytic Domain of Normal and Mutant ras GTPase-activating Proteins, >> Journal of Biological Chemistry, vol. 266, No. 22, pp. 14163-14166, 1991.

Smith, Temple F. et al., << Comparison of Biosequences, >> Advances in Applied Mathematics, vol. 2, pp. 482-489, 1981.

Sojar, Hakimuddin T. et al., << A Chemical Method for the Deglycosylation of Proteins, >> Archives of Biochemistry and Biophysics, vol. 259, No. 1, pp. 52-57, 1987.

Sprinzl, Mathias et al., << Enzymatic Incorporation of ATP and CTP Analogues into the 3' End of tRNA, << Eur. J. Biochem., vol. 81, pp. 579-589, 1977.

Takamatsu, Nobuhiko et al., << Expression of bacterial chloramphenicol acetyltransferase gene in tobacco plants mediated by TMV-RNA, >> The EMBO Journal, vol. 6, No. 2, pp. 307-311, 1987.

Thotakura, Nageswar R. et al., << Enzymatic Deglycosylation of Glycoproteins, >> *Methods in Enzymology*, vol. 138, Complex Carbohydrates, Part E, Victor Ginsburg, ed., Academic Press, Inc., 1987.

Ullah, Abul, H. J. et al., << Extracellular Phytase (E. C. 3.1.3.8) from *Aspergillus ficuum* NRRL 315 : Purification and Characterization, >> Preparative Biochemistry, vol. 17, No. 1, pp. 63-91, 1987.

Van Hartingsveldt, Wim et al., << Cloning, characterization and overexpression of the phytase-encoding gene (phyA) of *Aspergillus niger*, >> Gene, vol. 127, pp. 87-94, 1993.

Von Kiedrowski, Gunter et al., << Parabolic Growth of a Self-Replicating Hexadeoxynucleotide Bearing a 3'-5'- Phosphoamidate Linkage, >> Angew. Chem. Int. Ed. Engl., vol. 30, No. 4, pp. 423-428, 1991.

Weber, Kristy L. et al., << Rapid Acquisition of Unknown DNA Sequence Adjacent to a Known Segment by Multiplex Restriction Site PCR, >> BioTechniques, vol. 25, No. 3, pp. 415-419, 1998.

Weidner, Gerhard et al., << Development of a homologous transformation system for the human pathogenic fungus *Aspergillus fumigatus* based onthe pyrG gene encoding orotidine 5'-monophosphate decarboxylase, << Curr. Genet., vol. 33, pp. 378-385, 1998.

Winter, Jill et al., << The Expression of Heat Shock Protein and Cognate Genes During Plant Development, >> *Heat Shock and Development*, Hightower, L. ed., Springer-Verlag, pp. 85-105, 1991.

Yamada, Koichi et al., << Phytase from *Aspergillus terreus*, >> Agr. Biol. Chem., vol. 32, No. 10, pp. 1275-1282, 1968.

\* cited by examiner

```
GTCGCATTCCGCCCGCTCTCTGCTCTGCATTCCGTATATGAGGTCGACAATGAGCTGAATCCATaAAACAAGGGTGATT
GATTCACACGGGGCTGTTGCTGCCGTATCGTCCAACCTGAGAGAGAGAGCCGCATCTCATCGCACGTTTCTCCTGCTATACATtT
CGCGGCTTACTGACGGCCTGCCCTCAACCTGAGAGAGAGAGCTCGATAGAGAGCGAGAGCGAGAGAGAGGGACCTTT
GCGTCACCTCTTGCTGAGGAAAAGCAGAGCAGAGCTCACATGCGGTAACTGACACCTCAGAACCATGCCTGTGCCAGAA
TCGTGGCCGCGATCCGAGGCGCGGCCCTCGCGAGATGCATACAAATACAGCGCCGTCCCCGACCTGGAGTCTGAACGAGAG
CCTCCGGCGGCAGTTTGATCGACGAGGTTCAACTCAAAGACAGCCTGCCGGGGAACCTGCACACTTTGCTGCGTC
TCAGGGACAGACTAGACTGATCAAGATGTCGCTCGGCGGCATGCGCTCTTTGCCATCTTGCTGACCATGCCTCACTCG
GCCGGTCTAAGCCCTCGTCGACTTGCGAAGTCGTCGGCAATTGCACAGAAGACGTTTCGCAGAATCTGGGGCCAATACTCA
CCCGTCTCTTCTCAGTCCCCTCCACCATTGACGCTTCCATCCCGGCGAGCTGCAGTTTGACTTTTGCGCAAGTCTTGTCCCG
CCATGGAGCGCGGTTCCCGACGCAAAAGAACGAAGTCTACCAAGAGATGATTGCGCGACGATTGACCCCCTTTGGTGAGCAG
ATTACGGCAAGGGATTCGAGTCTCAAGGACTATACGTACCACGCGGTACCAGCGCCTCTGATTCCGAACCTCTCGTGCGAGCCTC
CAGATGTGTGGACTGGACTCTGGACGAGATGGCCTTCTCGTGCGGCACAGAGAGTTCCTGAGGGGGTACTACGAAGCTCAGCACCGCGACGCTTAAACG
TGGGCTCGGCGAGCGAGTGGTTCTGTGTCATTCCCGAGAGACGAGGCATATAACAACACTCTGAACATGGAGCGTGCCCTGCGATCAACAGGAGGCT
CAACCAATGATGTTCTGTCATTCAGGGATTGAACCGAACCAGAAGGTCTGGCCGTCTTCGGGCCTGCGATCAACAGGAGGCT
GAAGGCCCGGCCATCTGAAATCAGGGATTGAACCTGATCGAGACCGTCGAGACGCTGATCATGATGGACCTGTGCCATTCACCACGTGG
CAACAGAGCAAGCTGCCTGGCGCCAACTGGCCGTCGATCGACGCTGATCGAGACCGTCGATCATGATGGACCTGTGCCATTCACCACGTGG
CCAATACGAGCGCGTGCCGTCAGGCGTATGGGAAGGCAACCCGATGGGCCCGTCTCAGGGGGTTGGATTCAGCAACGACTGATTGCCAG
GACAAGTGGTACGGGTATGGGAAGGCAACCCGATGGGCCCGTCTCAGGGGGTTGGATTCAGCAACGACTGATTGCCAG
GCTGACGGGCGAGCCTGTGCACGATGCGACGATGCGACGAACACGACACCATGTCTTCCATCTTTGCGGCCTCTTCACCCGAGACGTTCCCCCTGACG
CCAAGCTGTACGCCGACTTTTCGCACGACAAGCTGTCTCCCAAGAAGCTTCACGCTTCTCCGCGTCGCCGGCCATGTCGTGCCGTTGGTGCCCG
GATCTGCCGCTCAAGTACAAGCTGTCTCCCAAGAAGCTTCACGCTTCTCCGCGTCGCCGGCCATGTCGTGCCGTTGGTGCCCG
CATGTACGTGGAGAAGATGCAGTGCAGCGGCTCGAACGAGCGCGCTCGAACGAGCGCGCTGGTGCGATCATCCTCAACGACCGCGTGGTGCCGA
TGCGGACGTGCAACTCGGATCGACTGGGCGTGCGGGTGCAAGCTGGGTGCTTTTATTGATAGCCTGACGTTTGTGCGGCGGA
GGGCTGTGTGGAATCAGTGTCCTTTGAGGGTGAGGGGGCTGAGGGCGTCAAAGCAAATGGCATGACGTAAAAGACTTGTACAGTCTAAGGAC
CAGTAGGTACAATGAAGTCAATGTCATGGCGCTCAAAGCAAATGGCATGACGTAAAAGACTTGTACAGTCTAAGGAC
CGGGCTCGGCGTTGTGGGACTTCATGTTGCTTATTGAACCTCATTGGATCATGTTTGACAGCTCAGCATTACATTATC
AGTTGCTTCCTACCAAGTATAGCGTTATAAGGCGAGACTGCATAGCAAGNAGATGCTCCATACATGTACATATCAAATN
CCNCCACGTTCGATTGCTTGCCAAAAAAAAAAAAAAAAAAAAAAAAAAAAAGGGCGGCCGC
```

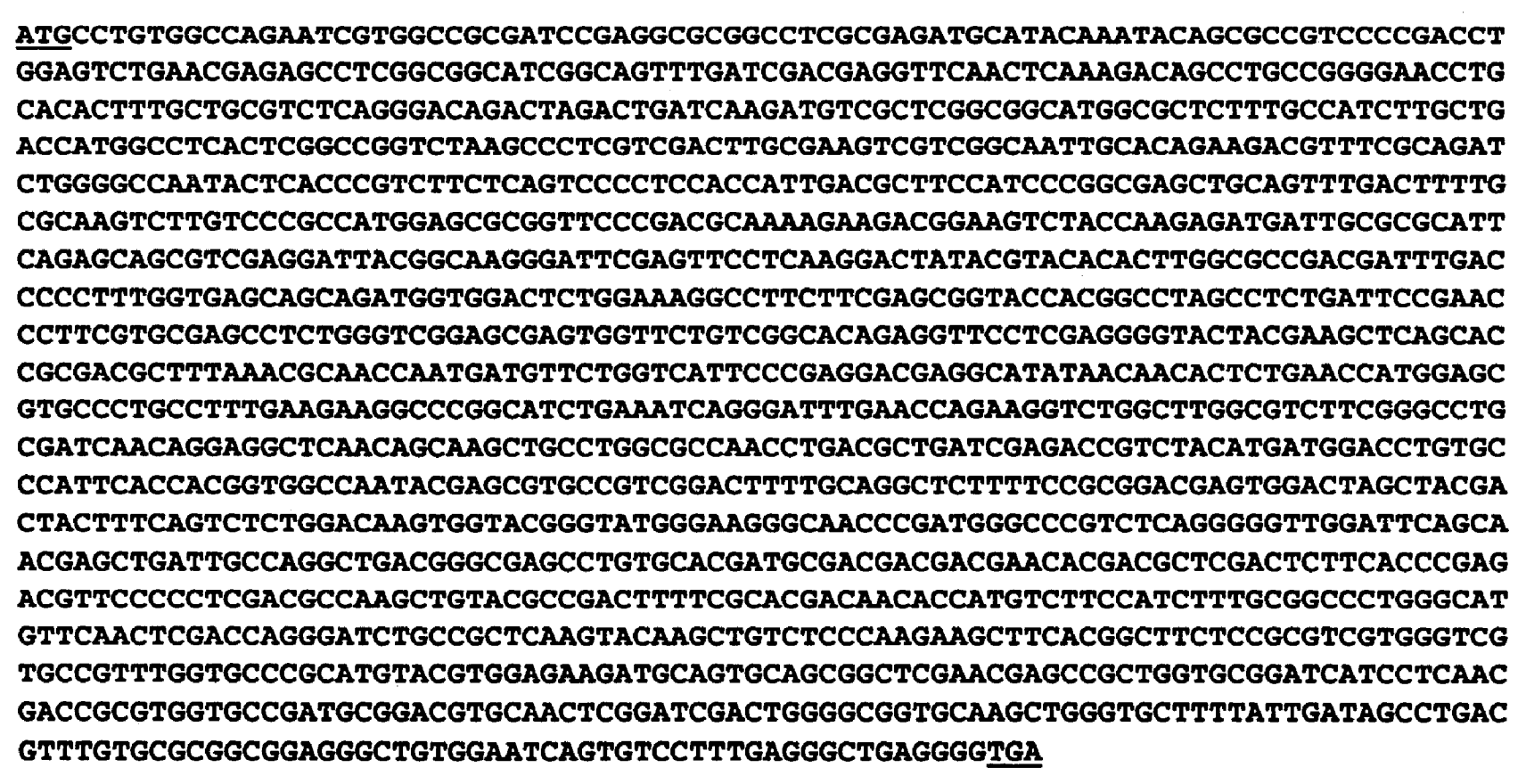

ATGTCGCTCGGCGGCATGGCGCTCTTTGCCATCTTGCTGACCATGGCCTCACTCGGCCGTCTAAGCCCTCGTCGACTTG
CGAAGTCGTCGGCAATTCCCGGCGAGCTGCAGTTTGACTTTGCGCAAGTCTTGTCCCGCCATGGAGCGCGGTTCCTCCACCA
TTGACGCTTCCATCCCGGCGAGCTGCAGTTTGACTTTGCGCAAGTCTTGTCCCGCGAGGATTCGAGTTCCT
AAGAAGACGGAAGTCTACCAAGATGATTGCGCCGACGATTTGACCCCCTTTGGTGAGCAGCAGATGGTGACTCTGAAAGGCCT
CAAGGACTATACGTACACACTTGGCGCCGACGATTTGACCCCCTTTGGTGAGCAGCAGATGGTGACTCTGAAAGGCCT
TCTTCGAGCGAGGTTCCTCCACCGGCGTACCAGCCCTCTGATTCCGAAACCCTTCGTGCGACGCTTTAAACGCAACCAATGATGTTCTGTCATTCC
GCACAGAGGTTCCTCCACCGGCGTACCAGCCCTCTGATTCCGAAACCCTTCGTGCGACGCTTTAAACGCAACCAATGATGTTCTGTCATTCC
CGAGGACGAGGAGCATATAACAACACTCTGAACCATGGAGCGTCTTGGGCGTCTTGGGCCCTGCAATCTGAAATCAGG
ATTTGAACCAGAAGGTCTGGCTTGGCGTCTTGGGCCTGCGATCAACAGAGAGCTCAACAGCAAGCTGCCTGGCGCCAAC
CTGACGCTGATCGAGACCGTCTACATGATGACCTGTGCCCATTCACCACGAGCGCCAATAACGAGCGTGCCGTCGACTT
TTGCAGGCTCTTTTCCGGGACGAGTGGACTAGCTACGACTACTTTCAGTCTCTGGACAAGTGGTACGGTATGGAAGG
GCAACCCGATGGCCCCGTCGAACGCTCTCAGGGGGTTGGATTCAGCAGCAGCTGTTCCCCCTCGACGCCAAGCTCCGCCCCTCGACGCCAAGCTCTGCCCGCTCAAGTACAAGCTGT
GCGACGACGAACACGACCTGCTCCATCTTTGCGCCTCTGCGGCCCTCGTGGGTCGTGCCGCATGTCGTGCCGCATGTGCGGATGCAACTCGACT
AGCGGCTCGAACGACCGCTCAAGCGCTCCATCTTTGCGCCTCTGCGGCCCTCGTGGGTCGTGCCGCATGTGCGGATGCAACTCGACT
GGGGCCGTGCAAGCTGGTGTGCTTTATTGATAGCCTGACGTTTGTGCGGCGCGGAGGGCTGTGAATCAGTGTCCTTTGA
GGGCTGAGGGGTGA

FIG._4

MPVARIVAAIRGAASRDAYKYSAVPDLESEREPRRHRQFDRRGSTQRQPAGEPAHFAASQGQTRLIKMSLGMALFAILL
TMASLGRSKPSSTCEVVGNCTEDVSQIWGQYSPVFSVPSTIDASIPASCSLTFAQVLSRHGARFPTQKKTEVYQEMIARI
QSSVEDYGKGFEFLKDYTYTLGADDLTPFGEQMVDSGKAFFERYHGLASDSEPFVRASGSERVVLSAQRFLEGYYEAQH
RDALNATNDVLVIPEDEAYNNTLNHGACPAFEEGPASEIRDLNQKVWLGVFGPAINRRLNSKLPGANLTLIETVYMDLC
PFTTVANTSVPSDFCRLFSADEWTSYDYFQSLDKWYGYGKGNPMGPSQGVGFSNELIARLTGEPVHDATTNTTLDSSPE
TFPLDAKLYADFSHDNTMSSIFAALGMFNSTRDLPLRKYKLSPKKLHGFSASWVVPFGARMYVEKMQCSGSNEPLVRIILN
DRVVPMRTCNSDRLGRCKLGAFIDSLTFVRGGGLWNQCPLRAEG

FIG._5

MSLGGMALFAILLLTMASLGRSKPSSTCEVVGNCTEDVSQIWGQYSPVFSVPSTIDASIPASCSLTFAQVLSRHGARFPTQ
KKTEVYQEMIARIQSSVEDYGKGFEFLKDYTYTLGADDLTPFGEQMVDSGKAFFERYHGLASDSEPFVRASGSERVVLS
AQRFLEGYYEAQHRDALNATNDVLVIPEDEAYNNTLNHGACPAFEEGPASEIRDLNQKVWLGVFGPAINRRLNSKLPGAN
LTLIETVYMDLCPFTTVANTSVPSDFCRLFSADEWTSYDYFQSLDKWYGYGKGNPMGPSQGVGFSNELIARLTGEPVHD
ATTNTTLDSSPETFPLDAKLYADFSHDNTMSSIFAALGMFNSTRDLPLRKYKLSPKKLHGFSASWVVPFGARMYVEKMQC
SGSNEPLVRIILNDRVVPMRTCNSDRLGRCKLGAFIDSLTFVRGGGLWNQCPLRAEG

```
T. reesei:    73  MALFAILLTMASLGRSRPSSTCEVVGN----------------CTEDVSQIMGQYSPVFSVP--S 119
                  MA F + L++    L  S+ S+    VV N                C  +VS +WGQY6P FS+  S
E. nidulans:   1  MAFFTVALSLYYi-LSRVSAQAPVVQNHSCNTADGGYQCFPNVSHVWGQYSPYFSIEQES      59

120  TIDASIPASCSLTFAQVLSRHGARFPTQKKTEVYQEMIARIQSSVEDYGKGFEFLKDYTY     179
                  I   +P   C  +TF  QVLSRHGAR+PT+  Y   +I  IQ +    +    FL+ Y Y
              60  AISEDVPHGCEVTFVQVLSRHGARYPTESKSKAYSGLIEAIQRNATSFWGQYAFLESYNY    119

180  TLGADDLTPFGEQQMVDSGKAFFERYHGLASDSEPFVRASGSERVVLSAQRFLEGYYEAQ     239
                  TLGADDLT FGE QMVDSG  F+ RY LA  + PF+RASGS+RVV SA++F+ G+ +AQ
             120  TLGADDLTIFGENQMVDSGAKFYRAYPTESRRYKMLARKNTPFIRASGSDRVVASAAEKFINGPRKAQ 179

240  HRD---ALMATMDV-LVIPEDEAYANTLNHGACPAFEEGPASEIRDLNQKVMLGVFGPAIN  296
                   D  +  AT V  ++IPE + ++NTL+H   C  +FE    ++ + M   + GP I
             180  LHDHGSKRATPVVNVLIPEIDGFMMTLDHSTCVSFENDERADEIEAN---FTAIMGPPIR   236

297  RRLNSKLPGANLTLIETVIMMDLCPFFTTVANISVPSD---FCRLFSADEWTSYDYFQSLD  353
                  +RL + LPG  LT    +Y+MD+C F T+A  T+    ++     FC +F+  EW  YDY QSL
             237  KRLENDLPGIKLTNENVIYLAMDMCBFDTMARTAHGTELSPFCAIFTEKEWLQYDYLQSLS  296

354  KWYGYGKGRPMGPSQGVGFSNELIARLTGEFVHDATTNTTLDSSPETPPLDAKLYADFS    413
                  K+ YG+G  G+P+GP+QG+GF+NELIARLT  PV D T+TN TLDS+P  TPPLD KLYADFS
             297  KTYGYGAGSPLGPAQGIGFTNELIARLTQSPVQDNTSTNHTLDSNPATFPLDRKLYADFS      356

414  HDNTMSSIFAALGMFNSTRDXXXXXXXXXXXXXHGFSA+SWVVPFGARMIVERMQCSGSNEP 473
                  HDN+M SIF A+G++N T+              G++ASW VPFGAR Y E MQC       EP
             357  HDNSMISIFFAMGLYNGTQPLSMDSVESIQEMDGYAASWTVPFGARAYTELMQCE-RKEP    415

474  LVRIILMDRVVPKRTCNSDRLGRCKLGAFIDSLITFVRGGGLMNQC    518
                  LVR+++ MDRVVP+    C  D+ GRC L  ++ L F R GG W C
             416  LVRVLVNDRKVVPLHGCAVDRFGRCTLDDWVEGLMFARSGGNMKTC    460
```

FIG._6

```
T. reesei:   88  SKPSSTCEVVGN----CTEDVSQINGQYSPVTSVP--STIDASIPASCSLTFAQVLSRHGA  142
                 S+ STC+ V       C  + S +WGQY+P FS+    S I  +PA C +TFAQVLSRHGA
A. awari:    25  SRNQSTCDTVDQGYQCFSETSHLWGQYAPFFSLANESAISPDVPAGCRVTFAQVLSRHGA   84

143  RFPTQKKTEVIQEMIARIQSSVEDYGKGFEFLKDYTYLGADDLTPFGEQQMVDSGXAPF   202
                 R+PT+ R + Y +I IQ +V + + FLR Y +LGADDLTPFGEQ+++V+SG  F+
             85  RYPTESKGRKYSALIEEIQQNVTTFDGKYAFLKTYNYSLGADDLTPFGEQELVNSGIKFY   144

203  ERYHGLASDSEPFVRASGSERVVLSAQRFLEGYYEAQHRD------ALNATNDVLVIPEDE 257
                 +RY L  + PF+R+SGS RV+ S ++F+EG+   +D          ++ +VI E
            145  QRYESLTRNLIPFIRSSGSSRVIASGEKFIEGFQSTKLKDPRAQPGQSSPKIDVVISEAS   204

258  AYNNYLMHGACPAFEEGPASEIRDLNQKVWLGVFGPAINRRLNSKLPGANLTLIETVYMM  317
                 + NNTL+ G C FE+   SE+ D +  + P P+I +RL +L G  LT E Y+M
            205  SSNNTLDFGTCTVFED---SELADYVEANFTATFAPSIRQRLENDLSGVTLTDTVTYLM   261

318  DLCPFTTVANISVP----SDFCRLFBADEWTSYDYFQSLDKWTGYGKGMPNGPSQGVGFSN 374
                 D+C F T++ ++V     B FC LF+ DEW YDY QSL K+YG+G GMP+GP+QGVG+ +N
            262  DMCSFDTISTSTVDIKLSPFCDLFTEDEWIHYDYLQSLKKYGHGAGMPLGPTQGVGYAN   321

375  ELIARLTGEPVHDATTNTLDSSPETFPLDAKLYADFSHDNTMSSIFAALGMFNSTRDX   434
                 ELIARLT  PVHD T++N TLDS+P TFPL++ LYADFSHDN + SI  ALG+++N T+
            322  ELIARLTBSPVHDDYTSSMKTLDSNPATFPLNSTLYADFSHDNGIISILPALGLYNGTKPL 381

435  XXXXXXXXXXHGFSASNVVPFGARMYVERMQCSGSNEPLVRIILNDRVVPMRTCNSDRL  494
                          GFS++W VPF +R+YVE MQC      EPLVR+++NDRKVVP+  C  D L
            382  STTTVEMITQTDGFSSAWTVPFASRLYVEHMQCQAEQEPLVRVLVNDRVVPLHGCPIDAL  441

495  GRCKLGAFIDSLTFVRGGGLWNQC  518
                 GRC    +F+  L+F R GG W +C
            442  GRCTRDSFVRGLSFARSGGDWAEC  465
```

FIG._7

```
T. reesei:   68   MSLGGHALFAILLTMASLGRSKPSG----TCEVVGN---TCEDVSQIWGQYSPVTSVP--- 118
                  M + + L  LL+  + G + P+S      +C+ V    C  + S +WGQY+P PS+
A. niger:     1   MGVSAVLLPLYLLSGVTSGLAVPASRMQSSCDTVDQGYQCFSETSHLWGQYAPFFSLANE  60

119   STIDASIPASCSLTFAQVLSRHGARFPTQKKTEVTQEMIARIQSSVEDYGKGFEFLKDYT 178
                  S I  +PA C  +TFAQVLSRHGAR+PT K + Y +I IQ +      + FLK Y
             61   SVISPEVPAGCRVTFAQVLSRHGARYPTDSKQRKYSALIEEIQQNATTFDGKYAFLKTYN 120

179   YTLGADDLTPFGEQQMVDSGKAFFPERYHGLASDSEPFVRASGSSERVVLSAQRFLEGYYEA 238
                  Y+LGADDLTPFGEQ++V+SG F++RY L + PF+R+SGS RV+ S ++F+EG+
            121   YSLGADDLTPFGEQELVNSGIKFYQNYESLTRNIVPFIRSSGSSRVIASGRKFIEGFQST 180

239   QHRD-----ALNATNDVLVIPEDEAYNNTLMHQACPAFEEGPASEIRDLNQKVWLGVFGP 293
                  + +D          +VI E + MNTL+ G C  FE+    SE+ D  +    P  P
            181   KLKDPRAQPGQSSPKIDVVTSEASSSMNTLDPGNCTVFED---SELADTVEANFTATFVF 237

294   AINRRILNSKLPGANLTLIETVYMNDLCPPTTVANTSVP---SDFCRLFSADEWTSYDTFQ 350
                  +I +RL + L G LT E Y+MD+C F T++  ++V     S FC LF+ DEW +YDY Q
            238   SIRQRLEMDLSGVTLTDTEVTYLMDMCSFDTISTSTVDTRLSPFCDLFTBDEWTNYDYLQ 297

351   SLDKWYGYGKGMEMGPSQGVGFSNELIARLTGEPVHDATTTWFTLDSSPETFPLDAKLKA 410
                  SL K+YG+G     GNP+GP+GP++GVG++NELIARLT  PVHD T++N TLDSSP TFPL4++ LYA
            298   SLKKYYGHGAGMPLGFTQGGVGYAMBLLARLTHSPVHDDTSSMHTLDSSPATPPLNSTLYA 357

411   DFSHDMTMSSIFAALGMFDSTRDXXXXXXXXXXXHGFSASWVPFGAEMTVERMQCSGS 470
                  DFSHDN + BI  ALG++N T+                 GF8++N VPF  +R+YVE MQC
            358   DFSHDMGIISILPALGLYNGTKPLSTTTVENITQTDGFSSAWTVPFASRLYVEMHKQCQAE 417

471   NEPLVRIILWDRVYVPMRTCNSDRLGRCXLGAFIDSLTFVRGGGLWNQC 518
                  EPLVR+++NDRVVP+   C  D LGRC   +F+  L+F R GG W +C
            418   QEPLVRVLVNDRVVPLEGCFVDALGRCTRDSFVRGLSFARSGGDNAEC 465
```

FIG._8

SEQUENCE LISTING

```
<160> NUMBER OF SEQ ID NOS: 53

<210> SEQ ID NO 1
<211> LENGTH: 2220
<212> TYPE: DNA
<213> ORGANISM: Trichoderma reesei
<220> FEATURE:
<221> NAME/KEY: misc_feature
<222> LOCATION: 2131, 2160, 2163
<223> OTHER INFORMATION: n = A,T,C or G

<400> SEQUENCE: 1
```

```
gtcgcattcc gcccgctctc tgctctgcat ctccgtatat gaggtcgaca atgagctgaa    60
tccataaaac aagggtgatt gattcacacg ggctgttgct gccgtatcgt ccaatctacg   120
gccgcatctc atcgcacgtt tctcctcctg ctatacattt cgcggcttac tgacggcctg   180
ccctcaacct ggagagagat agtctgatag agagcgagag cgagagagag ggggaccttt   240
gcgtcacctc ttgctgagga aaagcagagc agagctcaca tgcggtaact gacacctcag   300
aaccatgcct gtggccagaa tcgtggccgc gatccgaggc gcggcctcgc gagatgcata   360
caaatacagc gccgtccccg acctggagtc tgaacgagag cctcggcggc atcggcagtt   420
tgatcgacga ggttcaactc aaagacagcc tgccggggaa cctgcacact tgctgcgtc    480
tcagggacag actagactga tcaagatgtc gctcggcggc atggcgctct ttgccatctt   540
gctgaccatg gcctcactcg gccggtctaa gccctcgtcg acttgcgaag tcgtcggcaa   600
ttgcacagaa gacgtttcgc agatctgggg ccaatactca cccgtcttct cagtcccctc   660
caccattgac gcttccatcc cggcgagctg cagtttgact tttgcgcaag tcttgtcccg   720
ccatggagcg cggttcccga cgcaaaagaa gacggaagtc taccaagaga tgattgcgcg   780
cattcagagc agcgtcgagg attacggcaa gggattcgag ttcctcaagg actatacgta   840
cacacttggc gccgacgatt tgaccccctt tggtgagcag cagatggtgg actctggaaa   900
ggccttcttc gagcggtacc acggcctagc ctctgattcc gaacccttcg tgcgagcctc   960
tgggtcggag cgagtggttc tgtcggcaca gaggttcctc gagggtact acgaagctca   1020
gcaccgcgac gctttaaacg caaccaatga tgttctggtc attcccgagg acgaggcata   1080
taacaacact ctgaaccatg gagcgtgccc tgcctttgaa aaggcccgg catctgaaat   1140
cagggatttg aaccagaagg tctggcttgg cgtcttcggg cctgcgatca acaggaggct   1200
caacagcaag ctgcctggcg ccaacctgac gctgatcgag accgtctaca tgatggacct   1260
gtgcccattc accacggtgg ccaatacgag cgtgccgtcg acttttgca ggctcttttc    1320
cgcggacgag tggactagct acgactactt tcagtctctg acaagtggt acgggtatgg    1380
gaagggcaac ccgatgggcc cgtctcaggg ggttggattc agcaacgagc tgattgccag   1440
gctgacgggc gagcctgtgc acgatgcgac gacgacgaac acgacgctcg actcttcacc   1500
cgagacgttc cccctcgacg ccaagctgta cgccgacttt tcgcacgaca caccatgtc    1560
ttccatcttt gcggccctgg gcatgttcaa ctcgaccagg gatctgccgc tcaagtacaa   1620
gctgtctccc aagaagcttc acggcttctc cgcgtcgtgg gtcgtgccgt ttggtgcccg   1680
catgtacgtg gagaagatgc agtgcagcgg ctcgaacgag ccgctggtgc ggatcatcct   1740
caacgaccgc gtggtgccga tgcggacgtg caactcggat cgactggggc ggtgcaagct   1800
gggtgctttt attgatagcc tgacgtttgt gcgcggcgga gggctgtgga atcagtgtcc   1860
tttgagggct gaggggtgat tacaatgcga agaacaagat ttagattcag aacttaccta   1920
cagtaggtac atgaaagtca atgtcatggc gcgtcaaagc aaatggcatg acggtaaaag   1980
acttgtacag tctaagggac cgggctcggc gttgtgggac ttcatgttgc ttattgaacc   2040
tcattgggat catgtttgac agctcagcat ttacattatc agttgcttcc taccaagtat   2100
agcgttataa ggcggagact gcatagcaag nagatgctcc atacatgtac atatcaaatn   2160
cnccacgtt cgattgcttg ccaaaaaaaa aaaaaaaaaa aaaaaaaaaa gggcggccgc    2220
```

<210> SEQ ID NO 2
<211> LENGTH: 1575
<212> TYPE: DNA

<213> ORGANISM: Trichoderma reesei

<400> SEQUENCE: 2

```
atgcctgtgg ccagaatcgt ggccgcgatc cgaggcgcgg cctcgcgaga tgcatacaaa    60
tacagcgccg tccccgacct ggagtctgaa cgagagcctc ggcggcatcg gcagtttgat   120
cgacgaggtt caactcaaag acagcctgcc ggggaacctg cacactttgc tgcgtctcag   180
ggacagacta gactgatcaa gatgtcgctc ggcggcatgg cgctctttgc catcttgctg   240
accatggcct cactcggccg gtctaagccc tcgtcgactt gcgaagtcgt cggcaattgc   300
acagaagacg tttcgcagat ctggggccaa tactcacccg tcttctcagt ccctccacc    360
attgacgctt ccatcccggc gagctgcagt ttgacttttg cgcaagtctt gtcccgccat   420
ggagcgcggt tcccgacgca aagaagacg gaagtctacc aagagatgat gcgcgcatt    480
cagagcagcg tcgaggatta cggcaaggga ttcgagttcc tcaaggacta cgtacaca    540
cttggcgcca acgatttgac cccctttggt gagcagcaga tggtggactc tggaaaggcc   600
ttcttcgagc ggtaccacgg cctagcctct gattccgaac ccttcgtgcg agcctctggg   660
tcggagcgag tggttctgtc ggcacagagg ttcctcgagg gtactacga agctcagcac    720
cgcgacgctt taaacgcaac caatgatgtt ctggtcattc ccgaggacga ggcatataac   780
aacactctga accatggagc gtgccctgcc tttgaagaag cccggcatc tgaaatcagg    840
gatttgaacc agaaggtctg gcttggcgtc ttcgggcctg cgatcaacag gaggctcaac   900
agcaagctgc ctggcgccaa cctgacgctg atcgagaccg tctacatgat ggacctgtgc   960
ccattcacca cggtggccaa tacgagcgtg ccgtcggact tttgcaggct cttttccgcg  1020
gacgagtgga ctagctacga ctactttcag tctctggaca gtggtacgg gtatgggaag  1080
ggcaacccga tgggcccgtc tcaggggggtt ggattcagca acgagctgat tgccaggctg  1140
acgggcgagc ctgtgcacga tgcgacgacg acgaacacga cgctcgactc ttcacccgag  1200
acgttccccc tcgacgccaa gctgtacgcc gacttttcgc acgacaacac catgtcttcc  1260
atctttgcgg ccctgggcat gttcaactcg accagggatc tgccgctcaa gtacaagctg  1320
tctcccaaga gcttcacgg cttctccgcg tcgtgggtcg tgccgtttgg tgcccgcatg  1380
tacgtggaga gatgcagtg cagcggctcg aacgagccgc tggtgcggat catcctcaac  1440
gaccgcgtgg tgccgatgcg gacgtgcaac tcggatcgac tggggcggtg caagctgggt  1500
gcttttattg atagcctgac gtttgtgcgc ggcggagggc tgtggaatca gtgtcctttg  1560
agggctgagg ggtga                                                   1575
```

<210> SEQ ID NO 3
<211> LENGTH: 1374
<212> TYPE: DNA
<213> ORGANISM: Trichoderma reesei

<400> SEQUENCE: 3

```
atgtcgctcg gcggcatggc gctctttgcc atcttgctga ccatggcctc actcggccgg    60
tctaagccct cgtcgacttg cgaagtcgtc ggcaattgca cagaagacgt ttcgcagatc   120
tggggccaat actcacccgt cttctcagtc cctccacca ttgacgcttc catcccggcg    180
agctgcagtt tgacttttgc gcaagtcttg tcccgccatg gagcgcggtt cccgacgcaa   240
aagaagacgg aagtctacca agagatgatg cgcgcattc agagcagcgt cgaggattac    300
ggcaagggat tcgagttcct caaggactat acgtacacac ttggcgccga cgatttgacc   360
ccctttggtg agcagcagat ggtggactct ggaaaggcct tcttcgagcg gtaccacggc   420
```

-continued

```
ctagcctctg attccgaacc cttcgtgcga gcctctgggt cggagcgagt ggttctgtcg      480
gcacagaggt tcctcgaggg gtactacgaa gctcagcacc gcgacgcttt aaacgcaacc      540
aatgatgttc tggtcattcc cgaggacgag gcatataaca acactctgaa ccatggagcg      600
tgccctgcct ttgaagaagg cccggcatct gaaatcaggg atttgaacca gaaggtctgg      660
cttggcgtct tcgggcctgc gatcaacagg aggctcaaca gcaagctgcc tggcgccaac      720
ctgacgctga tcgagaccgt ctacatgatg gacctgtgcc cattcaccac ggtggccaat      780
acgagcgtgc cgtcggactt ttgcaggctc ttttccgcgg acgagtggac tagctacgac      840
tactttcagt ctctggacaa gtggtacggg tatgggaagg gcaacccgat gggcccgtct      900 caggggttg gattcagcaa cgagctgatt gccaggctga cgggcgagcc tgtgcacgat      960
gcgacgacga cgaacacgac gctcgactct tcacccgaga cgttccccct cgacgccaag      1020
ctgtacgccg acttttcgca cgacaacacc atgtcttcca tctttgcggc cctgggcatg      1080
ttcaactcga ccagggatct gccgctcaag tacaagctgt ctcccaagaa gcttcacggc      1140
ttctccgcgt cgtgggtcgt gccgtttggt ccccgcatgt acgtggagaa gatgcagtgc      1200
agcggctcga acgagccgct ggtgcggatc atcctcaacg accgcgtggt gccgatgcgg      1260 cgtgcaact cggatcgact ggggcggtgc aagctgggtg cttttattga tagcctgacg      1320 ttgtgcgcg gcggagggct gtggaatcag tgtcctttga gggctgaggg gtga             1374
```

<210> SEQ ID NO 4
<211> LENGTH: 524
<212> TYPE: PRT
<213> ORGANISM: Trichoderma reesei

<400> SEQUENCE: 4

```
Met Pro Val Ala Arg Ile Val Ala Ala Ile Arg Gly Ala Ala Ser Arg
  1               5                  10                  15

Asp Ala Tyr Lys Tyr Ser Ala Val Pro Asp Leu Glu Ser Glu Arg Glu
             20                  25                  30

Pro Arg Arg His Arg Gln Phe Asp Arg Arg Gly Ser Thr Gln Arg Gln
         35                  40                  45

Pro Ala Gly Glu Pro Ala His Phe Ala Ala Ser Gln Gly Gln Thr Arg
     50                  55                  60

Leu Ile Lys Met Ser Leu Gly Gly Met Ala Leu Phe Ala Ile Leu Leu
 65                  70                  75                  80

Thr Met Ala Ser Leu Gly Arg Ser Lys Pro Ser Thr Cys Glu Val
             85                  90                  95

Val Gly Asn Cys Thr Glu Asp Val Ser Gln Ile Trp Gly Gln Tyr Ser
            100                 105                 110

Pro Val Phe Ser Val Pro Ser Thr Ile Asp Ala Ser Ile Pro Ala Ser
        115                 120                 125

Cys Ser Leu Thr Phe Ala Gln Val Leu Ser Arg His Gly Ala Arg Phe
    130                 135                 140

Pro Thr Gln Lys Lys Thr Glu Val Tyr Gln Glu Met Ile Ala Arg Ile
145                 150                 155                 160

Gln Ser Ser Val Glu Asp Tyr Gly Lys Gly Phe Glu Phe Leu Lys Asp
                165                 170                 175

Tyr Thr Tyr Thr Leu Gly Ala Asp Asp Leu Thr Pro Phe Gly Glu Gln
            180                 185                 190

Gln Met Val Asp Ser Gly Lys Ala Phe Phe Glu Arg Tyr His Gly Leu
        195                 200                 205
```

```
Ala Ser Asp Ser Glu Pro Phe Val Arg Ala Gly Ser Glu Arg Val
    210                 215                 220

Val Leu Ser Ala Gln Arg Phe Leu Glu Gly Tyr Tyr Glu Ala Gln His
225                 230                 235                 240

Arg Asp Ala Leu Asn Ala Thr Asn Asp Val Leu Val Ile Pro Glu Asp
                245                 250                 255

Glu Ala Tyr Asn Asn Thr Leu Asn His Gly Ala Cys Pro Ala Phe Glu
            260                 265                 270

Glu Gly Pro Ala Ser Glu Ile Arg Asp Leu Asn Gln Lys Val Trp Leu
        275                 280                 285

Gly Val Phe Gly Pro Ala Ile Asn Arg Arg Leu Asn Ser Lys Leu Pro
    290                 295                 300

Gly Ala Asn Leu Thr Leu Ile Glu Thr Val Tyr Met Met Asp Leu Cys
305                 310                 315                 320

Pro Phe Thr Thr Val Ala Asn Thr Ser Val Pro Ser Asp Phe Cys Arg
                325                 330                 335

Leu Phe Ser Ala Asp Glu Trp Thr Ser Tyr Asp Tyr Phe Gln Ser Leu
            340                 345                 350

Asp Lys Trp Tyr Gly Tyr Gly Lys Gly Asn Pro Met Gly Pro Ser Gln
        355                 360                 365

Gly Val Gly Phe Ser Asn Glu Leu Ile Ala Arg Leu Thr Gly Glu Pro
    370                 375                 380

Val His Asp Ala Thr Thr Thr Asn Thr Thr Leu Asp Ser Ser Pro Glu
385                 390                 395                 400

Thr Phe Pro Leu Asp Ala Lys Leu Tyr Ala Asp Phe Ser His Asp Asn
                405                 410                 415

Thr Met Ser Ser Ile Phe Ala Ala Leu Gly Met Phe Asn Ser Thr Arg
            420                 425                 430

Asp Leu Pro Leu Lys Tyr Lys Leu Ser Pro Lys Lys Leu His Gly Phe
        435                 440                 445

Ser Ala Ser Trp Val Val Pro Phe Gly Ala Arg Met Tyr Val Glu Lys
    450                 455                 460

Met Gln Cys Ser Gly Ser Asn Glu Pro Leu Val Arg Ile Ile Leu Asn
465                 470                 475                 480

Asp Arg Val Val Pro Met Arg Thr Cys Asn Ser Asp Arg Leu Gly Arg
                485                 490                 495

Cys Lys Leu Gly Ala Phe Ile Asp Ser Leu Thr Phe Val Arg Gly Gly
            500                 505                 510

Gly Leu Trp Asn Gln Cys Pro Leu Arg Ala Glu Gly
        515                 520

<210> SEQ ID NO 5
<211> LENGTH: 457
<212> TYPE: PRT
<213> ORGANISM: Trichoderma reesei

<400> SEQUENCE: 5

Met Ser Leu Gly Gly Met Ala Leu Phe Ala Ile Leu Leu Thr Met Ala
 1               5                  10                  15

Ser Leu Gly Arg Ser Lys Pro Ser Ser Thr Cys Glu Val Val Gly Asn
                20                  25                  30

Cys Thr Glu Asp Val Ser Gln Ile Trp Gly Gln Tyr Ser Pro Val Phe
            35                  40                  45

Ser Val Pro Ser Thr Ile Asp Ala Ser Ile Pro Ala Ser Cys Ser Leu
```

-continued

```
            50                  55                  60
Thr Phe Ala Gln Val Leu Ser Arg His Gly Ala Arg Phe Pro Thr Gln
 65                  70                  75                  80

Lys Lys Thr Glu Val Tyr Gln Glu Met Ile Ala Arg Ile Gln Ser Ser
                 85                  90                  95

Val Glu Asp Tyr Gly Lys Gly Phe Glu Phe Leu Lys Asp Tyr Thr Tyr
                100                 105                 110

Thr Leu Gly Ala Asp Asp Leu Thr Pro Phe Gly Glu Gln Gln Met Val
                115                 120                 125

Asp Ser Gly Lys Ala Phe Phe Glu Arg Tyr His Gly Leu Ala Ser Asp
            130                 135                 140

Ser Glu Pro Phe Val Arg Ala Ser Gly Ser Glu Arg Val Val Leu Ser
145                 150                 155                 160

Ala Gln Arg Phe Leu Glu Gly Tyr Tyr Glu Ala Gln His Arg Asp Ala
                165                 170                 175

Leu Asn Ala Thr Asn Asp Val Leu Val Ile Pro Glu Asp Glu Ala Tyr
            180                 185                 190

Asn Asn Thr Leu Asn His Gly Ala Cys Pro Ala Phe Glu Glu Gly Pro
            195                 200                 205

Ala Ser Glu Ile Arg Asp Leu Asn Gln Lys Val Trp Leu Gly Val Phe
            210                 215                 220

Gly Pro Ala Ile Asn Arg Arg Leu Asn Ser Lys Leu Pro Gly Ala Asn
225                 230                 235                 240

Leu Thr Leu Ile Glu Thr Val Tyr Met Met Asp Leu Cys Pro Phe Thr
                245                 250                 255

Thr Val Ala Asn Thr Ser Val Pro Ser Asp Phe Cys Arg Leu Phe Ser
            260                 265                 270

Ala Asp Glu Trp Thr Ser Tyr Asp Tyr Phe Gln Ser Leu Asp Lys Trp
            275                 280                 285

Tyr Gly Tyr Gly Lys Gly Asn Pro Met Gly Pro Ser Gln Gly Val Gly
            290                 295                 300

Phe Ser Asn Glu Leu Ile Ala Arg Leu Thr Gly Glu Pro Val His Asp
305                 310                 315                 320

Ala Thr Thr Thr Asn Thr Thr Leu Asp Ser Ser Pro Glu Thr Phe Pro
                325                 330                 335

Leu Asp Ala Lys Leu Tyr Ala Asp Phe Ser His Asp Asn Thr Met Ser
                340                 345                 350

Ser Ile Phe Ala Ala Leu Gly Met Phe Asn Ser Thr Arg Asp Leu Pro
            355                 360                 365

Leu Lys Tyr Lys Leu Ser Pro Lys Lys Leu His Gly Phe Ser Ala Ser
            370                 375                 380

Trp Val Val Pro Phe Gly Ala Arg Met Tyr Val Glu Lys Met Gln Cys
385                 390                 395                 400

Ser Gly Ser Asn Glu Pro Leu Val Arg Ile Ile Leu Asn Asp Arg Val
                405                 410                 415

Val Pro Met Arg Thr Cys Asn Ser Asp Arg Leu Gly Arg Cys Lys Leu
                420                 425                 430

Gly Ala Phe Ile Asp Ser Leu Thr Phe Val Arg Gly Gly Leu Trp
            435                 440                 445

Asn Gln Cys Pro Leu Arg Ala Glu Gly
            450                 455
```

<210> SEQ ID NO 6

```
<211> LENGTH: 445
<212> TYPE: PRT
<213> ORGANISM: Trichoderma reesei
<220> FEATURE:
<221> NAME/KEY: VARIANT
<222> LOCATION: (361)...(372)
<223> OTHER INFORMATION: Xaa = Any Amino Acid

<400> SEQUENCE: 6
```

| | | | | | | | | | | | | | | |
|---|---|---|---|---|---|---|---|---|---|---|---|---|---|---|
| Met | Ala | Leu | Phe | Ala | Ile | Leu | Leu | Thr | Met | Ala | Ser | Leu | Gly | Arg | Ser |
| 1 | | | | 5 | | | | | 10 | | | | | 15 | |

Lys Pro Ser Ser Thr Cys Glu Val Val Gly Asn Cys Thr Glu Asp Val
              20              25              30

Ser Gln Ile Trp Gly Gln Tyr Ser Pro Val Phe Ser Val Pro Thr Ile
        35                40              45

Asp Ala Ser Ile Pro Ala Ser Cys Ser Leu Thr Phe Ala Gln Val Leu
50                 55                  60

Ser Arg His Gly Ala Arg Phe Pro Thr Gln Lys Lys Thr Glu Val Tyr
65                 70              75              80

Gln Glu Met Ile Ala Arg Ile Gln Ser Val Glu Asp Tyr Gly Lys
              85              90              95

Gly Phe Glu Phe Leu Lys Asp Tyr Thr Tyr Thr Leu Gly Ala Asp Asp
        100              105            110

Leu Thr Pro Phe Gly Glu Gln Gln Met Val Asp Ser Gly Lys Ala Phe
        115              120            125

Phe Glu Arg Tyr His Gly Leu Ala Ser Asp Ser Glu Pro Phe Val Arg
    130              135            140

Ala Ser Gly Ser Glu Arg Val Val Leu Ser Ala Gln Arg Phe Leu Glu
145                150              155              160

Gly Tyr Tyr Glu Ala Gln His Arg Asp Ala Leu Asn Ala Thr Asn Asp
              165            170            175

Val Leu Val Ile Pro Glu Asp Glu Ala Tyr Asn Asn Thr Leu Asn His
        180              185            190

Gly Ala Cys Pro Ala Phe Glu Glu Gly Pro Ala Ser Glu Ile Arg Asp
              195            200            205

Leu Asn Gln Lys Val Trp Leu Gly Val Phe Gly Pro Ala Ile Asn Arg
210                 215              220

Arg Leu Asn Ser Lys Leu Pro Gly Ala Asn Leu Thr Leu Ile Glu Thr
225                230              235              240

Val Tyr Met Met Asp Leu Cys Pro Phe Thr Thr Val Ala Asn Thr Ser
              245            250            255

Val Pro Ser Asp Phe Cys Arg Leu Phe Ser Ala Asp Glu Trp Thr Ser
        260              265            270

Tyr Asp Tyr Phe Gln Ser Leu Asp Lys Trp Tyr Gly Tyr Gly Lys Gly
    275              280            285

Asn Pro Met Gly Pro Ser Gln Gly Val Gly Phe Ser Asn Glu Leu Ile
        290              295            300

Ala Arg Leu Thr Gly Glu Pro Val His Asp Ala Thr Thr Asn Thr
305                310              315              320

Thr Leu Asp Ser Ser Pro Glu Thr Phe Pro Leu Asp Ala Lys Leu Tyr
              325            330            335

Ala Asp Phe Ser His Asp Asn Thr Met Ser Ser Ile Phe Ala Ala Leu
        340              345            350

Gly Met Phe Asn Ser Thr Arg Asp Xaa Xaa Xaa Xaa Xaa Xaa Xaa
              355            360            365

```
Xaa Xaa Xaa Xaa His Gly Phe Ser Ala Ser Trp Val Val Pro Phe Gly
        370             375                 380

Ala Arg Met Tyr Val Glu Lys Met Gln Cys Ser Gly Ser Asn Glu Pro
385                 390                 395                 400

Leu Val Arg Ile Ile Leu Asn Asp Arg Val Val Pro Met Arg Thr Cys
                405                 410                 415

Asn Ser Asp Arg Leu Gly Arg Cys Lys Leu Gly Ala Phe Ile Asp Ser
            420                 425                 430

Leu Thr Phe Val Arg Gly Gly Gly Leu Trp Asn Gln Cys
        435                 440                 445

<210> SEQ ID NO 7
<211> LENGTH: 460
<212> TYPE: PRT
<213> ORGANISM: Emericella nidulans

<400> SEQUENCE: 7

Met Ala Phe Phe Thr Val Ala Leu Ser Leu Tyr Leu Leu Ser Arg
 1               5                  10                  15

Val Ser Ala Gln Ala Pro Val Val Gln Asn His Ser Cys Asn Thr Ala
            20                  25                  30

Asp Gly Gly Tyr Gln Cys Phe Pro Asn Val Ser His Val Trp Gly Gln
        35                  40                  45

Tyr Ser Pro Tyr Phe Ser Ile Glu Gln Glu Ser Ala Ile Ser Glu Asp
    50                  55                  60

Val Pro His Gly Cys Glu Val Thr Phe Val Gln Val Leu Ser Arg His
65                  70                  75                  80

Gly Ala Arg Tyr Pro Thr Glu Ser Lys Ser Lys Ala Tyr Ser Gly Leu
                85                  90                  95

Ile Glu Ala Ile Gln Lys Asn Ala Thr Ser Phe Trp Gly Gln Tyr Ala
            100                 105                 110

Phe Leu Glu Ser Tyr Asn Tyr Thr Leu Gly Ala Asp Asp Leu Thr Ile
        115                 120                 125

Phe Gly Glu Asn Gln Met Val Asp Ser Gly Ala Lys Phe Tyr Arg Arg
    130                 135                 140

Tyr Lys Asn Leu Ala Arg Lys Asn Thr Pro Phe Ile Arg Ala Ser Gly
145                 150                 155                 160

Ser Asp Arg Val Val Ala Ser Ala Glu Lys Phe Ile Asn Gly Phe Arg
                165                 170                 175

Lys Ala Gln Leu His Asp His Gly Ser Lys Arg Ala Thr Pro Val Val
            180                 185                 190

Asn Val Ile Ile Pro Glu Ile Asp Gly Phe Asn Asn Thr Leu Asp His
        195                 200                 205

Ser Thr Cys Val Ser Phe Glu Asn Asp Glu Arg Ala Asp Glu Ile Glu
    210                 215                 220

Ala Asn Phe Thr Ala Ile Met Gly Pro Pro Ile Arg Lys Arg Leu Glu
225                 230                 235                 240

Asn Asp Leu Pro Gly Ile Lys Leu Thr Asn Glu Asn Val Ile Tyr Leu
                245                 250                 255

Met Asp Met Cys Ser Phe Asp Thr Met Ala Arg Thr Ala His Gly Thr
            260                 265                 270

Glu Leu Ser Pro Phe Cys Ala Ile Phe Thr Glu Lys Glu Trp Leu Gln
        275                 280                 285

Tyr Asp Tyr Leu Gln Ser Leu Ser Lys Tyr Tyr Gly Tyr Gly Ala Gly
    290                 295                 300
```

```
Ser Pro Leu Gly Pro Ala Gln Gly Ile Gly Phe Thr Asn Glu Leu Ile
305                 310                 315                 320

Ala Arg Leu Thr Gln Ser Pro Val Gln Asp Asn Thr Ser Thr Asn His
                325                 330                 335

Thr Leu Asp Ser Asn Pro Ala Thr Phe Pro Leu Asp Arg Lys Leu Tyr
            340                 345                 350

Ala Asp Phe Ser His Asp Asn Ser Met Ile Ser Ile Phe Phe Ala Met
        355                 360                 365

Gly Leu Tyr Asn Gly Thr Gln Pro Leu Ser Met Asp Ser Val Glu Ser
    370                 375                 380

Ile Gln Glu Met Asp Gly Tyr Ala Ala Ser Trp Thr Val Pro Phe Gly
385                 390                 395                 400

Ala Arg Ala Tyr Phe Glu Leu Met Gln Cys Glu Lys Lys Glu Pro Leu
                405                 410                 415

Val Arg Val Leu Val Asn Asp Arg Val Val Pro Leu His Gly Cys Ala
                420                 425                 430

Val Asp Lys Phe Gly Arg Cys Thr Leu Asp Asp Trp Val Glu Gly Leu
            435                 440                 445

Asn Phe Ala Arg Ser Gly Gly Asn Trp Lys Thr Cys
450                 455                 460

<210> SEQ ID NO 8
<211> LENGTH: 224
<212> TYPE: PRT
<213> ORGANISM: Artificial Sequence
<220> FEATURE:
<223> OTHER INFORMATION: consensus sequence

<400> SEQUENCE: 8

Met Ala Phe Leu Leu Ser Ser Val Val Asn Cys Val Ser Trp Gly Gln
1               5                   10                  15

Tyr Ser Pro Phe Ser Ser Ile Pro Cys Thr Phe Gln Val Leu Ser Arg
            20                  25                  30

His Gly Ala Arg Pro Thr Lys Tyr Ile Ile Gln Phe Leu Tyr Tyr Thr
        35                  40                  45

Leu Gly Ala Asp Asp Leu Thr Phe Gly Glu Gln Met Val Asp Ser Gly
    50                  55                  60

Phe Arg Tyr Leu Ala Pro Phe Arg Ala Ser Gly Ser Arg Val Val Ser
65                  70                  75                  80

Ala Phe Gly Ala Gln Asp Ala Thr Val Ile Pro Glu Asn Asn Thr Leu
                85                  90                  95

His Cys Phe Glu Asn Gly Pro Ile Arg Leu Leu Pro Gly Leu Thr Tyr
            100                 105                 110

Met Asp Cys Phe Thr Ala Thr Phe Cys Phe Glu Trp Tyr Asp Tyr Gln
        115                 120                 125

Ser Leu Lys Tyr Gly Tyr Gly Gly Pro Gly Pro Gln Gly Gly Phe Asn
    130                 135                 140

Glu Leu Ile Ala Arg Leu Thr Pro Val Asp Thr Thr Asn Thr Leu Asp
145                 150                 155                 160

Ser Pro Thr Phe Pro Leu Asp Lys Leu Tyr Ala Asp Phe Ser His Asp
                165                 170                 175

Asn Met Ser Ile Phe Ala Gly Asn Thr Gly Ala Ser Trp Val Pro Phe
            180                 185                 190

Gly Ala Arg Tyr Glu Met Gln Cys Glu Pro Leu Val Arg Asn Asp Arg
        195                 200                 205
```

```
Val Val Pro Cys Asp Gly Arg Cys Leu Leu Phe Arg Gly Gly Trp Cys
    210                 215                 220
```

<210> SEQ ID NO 9
<211> LENGTH: 431
<212> TYPE: PRT
<213> ORGANISM: Trichoderma reesei
<220> FEATURE:
<221> NAME/KEY: VARIANT
<222> LOCATION: (347)...(358)
<223> OTHER INFORMATION: Xaa = Any Amino Acid

<400> SEQUENCE: 9

```
Ser Lys Pro Ser Ser Thr Cys Glu Val Val Gly Asn Cys Thr Glu Asp
  1               5                  10                  15

Val Ser Gln Ile Trp Gly Gln Tyr Ser Pro Val Phe Ser Val Pro Ser
             20                  25                  30

Thr Ile Asp Ala Ser Ile Pro Ala Ser Cys Ser Leu Thr Phe Ala Gln
         35                  40                  45

Val Leu Ser Arg His Gly Ala Arg Phe Pro Thr Gln Lys Lys Thr Glu
     50                  55                  60

Val Tyr Gln Glu Met Ile Ala Arg Ile Gln Ser Ser Val Glu Asp Tyr
 65                  70                  75                  80

Gly Lys Gly Phe Glu Phe Leu Lys Asp Tyr Thr Tyr Thr Leu Gly Ala
                 85                  90                  95

Asp Asp Leu Thr Pro Phe Gly Glu Gln Gln Met Val Asp Ser Gly Lys
            100                 105                 110

Ala Phe Phe Glu Arg Tyr His Gly Leu Ala Ser Asp Ser Glu Pro Phe
        115                 120                 125

Val Arg Ala Ser Gly Ser Glu Arg Val Val Leu Ser Ala Gln Arg Phe
    130                 135                 140

Leu Glu Gly Tyr Tyr Glu Ala Gln His Arg Asp Ala Leu Asn Ala Thr
145                 150                 155                 160

Asn Asp Val Leu Val Ile Pro Glu Asp Glu Ala Tyr Asn Asn Thr Leu
                165                 170                 175

Asn His Gly Ala Cys Pro Ala Phe Glu Glu Gly Pro Ala Ser Glu Ile
            180                 185                 190

Arg Asp Leu Asn Gln Lys Val Trp Leu Gly Val Phe Gly Pro Ala Ile
        195                 200                 205

Asn Arg Arg Leu Asn Ser Lys Leu Pro Gly Ala Asn Leu Thr Leu Ile
    210                 215                 220

Glu Thr Val Tyr Met Met Asp Leu Cys Pro Phe Thr Thr Val Ala Asn
225                 230                 235                 240

Thr Ser Val Pro Ser Asp Phe Cys Arg Leu Phe Ser Ala Asp Glu Trp
                245                 250                 255

Thr Ser Tyr Asp Tyr Phe Gln Ser Leu Asp Lys Trp Tyr Gly Tyr Gly
            260                 265                 270

Lys Gly Asn Pro Met Gly Pro Ser Gln Gly Val Gly Phe Ser Asn Glu
        275                 280                 285

Leu Ile Ala Arg Leu Thr Gly Glu Pro Val His Asp Ala Thr Thr Thr
    290                 295                 300

Asn Thr Thr Leu Asp Ser Ser Pro Glu Thr Phe Pro Leu Asp Ala Lys
305                 310                 315                 320

Leu Tyr Ala Asp Phe Ser His Asp Asn Thr Met Ser Ser Ile Phe Ala
                325                 330                 335
```

```
Ala Leu Gly Met Phe Asn Ser Thr Arg Asp Xaa Xaa Xaa Xaa Xaa
                340                 345                 350

Xaa Xaa Xaa Xaa Xaa Xaa His Gly Phe Ser Ala Ser Trp Val Val Pro
            355                 360                 365

Phe Gly Ala Arg Met Tyr Val Glu Lys Met Gln Cys Ser Gly Ser Asn
        370                 375                 380

Glu Pro Leu Val Arg Ile Ile Leu Asn Asp Arg Val Val Pro Met Arg
385                 390                 395                 400

Thr Cys Asn Ser Asp Arg Leu Gly Arg Cys Lys Leu Gly Ala Phe Ile
            405                 410                 415

Asp Ser Leu Thr Phe Val Arg Gly Gly Leu Trp Asn Gln Cys
        420                 425                 430

<210> SEQ ID NO 10
<211> LENGTH: 441
<212> TYPE: PRT
<213> ORGANISM: Aspergillus awamon

<400> SEQUENCE: 10

Ser Arg Asn Gln Ser Thr Cys Asp Thr Val Asp Gln Gly Tyr Gln Cys
1               5                   10                  15

Phe Ser Glu Thr Ser His Leu Trp Gly Gln Tyr Ala Pro Phe Phe Ser
            20                  25                  30

Leu Ala Asn Glu Ser Ala Ile Ser Pro Asp Val Pro Ala Gly Cys Arg
        35                  40                  45

Val Thr Phe Ala Gln Val Leu Ser Arg His Gly Ala Arg Tyr Pro Thr
    50                  55                  60

Glu Ser Lys Gly Lys Lys Tyr Ser Ala Leu Ile Glu Glu Ile Gln Gln
65                  70                  75                  80

Asn Val Thr Thr Phe Asp Gly Lys Tyr Ala Phe Leu Lys Thr Tyr Asn
                85                  90                  95

Tyr Ser Leu Gly Ala Asp Asp Leu Thr Pro Phe Gly Glu Gln Glu Leu
            100                 105                 110

Val Asn Ser Gly Ile Lys Phe Tyr Gln Arg Tyr Glu Ser Leu Thr Arg
        115                 120                 125

Asn Ile Ile Pro Phe Ile Arg Ser Ser Gly Ser Ser Arg Val Ile Ala
    130                 135                 140

Ser Gly Glu Lys Phe Ile Glu Gly Phe Gln Ser Thr Lys Leu Lys Asp
145                 150                 155                 160

Pro Arg Ala Gln Pro Gly Gln Ser Ser Pro Lys Ile Asp Val Val Ile
                165                 170                 175

Ser Glu Ala Ser Ser Ser Asn Asn Thr Leu Asp Pro Gly Thr Cys Thr
            180                 185                 190

Val Phe Glu Asp Ser Glu Leu Ala Asp Thr Val Glu Ala Asn Phe Thr
        195                 200                 205

Ala Thr Phe Ala Pro Ser Ile Arg Gln Arg Leu Glu Asn Asp Leu Ser
    210                 215                 220

Gly Val Thr Leu Thr Asp Thr Glu Val Thr Tyr Leu Met Asp Met Cys
225                 230                 235                 240

Ser Phe Asp Thr Ile Ser Thr Ser Thr Val Asp Thr Lys Leu Ser Pro
                245                 250                 255

Phe Cys Asp Leu Phe Thr His Asp Glu Trp Ile His Tyr Asp Tyr Leu
            260                 265                 270

Gln Ser Leu Lys Lys Tyr Tyr Gly His Gly Ala Gly Asn Pro Leu Gly
        275                 280                 285
```

```
Pro Thr Gln Gly Val Gly Tyr Ala Asn Glu Leu Ile Ala Arg Leu Thr
    290                 295                 300

His Ser Pro Val His Asp Asp Thr Ser Ser Asn His Thr Leu Asp Ser
305                 310                 315                 320

Asn Pro Ala Thr Phe Pro Leu Asn Ser Thr Leu Tyr Ala Asp Phe Ser
                325                 330                 335

His Asp Asn Gly Ile Ile Ser Ile Leu Phe Ala Leu Gly Leu Tyr Asn
            340                 345                 350

Gly Thr Lys Pro Leu Ser Thr Thr Val Glu Asn Ile Thr Gln Thr
        355                 360                 365

Asp Gly Phe Ser Ser Ala Trp Thr Val Pro Phe Ala Ser Arg Leu Tyr
    370                 375                 380

Val Glu Met Met Gln Cys Gln Ala Glu Gln Pro Leu Val Arg Val
385                 390                 395                 400

Leu Val Asn Asp Arg Val Val Pro Leu His Gly Cys Pro Ile Asp Ala
                405                 410                 415

Leu Gly Arg Cys Thr Arg Asp Ser Phe Val Arg Gly Leu Ser Phe Ala
            420                 425                 430

Arg Ser Gly Gly Asp Trp Ala Glu Cys
            435                 440
```

<210> SEQ ID NO 11
<211> LENGTH: 212
<212> TYPE: PRT
<213> ORGANISM: Artificial Sequence
<220> FEATURE:
<223> OTHER INFORMATION: consensus sequence

<400> SEQUENCE: 11

```
Ser Ser Thr Cys Val Cys Ser Trp Gly Gln Tyr Pro Phe Ser Ser Ile
1               5                   10                  15

Pro Ala Cys Thr Phe Ala Gln Val Leu Ser Arg His Gly Ala Arg Pro
                20                  25                  30

Thr Lys Tyr Ile Ile Gln Val Phe Leu Lys Tyr Leu Gly Ala Asp
        35                  40                  45

Asp Leu Thr Pro Phe Gly Glu Gln Val Ser Gly Phe Arg Tyr Leu Pro
50                  55                  60

Phe Arg Ser Gly Ser Arg Val Ser Phe Glu Gly Asp Val Ile Glu Asn
65                  70                  75                  80

Asn Thr Leu Gly Cys Phe Glu Ser Glu Asp Phe Pro Ile Arg Leu Leu
                85                  90                  95

Gly Leu Thr Glu Tyr Met Asp Cys Phe Thr Val Ser Phe Cys Leu Phe
            100                 105                 110

Asp Glu Trp Tyr Asp Tyr Gln Ser Leu Lys Tyr Gly Gly Asn Pro
        115                 120                 125

Gly Pro Gln Gly Val Gly Asn Glu Leu Ile Ala Arg Leu Thr Pro Val
    130                 135                 140

His Asp Thr Asn Thr Leu Asp Ser Pro Thr Phe Pro Leu Leu Tyr Ala
145                 150                 155                 160

Asp Phe Ser His Asp Asn Ser Ile Ala Leu Gly Asn Thr Gly Phe Ser
                165                 170                 175

Trp Val Pro Phe Arg Tyr Val Glu Met Gln Cys Glu Pro Leu Val Arg
            180                 185                 190

Asn Asp Arg Val Val Pro Cys Asp Leu Gly Arg Cys Phe Leu Phe Arg
        195                 200                 205
```

```
Gly Gly Trp Cys
    210

<210> SEQ ID NO 12
<211> LENGTH: 451
<212> TYPE: PRT
<213> ORGANISM: Trichoderma reesei
<220> FEATURE:
<221> NAME/KEY: VARIANT
<222> LOCATION: (367)...(378)
<223> OTHER INFORMATION: Xaa = Any Amino Acid

<400> SEQUENCE: 12

Met Ser Leu Gly Gly Met Ala Leu Phe Ala Ile Leu Leu Thr Met Ala
 1               5                  10                  15

Ser Leu Gly Arg Ser Lys Pro Ser Ser Thr Cys Glu Val Val Gly Asn
            20                  25                  30

Cys Thr Glu Asp Val Ser Gln Ile Trp Gly Gln Tyr Ser Pro Val Phe
        35                  40                  45

Ser Val Pro Ser Thr Ile Asp Ala Ser Ile Pro Ala Ser Cys Ser Leu
    50                  55                  60

Thr Phe Ala Gln Val Leu Ser Arg His Gly Ala Arg Phe Pro Thr Gln
65                  70                  75                  80

Lys Lys Thr Glu Val Tyr Gln Glu Met Ile Ala Arg Ile Gln Ser Ser
                85                  90                  95

Val Glu Asp Tyr Gly Lys Gly Phe Glu Phe Leu Lys Asp Tyr Thr Tyr
            100                 105                 110

Thr Leu Gly Ala Asp Asp Leu Thr Pro Phe Gly Glu Gln Gln Met Val
        115                 120                 125

Asp Ser Gly Lys Ala Phe Phe Glu Arg Tyr His Gly Leu Ala Ser Asp
    130                 135                 140

Ser Glu Pro Phe Val Arg Ala Ser Gly Ser Glu Arg Val Val Leu Ser
145                 150                 155                 160

Ala Gln Arg Phe Leu Glu Gly Tyr Tyr Glu Ala Gln His Arg Asp Ala
                165                 170                 175

Leu Asn Ala Thr Asn Asp Val Leu Val Ile Pro Glu Asp Glu Ala Tyr
            180                 185                 190

Asn Asn Thr Leu Asn His Gly Ala Cys Pro Ala Phe Glu Glu Gly Pro
        195                 200                 205

Ala Ser Glu Ile Arg Asp Leu Asn Gln Lys Val Trp Leu Gly Val Phe
    210                 215                 220

Gly Pro Ala Ile Asn Arg Arg Leu Asn Ser Lys Leu Pro Gly Ala Asn
225                 230                 235                 240

Leu Thr Leu Ile Glu Thr Val Tyr Met Met Asp Leu Cys Pro Phe Thr
                245                 250                 255

Thr Val Ala Asn Thr Ser Val Pro Ser Asp Phe Cys Arg Leu Phe Ser
            260                 265                 270

Ala Asp Glu Trp Thr Ser Tyr Asp Tyr Phe Gln Ser Leu Asp Lys Trp
        275                 280                 285

Tyr Gly Tyr Gly Lys Gly Asn Pro Met Gly Pro Ser Gln Gly Val Gly
    290                 295                 300

Phe Ser Asn Glu Leu Ile Ala Arg Leu Thr Gly Glu Pro Val His Asp
305                 310                 315                 320

Ala Thr Thr Thr Asn Thr Thr Leu Asp Ser Ser Pro Glu Thr Phe Pro
                325                 330                 335
```

```
Leu Asp Ala Lys Leu Tyr Ala Asp Phe Ser His Asp Asn Thr Met Ser
            340                 345                 350

Ser Ile Phe Ala Ala Leu Gly Met Phe Asn Ser Thr Arg Asp Xaa Xaa
            355                 360                 365

Xaa Xaa Xaa Xaa Xaa Xaa Xaa Xaa Xaa His Gly Phe Ser Ala Ser
            370                 375                 380

Trp Val Val Pro Phe Gly Ala Arg Met Tyr Val Glu Lys Met Gln Cys
385                 390                 395                 400

Ser Gly Ser Asn Glu Pro Leu Val Arg Ile Ile Leu Asn Asp Arg Val
            405                 410                 415

Val Pro Met Arg Thr Cys Asn Ser Asp Arg Leu Gly Arg Cys Lys Leu
            420                 425                 430

Gly Ala Phe Ile Asp Ser Leu Thr Phe Val Arg Gly Gly Leu Trp
            435                 440                 445

Asn Gln Cys
    450

<210> SEQ ID NO 13
<211> LENGTH: 465
<212> TYPE: PRT
<213> ORGANISM: Aspergillus niger

<400> SEQUENCE: 13

Met Gly Val Ser Ala Val Leu Leu Pro Leu Tyr Leu Leu Ser Gly Val
1               5                   10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
            35                  40                  45

Gly Gln Tyr Ala Pro Phe Phe Ser Leu Ala Asn Glu Ser Val Ile Ser
        50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Lys Tyr Ser
            85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
            115                 120                 125

Thr Pro Phe Gly Glu Gln Glu Leu Val Asn Ser Gly Ile Lys Phe Tyr
            130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
            165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
            195                 200                 205

Thr Leu Asp Pro Gly Thr Cys Thr Val Phe Glu Asp Ser Glu Leu Ala
            210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
            245                 250                 255
```

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
            275                 280                 285

Glu Trp Ile Asn Tyr Asp Tyr Leu Gln Ser Leu Lys Lys Tyr Tyr Gly
            290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
                340                 345                 350

Ser Thr Leu Tyr Ala Asp Phe Ser His Asp Asn Gly Ile Ile Ser Ile
                355                 360                 365

Leu Phe Ala Leu Gly Leu Tyr Asn Gly Thr Lys Pro Leu Ser Thr Thr
            370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
            435                 440                 445

Phe Val Arg Gly Leu Ser Phe Ala Arg Ser Gly Gly Asp Trp Ala Glu
            450                 455                 460

Cys
465

<210> SEQ ID NO 14
<211> LENGTH: 216
<212> TYPE: PRT
<213> ORGANISM: Artificial Sequence
<220> FEATURE:
<223> OTHER INFORMATION: consensus sequence

<400> SEQUENCE: 14

Met Leu Leu Leu Gly Pro Ser Cys Val Cys Ser Trp Gly Gln Tyr Pro
1               5                   10                  15

Phe Ser Ser Ile Pro Ala Cys Thr Phe Ala Gln Val Leu Ser Arg His
            20                  25                  30

Gly Ala Arg Pro Thr Lys Tyr Ile Ile Gln Phe Leu Lys Tyr Tyr Leu
        35                  40                  45

Gly Ala Asp Asp Leu Thr Pro Phe Gly Glu Gln Val Ser Gly Phe Arg
    50                  55                  60

Tyr Leu Pro Phe Arg Ser Gly Ser Arg Val Ser Phe Glu Gly Asp Val
65                  70                  75                  80

Ile Glu Asn Asn Thr Leu Gly Cys Phe Glu Ser Glu Asp Phe Pro Ile
                85                  90                  95

Arg Leu Leu Gly Leu Thr Glu Tyr Met Asp Cys Phe Thr Val Ser Phe
            100                 105                 110

Cys Leu Phe Asp Glu Trp Tyr Asp Tyr Gln Ser Leu Lys Tyr Gly Gly
        115                 120                 125

Gly Asn Pro Gly Pro Gln Gly Val Gly Asn Glu Leu Ile Ala Arg Leu
    130                 135                 140

```
Thr Pro Val His Asp Thr Asn Thr Leu Asp Ser Ser Pro Thr Phe Pro
145                 150                 155                 160

Leu Leu Tyr Ala Asp Phe Ser His Asp Asn Ser Ile Ala Leu Gly Asn
            165                 170                 175

Thr Gly Phe Ser Trp Val Pro Phe Arg Tyr Val Glu Met Gln Cys Glu
        180                 185                 190

Pro Leu Val Arg Asn Asp Arg Val Val Pro Cys Asp Leu Gly Arg Cys
        195                 200                 205

Phe Leu Phe Arg Gly Gly Trp Cys
    210                 215

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
taattatttc aatctcattc tcac                                           24

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
atcgtaatat gcagcttgaa tggg                                           24

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
cgaggttcaa ctcaaagaca gc                                             22

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
tctggcttgg cgtcttcgg                                                 19

<210> SEQ ID NO 19
<211> LENGTH: 8
<212> TYPE: PRT
<213> ORGANISM: Artificial Sequence
<220> FEATURE:
<223> OTHER INFORMATION: conserved BOX1 sequence
<220> FEATURE:
<221> NAME/KEY: VARIANT
<222> LOCATION: 1
<223> OTHER INFORMATION: Xaa = Val or Leu
<220> FEATURE:
<221> NAME/KEY: VARIANT
<222> LOCATION: 3
<223> OTHER INFORMATION: Xaa = Ala or Ser
```

```
<400> SEQUENCE: 19

Xaa Leu Xaa Arg His Gly Ala Arg
1               5

<210> SEQ ID NO 20
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 3, 6, 9, 12, 18, 21
<223> OTHER INFORMATION: n = inosine

<400> SEQUENCE: 20
btnytnkcnm gncayggnhc nmg                                          23

<210> SEQ ID NO 21
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 3, 6, 12, 18, 21
<223> OTHER INFORMATION: n = inosine

<400> SEQUENCE: 21
btnytnagym gncayggnhc nmg                                          23

<210> SEQ ID NO 22
<211> LENGTH: 5
<212> TYPE: PRT
<213> ORGANISM: Artificial Sequence
<220> FEATURE:
<223> OTHER INFORMATION: conserved BOX2 sequence
<220> FEATURE:
<221> NAME/KEY: VARIANT
<222> LOCATION: 5
<223> OTHER INFORMATION: Xaa = Asp, Glu, or His

<400> SEQUENCE: 22

Asn Asn Thr Leu Xaa
1               5

<210> SEQ ID NO 23
<211> LENGTH: 14
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 9, 12
<223> OTHER INFORMATION: n = inosine

<400> SEQUENCE: 23
aayaayacny tnsa                                                    14

<210> SEQ ID NO 24
<211> LENGTH: 14
<212> TYPE: DNA
<213> ORGANISM: Artificial Sequence
<220> FEATURE:
<223> OTHER INFORMATION: primer
<220> FEATURE:
```

```
<221> NAME/KEY: misc_feature
<222> LOCATION: 3, 6
<223> OTHER INFORMATION: n = inosine

<400> SEQUENCE: 24
tsnarngtrt trtt                                                              14
> SEQ ID NO 25
<211> LENGTH: 5
<212> TYPE: PRT
<213> ORGANISM: Artificial Sequence
<220> FEATURE:
<223> OTHER INFORMATION: conserved BOX3 sequence

<400> SEQUENCE: 25

Leu Ser Pro Phe Cys
 1               5

<210> SEQ ID NO 26
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 6, 9
<223> OTHER INFORMATION: n = inosine

<400> SEQUENCE: 26
ytttcnccnt tytgy                                                             15

<210> SEQ ID NO 27
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 3, 9
<223> OTHER INFORMATION: n = inosine

<400> SEQUENCE: 27
ytnagyccnt tytgy                                                             15

<210> SEQ ID NO 28
<211> LENGTH: 12
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 7, 9, 11
<223> OTHER INFORMATION: n = inosine

<400> SEQUENCE: 28
rcaraangna nr                                                                12

<210> SEQ ID NO 29
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 7, 13
<223> OTHER INFORMATION: n = inosine
```

```
<400> SEQUENCE: 29
rcaraanggr ctnar                                                    15

<210> SEQ ID NO 30
<211> LENGTH: 6
<212> TYPE: PRT
<213> ORGANISM: Artificial Sequence
<220> FEATURE:
<223> OTHER INFORMATION: conserved BOX4 sequence
<220> FEATURE:
<221> NAME/KEY: VARIANT
<222> LOCATION: 2
<223> OTHER INFORMATION: Xaa = Asn or Ser

<400> SEQUENCE: 30

Gly Xaa Pro Leu Gly Pro
 1               5

<210> SEQ ID NO 31
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 3, 6, 9, 12, 15
<223> OTHER INFORMATION: n = inosine

<400> SEQUENCE: 31
ggnwvnccny tnggncc                                                  17

<210> SEQ ID NO 32
<211> LENGTH: 14
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 3, 6, 9, 12
<223> OTHER INFORMATION: n = inosine

<400> SEQUENCE: 32
ccnarnggnb wncc                                                     14

<210> SEQ ID NO 33
<211> LENGTH: 5
<212> TYPE: PRT
<213> ORGANISM: Artificial Sequence
<220> FEATURE:
<223> OTHER INFORMATION: conserved BOX5 sequence

<400> SEQUENCE: 33

Asp Phe Ser His Asp
 1               5

<210> SEQ ID NO 34
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 9
<223> OTHER INFORMATION: n = inosine

<400> SEQUENCE: 34
```

```
gayttytcnc aygay                                              15

<210> SEQ ID NO 35
<211> LENGTH: 15
<212> TYPE: DNA
<213> ORGANISM: Artificial Sequence
<220> FEATURE:
<223> OTHER INFORMATION: primer

<400> SEQUENCE: 35
gayttyagyc aygay                                              15

<210> SEQ ID NO 36
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 7
<223> OTHER INFORMATION: n = inosine

<400> SEQUENCE: 36
rtcrtgngar aartc                                              15

<210> SEQ ID NO 37
<211> LENGTH: 15
<212> TYPE: DNA
<213> ORGANISM: Artificial Sequence
<220> FEATURE:
<223> OTHER INFORMATION: primer

<400> SEQUENCE: 37
rtcrtgrctr aartc                                              15

<210> SEQ ID NO 38
<211> LENGTH: 8
<212> TYPE: PRT
<213> ORGANISM: Artificial Sequence
<220> FEATURE:
<223> OTHER INFORMATION: conserved BOX6 sequence
<220> FEATURE:
<221> NAME/KEY: VARIANT
<222> LOCATION: 3
<223> OTHER INFORMATION: Xaa = Ala or Val
<220> FEATURE:
<221> NAME/KEY: VARIANT
<222> LOCATION: 5
<223> OTHER INFORMATION: Xaa = Ile or Val

<400> SEQUENCE: 38

Val Arg Xaa Ile Xaa Asn Asp Arg
 1               5

<210> SEQ ID NO 39
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 9, 12, 15, 18, 21
<223> OTHER INFORMATION: n = inosine

<400> SEQUENCE: 39
ckrtcrttna ynarnrcnck nac                                     23
```

```
<210> SEQ ID NO 40
<211> LENGTH: 7
<212> TYPE: PRT
<213> ORGANISM: Artificial Sequence
<220> FEATURE:
<223> OTHER INFORMATION: conserved BOX2.5 sequence

<400> SEQUENCE: 40

Met Asp Met Cys Ser Phe Asp
  1               5

<210> SEQ ID NO 41
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 15
<223> OTHER INFORMATION: n = inosine

<400> SEQUENCE: 41
atggayatgt gytcnttyga                                              20

<210> SEQ ID NO 42
<211> LENGTH: 6
<212> TYPE: PRT
<213> ORGANISM: Artificial Sequence
<220> FEATURE:
<223> OTHER INFORMATION: conserved BOX4' sequence

<400> SEQUENCE: 42

Tyr Gly His Gly Ala Gly
  1               5

<210> SEQ ID NO 43
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 15
<223> OTHER INFORMATION: n = inosine

<400> SEQUENCE: 43
ttrccrgcrc crtgnccrta                                              20

<210> SEQ ID NO 44
<211> LENGTH: 17
<212> TYPE: DNA
<213> ORGANISM: Artificial Sequence
<220> FEATURE:
<223> OTHER INFORMATION: degenerate primer
<220> FEATURE:
<221> NAME/KEY: misc_feature
<222> LOCATION: 9
<223> OTHER INFORMATION: n = inosine

<400> SEQUENCE: 44
gayttywsnc aygayaa                                                 17

<210> SEQ ID NO 45
<211> LENGTH: 17
<212> TYPE: DNA
```

```
<213> ORGANISM: Artificial Sequence
<220> FEATURE:
<223> OTHER INFORMATION: degenerate primer
<220> FEATURE:
<221> NAME/KEY: misc_feature
<222> LOCATION: 3, 12
<223> OTHER INFORMATION: n = inosine

<400> SEQUENCE: 45
gcngayttyw sncayga                                                    17

<210> SEQ ID NO 46
<211> LENGTH: 17
<212> TYPE: DNA
<213> ORGANISM: Artificial Sequence
<220> FEATURE:
<223> OTHER INFORMATION: degenerate primer
<220> FEATURE:
<221> NAME/KEY: misc_feature
<222> LOCATION: 3, 6
<223> OTHER INFORMATION: n = inosine

<400> SEQUENCE: 46
aynacnckrt crttsac                                                    17

<210> SEQ ID NO 47
<211> LENGTH: 17
<212> TYPE: DNA
<213> ORGANISM: Artificial Sequence
<220> FEATURE:
<223> OTHER INFORMATION: degenerate primer
<220> FEATURE:
<221> NAME/KEY: misc_feature
<222> LOCATION: 3, 6
<223> OTHER INFORMATION: n = inosine

<400> SEQUENCE: 47
aynacnckrt crttwac                                                    17

<210> SEQ ID NO 48
<211> LENGTH: 37
<212> TYPE: DNA
<213> ORGANISM: Artificial Sequence
<220> FEATURE:
<223> OTHER INFORMATION: primer

<400> SEQUENCE: 48
cgggagatct cagcaatggg cgtctctgct gttctac                              37

<210> SEQ ID NO 49
<211> LENGTH: 7
<212> TYPE: PRT
<213> ORGANISM: Aspergillus niger

<400> SEQUENCE: 49

Arg His Gly Ala Arg Tyr Pro
 1               5

<210> SEQ ID NO 50
<211> LENGTH: 7
<212> TYPE: PRT
<213> ORGANISM: Aspergillus niger

<400> SEQUENCE: 50

Arg His Gly Glu Arg Tyr Pro
 1               5
```

```
<210> SEQ ID NO 51
<211> LENGTH: 8
<212> TYPE: PRT
<213> ORGANISM: Aspergillus niger

<400> SEQUENCE: 51

Arg His Gly Ala Arg Tyr Pro Thr
 1               5

<210> SEQ ID NO 52
<211> LENGTH: 7
<212> TYPE: PRT
<213> ORGANISM: Aspergillus niger

<400> SEQUENCE: 52

Phe Thr His Asp Glu Trp Ile
 1               5

<210> SEQ ID NO 53
<211> LENGTH: 7
<212> TYPE: PRT
<213> ORGANISM: Aspergillus niger

<400> SEQUENCE: 53

Phe Thr Gln Asp Glu Trp Val
 1               5
```

TRICHODERMA REESEI PHYTASE ENZYMES, NUCLEIC ACIDS ENCODING SUCH PHYTASE ENZYMES, VECTORS AND HOST CELLS INCORPORATING SAME AND METHODS OF MAKING AND USING SAME The present application is a 35 U.S.C. §371 national filing of PCT/US02/32379 filed Oct. 9, 2002, which claims priority to U.S. Provisional Patent Application Ser. No. 60/339,475 filed Oct. 26, 2001 now expired, the contents of which are incorporated herein by reference in its entirety.

FIELD OF THE INVENTION

The present invention relates to phytase from *Trichoderma reesei*, nucleic acid sequences encoding phytase, as well as the production of *T. reesei* phytase and its use.

REFERENCES al-Batshan et al., Poultry Science 73(10): 1590-1596 (1994).

Altschul, S. F., Gish, W., Miller, W., Myers, E. W. & Lipman, D. J. (1990) "Basic local alignment search tool." J. Mol. Biol. 215: 403-410.

Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25: 3389-3402.

Aplin and Wriston, Crit. Rev. Biochem., pp. 259-306 (1981).

ASC Symposium Series 580, "Carbohydrate Modifications in Antisense Research", Chapters 2, 3, 6 and 7, Ed. Y. S. Sanghui and P. Dan Cook.

Ausubel et al. (eds.) (1995) Current Protocols In Molecular Biology, 3rd edition, John Wiley & Sons, Inc.

Baker et al., U.S. Pat. No. 5,571,706 (1996).

Beaucage et al. (1993) Tetrahedron 49(10): 1925.

Beijersbergen et al., U.S. Pat. No. 6,255,115 (2001)

Benner, Steven A., U.S. Pat. No. 5,216,141 (1993).

Bennett & Lasure, More Gene Manipulations in Fungi, Academic Press, San Diego, pp. 70-76 (1991).

Benton, W. and Davis, R., 1977, Science 196: 180.

Berger and Kimmel, (1987), Guide to Molecular Cloning Techniques, Methods in Enzymology, Vol. 152, Academic Press, San Diego Calif.

Birnboim, H. C. and Doly, J. (1979). Nucleic Acids Research 7:1513-23.

Botstein, D. and Shortle, D. (1985) Science 229:1193-1201.

Bowen et al., U.S. Pat. No. 5,736,369 (1998).

Bremel et al., U.S. Pat. No. 6,291,740 (2001).

Bremel et al., U.S. Pat. No. 6,080,912 (2000).

Brisson et al (1984) Nature 310:511-514.

Briu et al. (1989) J. Am. Chem. Soc. 111:2321.

Broglie et al (1984) Science 224:838-843).

Cadwell, R. C. and Joyce, G. F., 1992, PCR Methods Applic. 2:28-33.

Canadian Journal of Animal Science 75(3):439-444 (1995).

Committee on Food Chemicals Codex, Institute of Medicine, *Food Chemicals Codex,* 4th Edition, National Academy Press, Washington, D.C., 1996.

Carlsson et al., Nature 380:207 (1996).

Clark, H. Fred, U.S. Pat. No. 5,610,049 (1997).

Conklin et al., U.S. Pat. No. 5,750,386 (1998).

Cook et al., U.S. Pat. No. 5,637,684 (1997).

Coruzzi et al (1984) EMBO J. 3:1671-1680.

Creighton, T. E., Proteins: Structure and Molecular Properties, W. H. Freeman & Co., San Francisco, pp. 79-86 (1983)

Cromwell, G. L. T., T. S. Stahly, R. D. Coffey, H. J. Monegue, and J. H. Randolph. 1993. Efficacy of phytase in improving bioavailability of phosphorus in soybean and corn-soybean meal diets for pigs. J. Anim. Sci. 71:1831.

Damron et al., Poultry Science 74(5): 784-787 (1995).

Dayhoff, M. O., Schwartz, R. M. & Orcutt, B. C. (1978) "A model of evolutionary change in proteins." In "Atlas of Protein Sequence and Structure, vol. 5, suppl. 3." M. O. Dayhoff (ed.), pp. 345-352, Natl. Biomed. Res. Found., Washington, D.C. Deutscher, Methods in Enzymology, 182 (1990).

DeBoer et al, U.S. Pat. No. 6,066,725 (2000).

De Clercq et al., U.S. Pat. No. 5,589,615 (1996).

De Mesmaeker et al., U.S. Pat. No. 5,602,240 (1997).

De Mesmaeker et al., Bioorganic & Medicinal Chem. Left. 4:395 (1994).

Denpcy et al., Proc. Natl. Acad. Sci. USA 92:6097 (1995).

Devlin, Robert H., U.S. Pat. No. 5,998,697 (1999).

Dieffenbach C W and Dveksler G S, 1995, PCR Primer, a Laboratory Manual, Cold Spring Harbor Press, Plainview N.Y.

Eckert, K. A. and Kunkel, T. A., 1991, PCR Methods Applic. 1:17-24.

Eckstein, Oligonucleotides and Analogues: A Practical Approach, Oxford University Press.

Edge et al., Anal. Biochem., 118:131 (1981).

Egholm (1992) J. Am. Chem. Soc. 114:1895.

Ehrlich, K. C., Montalbano, B. G., Mullaney, E. J., Dischinger Jnr., H. C. & Ullah, A. H. J. (1993). Identification and cloning of a second phytase gene (phy B) from *Aspergillus niger* (ficum). Biochemical and Biophysical Research Communications 195, 53-57.

Elander, R. P., Microbial screening, Selection and Strain Improvement, in Basic Biotechnology, J. Bullock and B. Kristiansen Eds., Academic Press, New York, 1987, 217.

Evan et al., Molecular and Cellular Biology, 5:3610-3616 (1985).

Field et al., Mol. Cell. Biol., 8:2159-2165 (1988).

Finkelstein, D B 1992 Transformation. In Biotechnology of Filamentous Fungi. Technology and Products (eds by Finkelstein & Bill) 113-156.

Fiske, C. H. and SubbaRow, Y. (1925). Journal of Biological Chemistry 66:375-392.

Fungaro et al. (1995) Transformation of *Aspergillus nidulans* by microprojection bombardment on intact conidia, FEMS Microbiology Letters 125 293-298.

Gelvin et al., J. Bacteriol. 172(3): 1600-1608 (1990).

Gish, W. & States, D. J. (1993) "Identification of protein coding regions by database similarity search." Nature Genet. 3:266-272.

Glover, D M and Hames, B D (Eds.), DNA Cloning: A Practical Approach, Vols 1 and 2, Second Edition.

Glover, D M and Hames, B D (Eds.), 1995, DNA Cloning 1: A Practical Approach, Oxford University Press, Oxford).

Glover, D M and Hames, B D (Eds.), 1995, DNA Cloning 2: A Practical Approach, Oxford University Press, Oxford).

Groot et al. (1998) *Agrobacterium tumefaciens*-mediated transformation of filamentous fungi, Nature Biotechnology 16 839-842.

Grunstein, M. and Hogness, D., 1975, Proc. Natl. Acad. Sci. USA 72:3961.

Hakimuddin, et al., Arch. Biochem. Biophys., 259:52 (1987).

Hale & Marham, THE HARPER COLLINS DICTIONARY OF BIOLOGY, Harper Perennial, N.Y. (1991).

Henikoff & Henikoff, Proc. Natl. Acad. Sci. USA 89:10915(1989).

Hershey et al., U.S. Pat. No. 5,268,526 (1993).

Higgins D. G., Bleasby A. J., Fuchs R. (1992) CLUSTAL V: improved software for multiple sequence alignment. Comput. Appl. Biosci. 8:189-191.

Hobbs S or Murry L E (1992) in McGraw Hill Yearbook of Science and Technology, McGraw Hill, New York, N.Y., pp 191-196.

Hodges et al., U.S. Pat. No. 5,677,175 (1997).

Hopp et al., BioTechnology, 6:1204-1210 (1988).

Houdebine et al., U.S. Pat. No. 6,268,545 (2001).

Jaynes et al., U.S. Pat. No. 5,597,945 (1997).

Jeffs et al., J. Biomolecular NMR 34:17 (1994).

Jenkins et al., Chem. Soc. Rev. (1995) pp 169-176.

Jeroch et al., Bodenkultur Vo. 45(4): 361-368 (1994).

Karatzas et al., U.S. Pat. No. 5,907,080 (1999).

Karlin & Altschul, Proc. Nat'l. Acad. Sci. USA 90:5873-5787 (1993).

Kerovuo, J., Lauraeus, M., Nurminen, P., Kalkkinen, N., Apajalahti, J. (1988) Isolation, characterization and molecular gene cloning, and sequencing of a novel phytase from *Bacillus subtilis*. Appl. Environ. Micro., 64, 6, 2079-2085.

Kiedrowski et al., Angew. Chem. Intl. Ed. English 30:423 (1991).

Kornegay, E. T., D. M. Denbow, Z. Yi., and V. Ravindran. 1996. Response of broilers to graded levels of Natuphosâ phytase added to corn-soybean meal-based diets containing three levels of nonphytate phosphorus. Br. J. Nutr.

Lebrun et al., U.S. Pat. No. 5,510,471 (1996).

Letsinger, J. Org. Chem. 35:3800 (1970).

Letsinger et al., Nucleoside & Nucleotide 13:1597 (1994).

Letsinger et al. (1988) J. Am. Chem. Soc. 110:4470.

Letsinger et al. (1986) Nucl. Acids Res. 14:3487.

Leung, D. W., Chen, E., and Goeddel, D. V., 1989, Technique 1:11-15.

Lubon et al., U.S. Pat. No. 6,262,336 (2001).

Lundquist et al., U.S. Pat. No. 5,780,708 (1998).

Lundquist et al., U.S. Pat. No. 5,538,880 (1996);

Lutz-Freyermuth et al., Proc. Natl. Acad. Sci. USA, 87:6393-6397 (1990).

Madden, T. L., Tatusov, R. L. & Zhang, J. (1996) "Applications of network BLAST server" Meth. Enzymol. 266:131-141.

Mag et al. (1991) Nucleic Acids Res. 19:1437.

Martin et al., Science, 255:192-194 (1992).

Meier et al. (1992) Chem. Int. Ed. Engl. 31:1008.

The Merck Veterinary Manual (Seventh Edition, Merck & Co., Inc., Rahway, N.J., USA, 1991, page 1268).

Myers, R. M., Lerman, L. S., and Maniatis, T., 1985, Science 229:242-247.

Mitchell, D. B., Vogel, K., Weimann, B. J., Pasamontes, L. and van Loon, A. P., Microbiology 143 (Pt 1), 245-252 (1997)).

Moloney et al., U.S. Pat. No. 5,750,871 (1998).

Mullis, Kary B., U.S. Pat. No. 4,683,202 (1990).

Needleman & Wunsch, J. Mol. Biol. 48:443 (1970).

Nielsen (1993) Nature, 365:566.

Oakley et al., Gene 61(3): 385-99 (1987).

Paborsky et al., Protein Engineering, 3(6): 547-553 (1990).

Pasamontes, L., Haiker, M., Henriquez-Huecas, M., Mitchell, D. B. and van Loon, A. P., Cloning of the phytases from *Emericella nidulans* and the thermophilic fungus *Talaromyces thermophilus*, Biochim. Biophys. Acta 1353 (3), 217-223 (1997).

Pasamontes, L., Haiker, M., Wyss, M., Tessier, M. and van Loon, A. P., Gene cloning, purification, and characterization of a heat-stable phytase from the fungus *Aspergillus fumigatus*, Appl. Environ. Microbiol. 63 (5), 1696-1700 (1997).

Pauwels et al. (1986) Chemica Scripta 26:141.

Pearson & Lipman, Proc. Nat'l. Acad. Sci. USA 85:2444 (1988).

Piedrahita et al., U.S. Pat. No. 6,271,436 (2001).

Piddington, C. S., Houston, C. S., Paloheimo, M., Cantrell, M., Miettinen-Oinonen, A., Nevalainen, H. & Rambosek, J. (1993). The cloning and sequencing of the genes encoding phytase (PhyA) and pH 2.5-optimum acid phosphatase (aph) from *Aspergillus niger* var. *awamori*. Gene 133, 55-62.

Powar, V. K. and Jagannathan V., (1982) J. Bacteriology, 151 (3), 1102-1108.

Rawls, C & E News Jun. 2, 1997 page 35.

Roland et al., Poultry Science, 75(1): 62-68 (1996).

Sambrook, J., Fritsch, E. F. and Maniatis, T. (1989). Molecular Cloning—A Laboratory Manual, $2^{nd}$ Ed. Cold Spring Harbour Press.

Sambrook et al. (2001). Molecular Cloning, A Laboratory Manual, 3d Ed., Cold Spring Harbor Laboratory Press, Cold Spring Harbor, N.Y.

Sanchez, O. and J. Aguirre. 1996. Efficient transformation of *Aspergillus nidulans* by electroporation of germinated conidia. Fungal Genetics Newsletter 43:48-51.

Sanger, F., Nilken, S. and Coulson, A. R. (1977). Proc. Nat'l. Acad. Sci. USA, 74:5463-5467.

Sanghvi et al. U.S. Pat. No. 5,386,023 (1995)

Sawai et al. (1984) Chem. Lett. 805.

Schwartz, R. M. & Dayhoff, M. O. (1978) "Matrices for detecting distant relationships." In "Atlas of Protein Sequence and Structure, vol. 5, suppl. 3." M. O. Dayhoff (ed.), pp. 353-358, Natl. Biomed. Res. Found., Washington, D.C.

Scopes, Protein Purification: Principles and Practice, Springer-Verlag, New York (1982).

Shimizu, M., (1992) Biosci. Biotech. Biochem., 56-(8), 1266-1269.

Shimizu, M., Japanese Patent Application 6-38745 (1994).

Singleton, et al., DICTIONARY OF MICROBIOLOGY AND MOLECULAR BIOLOGY, 2D ED., John Wiley and Sons, New York (1994).

Skinner et al., J. Biol. Chem., 266:15163-15166 (1991).

Smith & Waterman, Adv. Appl. Math. 2:482 (1981).

Somers et al., U.S. Pat. No. 5,773,269 (1998).

Sprinzl et al. (1977) Eur. J. Biochem. 81:579.

Summerton et al., U.S. Pat. No. 5,235,033 (1993).

Summerton et al., U.S. Pat. No. 5,034,506 (1991).

Takamatsu et al (1987) EMBO J. 6:307-311.

Thotakura et al., Meth. Enzymol., 138:350 (1987).

T'so et al., U.S. Pat. No. 4,469,863 (1984).

Ullah, H. J. and Gibson, D. M., Preparative Biochemistry, 17 (1) (1987), 63-91.

van Gorcom, Robert Franciscus Maria; van Hartingsveldt, Willem; van Paridon, Peter Andreas; Veenstra, Annemarie Eveline; Luiten, Rudolf Gijsbertus Marie; Selten, Gerardus Cornelis Maria; EP 420 358 (1991).

van Hartingsveldt, W., van Zeijl, C. M. J., Harteveld, G. M., Gouka, R. J., Suykerbuyk, M. E. G., Luiten, R. G. M., van Paridon, P. A., Selten, C. G. M., Veenstra, A. E., van Gorcom, R. F. M. & van den Hondel, C. A. J. J. (1993). Cloning, characterization and over expression of the phytase-encoding gene (PhyA) of *Aspergillus niger*. Gene 127:87-94.

Van Loon, A. and Mitchell, D.; EP 684 313 (1995).

Weber, K. L. et al., Biotechniques 25(3): 415-9 (1998).

Weidner, G., d'Enfert, C., Koch, A., Mol, P., and Brakhage, A. A. (1998) Development of a homologous transformation system for the human pathogenic fungus *Aspergillus fumigatus* based on the pyrG gene encoding orotidine monophosphate decarboxylase. Current Genet. 33:378-385.

Weissbach and Weissbach (1988) Methods for Plant Molecular Biology, Academic Press, New York, N.Y., pp 421463.

Wheeler, Mathew B., U.S. Pat. No. 5,942,435 (1999).

Winter J and Sinibaldi R M (1991) Results Probl Cell Differ 17:85-105.

Yau, Eric K., U.S. Pat. No. 5,644,048 (1997).

Yamada et al., Agr. Biol. Chem., 32 (10) (1968), 1275-1282.

BACKGROUND OF THE INVENTION

Phosphorous (P) is an essential element for growth. A substantial amount of the phosphorous found in conventional livestock feed, e.g., cereal grains, oil seed meal, and by-products that originate from seeds, is in the form of phosphate which is covalently bound in a molecule know as phytate (myoinositol hexakisphosphate). The bioavailability of phosphorus in this form is generally quite low for non-ruminants, such as poultry and swine, because they lack digestive enzymes for separating phosphorus from the phytate molecule.

Several important consequences of the inability of non-ruminants to utilize phytate may be noted. For example, expense is incurred when inorganic phosphorus (e.g., dicalcium phosphate, defluorinated phosphate) or animal products (e.g., meat and bone meal, fish meal) are added to meet the animals' nutritional requirements for phosphorus. Additionally, phytate can bind or chelate a number of minerals (e.g., calcium, zinc, iron, magnesium, copper) in the gastrointestinal tract, thereby rendering them unavailable for absorption. Furthermore, most of the phytate present in feed passes through the gastrointestinal tract, elevating the amount of phosphorous in the manure. This leads to an increased ecological phosphorous burden on the environment.

Ruminants, such as cattle, in contrast, readily utilize phytate thanks to an enzyme produced by rumen microorganisms known as phytase. Phytase catalyzes the hydrolysis of phytate to (1) myo-inositol and/or (2) mono-, di-, tri-, tetra- and/or penta-phosphates thereof and (3) inorganic phosphate. Two different types of phytases are known: (1) a so-called 3-phytase (myo-inositol hexaphosphate 3-phosphohydrolase, EC 3.1.3.8) and (2) a so-called 6-phytase (myo-inositol hexaphosphate 6-phosphohydrolase, EC 3.1.3.26). The 3-phytase preferentially hydrolyzes first the ester bond at the 3-position, whereas the 6-phytase preferentially hydrolyzes first the ester bond at the 6-position.

Microbial phytase, as a feed additive, has been found to improve the bioavailability of phytate phosphorous in typical non-ruminant diets (See, e.g., Cromwell, et al, 1993). The result is a decreased need to add inorganic phosphorous to animal feeds, as well as lower phosphorous levels in the excreted manure (See, e.g., Kornegay, et al, 1996).

Despite such advantages, few of the known phytases have gained widespread acceptance in the feed industry. The reasons for this vary from enzyme to enzyme. Typical concerns relate to high manufacture costs and/or poor stability/activity of the enzyme in the environment of the desired application (e.g., the pH/temperature encountered in the processing of feedstuffs, or in the digestive tracts of animals).

It is, thus, generally desirable to discover and develop novel enzymes having good stability and phytase activity for use in connection with animal feed, and to apply advancements in fermentation technology to the production of such enzymes in order to make them commercially viable. It is also desirable to ascertain nucleotide sequences which can be used to produce more efficient genetically engineered organisms capable of expressing such phytases in quantities suitable for industrial production. It is still further desirable to develop a phytase expression system via genetic engineering which will enable the purification and utilization of working quantities of relatively pure enzyme.

SUMMARY OF THE INVENTION

The present invention provides for a purified enzyme having phytase activity which is derived from a microbial source, and preferably from a fungal source, such as, a Trichoderma species, e.g., *T. reesei* (deposit no. ATCC 13631).

The present invention further provides a polynucleotide sequence encoding an enzyme having phytate hydrolyzing activity and comprising a DNA sequence as shown in FIG. 1, 2 or 3 (SEQ ID NOS: 1, 2, or 3); a polynucleotide which encodes the amino acid sequence shown in FIG. 4 or 5 (SEQ ID NOS: 4 or 5); a polynucleotide which encodes a phytase which comprises an amino acid segment which differs from the sequence in FIG. 4 or 5 (SEQ ID NOS: 4 or 5), provided that the polynucleotide encodes a derivative of the phytase specifically described herein; and a polynucleotide which encodes a phytase that comprises an amino acid sequence which differs from the sequence in FIG. 4 or 5 (SEQ ID NOS: 4 or 5), provided that the polynucleotide hybridizes under medium to high stringency conditions with a nucleic acid comprising all or part of the nucleic acid sequence in FIG. 1, 2 or 3 (SEQ ID NOS: 1, 2, or 3).

Additionally, the present invention encompasses vectors which include the polynucleotide sequences described above, host cells which have been transformed with such polynucleotides or vectors, fermentation broths comprising such host cells and phytase proteins encoded by such polynucleotides which are expressed by the host cells. Preferably, the polynucleotide of the invention is in purified or isolated form and is used to prepare a transformed host cell capable of producing the encoded protein product thereof. Additionally, polypeptides which are the expression product of the polynucleotide sequences described above are within the scope of the present invention.

In one embodiment, the present invention provides an isolated or purified polynucleotide derived from a fungal source of the genus *Trichoderma*, which polynucleotide comprises a nucleotide sequence encoding an enzyme having phytase activity. The fungal source can be, for example, from *Trichoderma reesei*.

According to one embodiment, the polynucleotide encodes a phytate-hydrolyzing enzyme including an amino acid sequence having at least 50% identity, preferably at least 55% identity, more preferably at least 60% identity, still more preferably at least 65% identity, yet more preferably at least 70% identity, even more preferably at least 75% identity, again more preferably at least 80% identity, yet again more preferably at least 85% identity, and most preferably at least 90% up to about 100% identity to an amino acid sequence as disclosed in FIG. 4 or 5 (SEQ ID NOS: 4 or 5).

One embodiment of the present invention provides an isolated polynucleotide comprising a nucleotide sequence (i) having at least 50% identity, preferably at least 55% identity, more preferably at least 60% identity, still more preferably at least 65% identity, yet more preferably at least 70% identity, even more preferably at least 75% identity, again more preferably at least 80% identity, yet again more preferably at least 85% identity, and most preferably at least 90%, more preferably at least 95% up to about 100% identity to a nucleotide sequence as disclosed in FIG. 1, 2 or 3 (SEQ ID NOS: 1, 2, or 3) or (ii) being capable of hybridizing to a probe derived from the nucleotide sequence disclosed in FIG. 1, 2 or 3 (SEQ ID NOS: 1, 2, or 3) under conditions of intermediate to high stringency, or (iii) being complementary to the nucleotide sequence disclosed in FIG. 1, 2 or 3 (SEQ ID NOS: 1, 2, or 3).

Another aspect of the present invention provides an isolated polynucleotide encoding an enzyme having phytase activity, wherein the enzyme is derived from a Trichoderma source. The source can be, for example, *Trichoderma reesei*.

Yet a further aspect of the present invention provides an expression construct including a polynucleotide sequence (i) having at least 50% identity, preferably at least 55% identity, more preferably at least 60% identity, still more preferably at least 65% identity, yet more preferably at least 70% identity, even more preferably at least 75% identity, again more preferably at least 80% identity, yet again more preferably at least 85% identity, and most preferably at least 90% up to about 100% identity to a nucleotide sequence as disclosed in FIG. 1, 2 or 3 (SEQ ID NOS: 1, 2, or 3), or (ii) being capable of hybridizing to a probe derived from the nucleotide sequence disclosed in FIG. 1, 2 or 3 (SEQ ID NOS: 1, 2, or 3) under conditions of medium to high stringency, or (iii) being complementary to the nucleotide sequence disclosed in FIG. 1, 2 or 3 (SEQ ID NOS: 1, 2, or 3). Also provided are a vector (e.g., a plasmid) including such expression construct, and a host cell (such as a *Trichoderma*, e.g., *Tricoderma reesei*, or an *Aspergillus*, e.g., *Aspergillus niger* or *Aspergillus nidulans*) transformed with such a vector.

In another of its aspects, the present invention provides a probe for use in detecting nucleic acid sequences coding for an enzyme having phytase activity derived from a microbial source, comprising: a nucleotide sequence (i) having at least 50% identity, preferably at least 55% identity, more preferably at least 60% identity, still more preferably at least 65% identity, yet more preferably at least 70% identity, even more preferably at least 75% identity, again more preferably at least 80% identity, yet again more preferably at least 85% identity, and most preferably at least 90% up to about 100% identity to a nucleotide sequence as disclosed in FIG. 1, 2 or 3 (SEQ ID NOS: 1, 2, or 3), or (ii) being capable of hybridizing to a polynucleotide including a sequence as disclosed in FIG. 1, 2 or 3 (SEQ ID NOS: 1, 2, or 3) under conditions of medium to high stringency, or (iii) being complementary to the nucleotide sequence disclosed in FIG. 1, 2 or 3. In a preferred embodiment, the probe is derived from the sequence disclosed in FIG. 1, 2 or 3 (SEQ ID NOS: 1, 2, or 3).

In one embodiment, the microbial source is a fungal source, e.g., a *Trichoderma* species, such as *Trichoderma reesei*.

The present invention additionally provides a food or animal feed including an enzyme having phytase activity, wherein the enzyme comprises an amino acid sequence having at least 50% identity, preferably at least 55% identity, more preferably at least 60% identity, still more preferably at least 65% identity, yet more preferably at least 70% identity, even more preferably at least 75% identity, again more preferably at least 80% identity, yet again more preferably at least 85% identity, and most preferably at least 90% up to about 100% identity to an amino acid sequence as disclosed in FIG. 4 or 5 (SEQ ID NOS: 4 or 5).

The present invention provides food or animal feed including an enzyme having phytase activity, wherein the enzyme is derived from a fungal source such as *Trichoderma reesei*.

One aspect of the present invention provides an isolated phytase enzyme wherein the enzyme is obtained from a *T. reesei* and has the following physicochemical properties: (1) Molecular weight: between about 55 and 61 kDa (non-glycosylated), preferably between about 57 and 59 kDa; and (2) Substrate: phytate. In one embodiment, the isolated phytase enzyme may be further characterized by having an isoelectric point of about 6.3.

Another aspect of the present invention provides a method of producing an enzyme having phytase activity, comprising:

(a) providing a host cell transformed with an expression vector comprising a polynucleotide as described herein;

(b) cultivating the transformed host cell under conditions suitable for the host cell to produce the phytase; and (c) recovering the phytase.

According to a preferred embodiment, the host cell is a *Trichoderma* species such as *T. reesei*. In another embodiment, the host cell is an *Aspergillus* species, such as *A. niger* or *A. nidulans*.

In one embodiment, the host cell is a plant cell. In this embodiment, cells or entire transformed plants may be grown and used.

Another aspect of the present invention provides a method of producing an enzyme having phytase activity, comprising:

(a) providing a host cell transformed with an expression vector comprising a polynucleotide as described herein;

(b) cultivating the transformed host cell under conditions suitable for the host cell to produce the phytase. The transformed cells, as well as organisms grown from such cells, may be used without further isolation of the enzyme.

In another aspect, the invention provides a purified enzyme having phytase activity, produced by the method described above.

In yet another of its aspects, the present invention provides a method of separating phosphorous from phytate, comprising the step of treating the phytate with an enzyme comprising an amino acid sequence having at least 50% identity, preferably at least 55% identity, more preferably at least 60% identity, still more preferably at least 65% identity, yet more preferably at least 70% identity, even more preferably at least 75% identity, again more preferably at least 80% identity, yet again more preferably at least 85% identity, and most preferably at least 90% up to about 100% identity to an amino acid sequence as disclosed in FIG. 4 or 5 (SEQ ID NOS: 4 or 5).

The present invention further provides a method of separating phosphorous from phytate, comprising the step of treating the phytate with an enzyme as defined above.

The present invention further provides a vector (e.g., plasmid) including such an expression construct, as well as a host cell (e.g., *Trichoderma reesei*) transformed with a vector as described above.

In one embodiment, the microbial source is a fungal source, e.g., a *Trichoderma* species, such as *T. reesei*.

As will be appreciated, an advantage of the present invention is that a polynucleotide has been isolated which provides the capability of isolating further polynucleotides which encode proteins having phytase activity.

Another advantage of the present invention is that, by virtue of providing a polynucleotide encoding a protein having phytase activity, it is possible to produce, through recombinant means, a host cell which is capable of producing the protein having phytase activity in relatively large quantities.

Yet another advantage of the present invention is that commercial application of proteins having phytase activity is made practical. For example, the present invention provides animal feed incorporating the phytase described herein.

Other objects and advantages of the present invention will become apparent from the following detailed specification.

BRIEF DESCRIPTION OF THE DRAWINGS

FIG. 1 shows a nucleic acid sequence (SEQ ID NO: 1) corresponding to 2220 base pairs of a gene encoding a phytase hydrolyzing enzyme derived from *Trichoderma reesei*. The start (ATG) and stop (TGA) codons are underlined, each defining an open reading.

FIG. 2 shows the nucleic acid sequence (SEQ ID NO: 2) of an open reading frame in the gene shown in FIG. 1.

FIG. 3 shows the nucleic acid sequence (SEQ ID NO: 3) of an alternate open reading frame in the gene shown in FIG. 1.

FIG. 4 shows the deduced amino acid sequence of a *T. reesei* phytase enzyme (SEQ ID NO: 4) encoded by the nucleic acid sequence of FIG. 1 or 2. This enzyme has 524 amino acids, motecular weight of about 57-59 kiloDaltons (unglycosylated) and isoelectric point of about 6.3.

FIG. 5 shows an amino acid sequence of a *T. reesei* phytase enzyme (SEQ ID NO: 5) encoded by the nucleic acid sequence of FIG. 1 or 3.

FIG. 6 shows a BLAST alignment (SEQ ID NO: 8), as further described below, of the amino acid sequence of the phytase enzyme (SEQ ID NO: 6) of FIG. 4 and a phytase from *Emericella nidulans* (SEQ ID NO: 7). The identified portions of the two sequences show 48% identity, 63% similarity.

FIG. 7 shows a BLAST alignment (SEQ ID NO: 11) of the amino acid sequence of the phytase enzyme of FIG. 4 (SEQ ID NO: 9) and a phytase from *Aspergillus awamori* (SEQ ID NO: 10). The identified portions of the two sequences show 47% identity, 64% similarity.

FIG. 8 shows a BLAST alignment (SEQ ID NO: 14) of the amino acid sequence of the phytase enzyme of FIG. 5 (SEQ ID NO: 12) and a phytase from *Aspergillus niger* (SEQ ID NO: 13). The identified portions of the two sequences show 46% identity, 63% similarity.

DETAILED DESCRIPTION OF THE INVENTION

I. Definitions

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acid sequences are written left to right in 5' to 3' orientation; amino acid sequences are written left to right in amino to carboxy orientation, respectively. The headings provided herein are not limitations of the various aspects or embodiments of the invention which can be had by reference to the specification as a whole. Accordingly, the terms defined immediately below are more fully defined by reference to the specification as a whole.

"Protein", as used herein, includes proteins, polypeptides, and peptides. As will be appreciated by those in the art, the nucleic acid sequences of the invention, as defined below and further described herein, can be used to generate protein sequences.

As used herein, the term "phytase" or "phytase activity" refers to a protein or polypeptide which is capable of catalyzing the hydrolysis of phytate to (1) myo-inositol and/or (2) mono-, di-, tri-, tetra- and/or penta-phosphates thereof and (3) inorganic phosphate. For example, enzymes having catalytic activity as defined in Enzyme Commission EC number 3.1.3.8, or EC number 3.1.3.26.

In the broadest sense, by "nucleic acid sequence", "polynucleotide" or "oligonucleotide" or grammatical equivalents herein means at least two nucleotides covalently linked together. A nucleic acid sequence of the present invention will generally contain phosphodiester bonds, although in some cases, as outlined below, nucleic acid sequence analogs are included that may have alternate backbones, comprising, for example, phosphoramidate (Beaucage et al., Tetrahedron 49(10): 1925 (1993) and references therein; Letsinger, J. Org. Chem. 35: 3800 (1970); Sprinzl et al., Eur. J. Biochem. 81: 579 (1977); Letsinger et al., Nucl. Acids Res. 14: 3487 (1986); Sawai et al, Chem. Lett. 805 (1984), Letsinger et al., J. Am. Chem. Soc. 110: 4470 (1988); and Pauwels et al., Chemica Scripta 26: 141 91986)), phosphorothioate (Mag et al., Nucleic Acids Res. 19: 1437 (1991); and U.S. Pat. No. 5,644,048), phosphorodithioate (Briu et al., J. Am. Chem. Soc. 111: 2321 (1989)), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114: 1895 (1992); Meier et al., Chem. Int. Ed. Engl. 31: 1008 (1992); Nielsen, Nature, 365: 566 (1993); Carlsson et al., Nature 380: 207 (1996), all of which are incorporated by reference). Other analog nucleic acids include those with positive backbones (Denpcy et al., Proc. Natl. Acad. Sci. USA 92: 6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30: 423 (1991); Letsinger et al., J. Am. Chem. Soc. 110: 4470 (1988); Letsinger et al., Nucleoside & Nucleotide 13: 1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4: 395 (1994); Jeffs et al., J. Biomolecular NMR 34: 17 (1994); Tetrahedron Lett. 37: 743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done for a variety of reasons, for example to increase the stability and half-life of such molecules in physiological or food processing environments.

As will be appreciated by those in the art, all of these nucleic acid analogs may find use in the present invention. In addition, mixtures of naturally occurring nucleic acids and analogs can be made; alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4☐C drop in Tm for an internal mismatch. With the non-ionic PNA backbone, the drop is closer to 7-9☐ C. Similarly, due to their non-ionic nature, hybridization of the bases attached to these backbones is relatively insensitive to salt concentration. In addition, PNAs are not degraded by cellular enzymes, and thus can be more stable.

The nucleic acid sequences may be single stranded or double stranded, as specified, or contain portions of both double stranded or single stranded sequence. As will be appreciated by those in the art, the depiction of a single strand ("Watson") also defines the sequence of the other strand ("Crick"); thus the sequences described herein also includes the complement of the sequence. The nucleic acid sequence may be DNA, both genomic and cDNA, RNA or a hybrid, where the nucleic acid sequence contains any combination of deoxyribo- and ribo-nucleotides, and any combination of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid sequence, each containing a base, are referred to herein as a nucleoside.

The term "identical" in the context of two nucleic acid sequences or polypeptide sequences refers to the residues in the two sequences that are the same when aligned for maximum correspondence, as measured using one of the following sequence comparison or analysis algorithms.

"Optimal alignment" is defined as an alignment giving the highest percent identity score. Such alignment can be performed using a variety of commercially available sequence analysis programs, such as the local alignment program LALIGN using a ktup of 1, default parameters and the default PAM. A preferred alignment is the pairwise alignment performed using the CLUSTAL-W program in MACVECTOR, operated in "slow" alignment mode using default parameters, including an open gap penalty of 10.0, an extend gap penalty of 0.1, and a BLOSUM30 similarity matrix. If a gap needs to be inserted into a first sequence to optimally align it with a second sequence, the percent identity is calculated using only the residues that are paired with a corresponding amino acid residue (i.e., the calculation does not consider residues in the second sequences that are in the "gap" of the first sequence).

Optimal alignment of sequences for comparison can also be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical.

Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in "Atlas of Protein Sequence and Structure", M. O. Dayhoff ed., * 5 Suppl. 3: 353-358, National Biomedical Research Foundation, Washington, D.C., which adapts the local homology algorithm of Smith and Waterman (1981) Advances in Appl. Math. 2: 482-489 for peptide analysis.

Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above.

An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M'S, N'-4, and a comparison of both strands.

The BLAST algorithm then performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid sequence is considered similar to a phytase nucleic acid sequence of this invention if the smallest sum probability in a comparison of the test nucleic acid sequence to a phytase nucleic acid sequence is less than about 0.1, more preferably less than about 0.01, and most preferably less than about 0.001. Where the test nucleic acid sequence encodes a phytase polypeptide, it is considered similar to a specified phytase nucleic acid sequence if the comparison results in a smallest sum probability of less than about 0.5, and more preferably less than about 0.2.

The phrase "substantially identical" in the context of two nucleic acid sequences or polypeptides thus typically means that a polynucleotide or polypeptide comprises a sequence that has at least 60% sequence identity, preferably at least 80%, more preferably at least 90% and most preferably at least 95%, compared to a reference sequence using the programs described above (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

"Hybridization" includes any process by which a strand of a nucleic acid sequence joins with a second nucleic acid sequence strand through base-pairing. Thus, strictly speaking, the term refers to the ability of a target sequence to bind to a test sequence, or vice-versa.

"Hybridization conditions" are typically classified by degree of "stringency" of the conditions under which hybridization is measured. The degree of stringency can be based, for example, on the calculated (estimated) melting temperature (Tm) of the nucleic acid sequence binding complex or probe. Calculation of Tm is well known in the art (see, e.g. page 9.50-9.51 of Sambrook (1989), below). For example, "maximum stringency" typically occurs at about Tm-5_C (5_below the Tm of the probe); "high stringency" at about 5-10_below the Tm; "intermediate stringency" at about 10-20_below the Tm of the probe; and "low stringency" at about 20-25_below the Tm. In general, hybridization conditions are carried out under high ionic strength conditions, for example, using 6×SSC or 6×SSPE. Under high stringency conditions, hybridization is followed by two washes with low salt solution, for example 0.5×SSC, at the calculated temperature. Under medium stringency conditions, hybridization is followed by two washes with medium salt solution, for example 2×SSC. Under low stringency conditions, hybridization is followed by two washes with high salt solution, for example 6×SSC. Functionally, maximum stringency conditions may be used to identify nucleic acid sequences having strict identity or near-strict identity with the hybridization probe; while high stringency conditions are used to identify nucleic acid sequences having about 80% or more sequence identity with the probe.

For applications requiring high selectivity, one will typically desire to employ relatively stringent conditions to form the hybrids, e.g., one will select relatively high temperature conditions. Hybridization conditions, including moderate stringency and high stringency, are provided in Sambrook et al., Molecular Cloning: A Laboratory Manual, Second Edition, Cold Spring Harbor Press (1989); Sambrook et al., Molecular Cloning, A Laboratory Manual, 3d Ed., Cold Spring Harbor Laboratory Press, Cold Spring Harbor, N.Y. (2001), incorporated herein by reference.

The term "complementary", in the context of a nucleic acid sequence, means a nucleic acid sequence having a sequence relationship to a second nucleic acid sequence such that there is perfect alignment of Watson-Crick base pairs along the entire length of both nucleic acid sequences.

The term "isolated" or "purified" means that a material is removed from its original environment (e.g., the natural environment if it is naturally occurring). For example, the material is said to be "purified" when it is present in a particular composition in a higher or lower concentration than exists in a naturally occurring or wild type organism or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector, and/or such polynucleotides or polypeptides could be part of a composition, and still be isolated in that such vector or composition is not part of its natural environment. A nucleic acid sequence or protein is said to be purified, for example, if it gives rise to essentially one band in an electrophoretic gel.

The present invention provides for the production of recombinant nucleic acids and proteins. By "recombinant" and grammatical equivalents thereof is meant produced using recombinant technology, whereby novel nucleic acids are made (recombinant nucleic acids) and proteins are produced therefrom (recombinant proteins). Such techniques are well known in the art and many are described in great detail herein. In a broad sense, a recombinant nucleic acid sequence may be any nucleic acid sequence not in its naturally occurring form, whether it be a sequence isolated from its naturally occurring adjoining sequence, or combined with other sequences with which it was not joined in nature to form a new nucleic acid sequence, such as in a vector. Recombinant nucleic acid sequences also includes those that are produced from recombinant nucleic acid sequences, for example complementary sequences made through polymerization, additional copies made though replication, or RNA transcribed from recombinant DNA. Recombinant protein is protein produced by translation of recombinant nucleic acid sequences.

As used herein in referring to phytate hydrolyzing enzymes (phytases), the term "derived from" is intended not only to indicate a phytase produced or producible by a strain of the organism in question, but also a phytase encoded by a DNA sequence isolated from such strain and produced in a host organism containing such DNA sequence. Additionally, the term is intended to indicate a phytase which is encoded by a DNA sequence of synthetic and/or cDNA origin and which has the identifying characteristics of the phytase in question. To exemplify, "phytases derived from *Trichoderma*" refers to those enzymes having phytase activity which are naturally-produced by *Trichoderma*, as well as to phytases like those produced by *Trichoderma* sources but which through the use of genetic engineering techniques are produced by non-*Trichoderma* organisms transformed with a nucleic acid sequence encoding said phytases.

The present invention encompasses phytate hydrolyzing enzymes that are equivalent to those that are derived from the particular microbial strain mentioned. Being "equivalent," in this context, means that the phytate hydrolyzing enzymes are encoded by a polynucleotide capable of hybridizing to the polynucleotide having the sequence as shown in any one of FIGS. 1-3 under conditions of medium to high stringency. Being equivalent means that the phytate hydrolyzing enzyme comprises at least 50% identity, preferably at least 55% identity, more preferably at least 60% identity, still more preferably at least 65% identity, yet more preferably at least 70% identity, even more preferably at least 75% identity, again more preferably at least 80% identity, yet again more preferably at least 85% identity, and most preferably at least 90% up to about 100% identity to the phytate hydrolyzing enzyme having the amino acid sequence disclosed in one of FIGS. 4 and 5.

The present invention also encompasses mutants, variants and derivatives of the phytate hydrolyzing enzymes of the present invention as long as the mutant, variant or derivative phytate hydrolyzing enzyme is able to retain at least one characteristic activity of the naturally occurring phytate hydrolyzing enzyme.

As used herein, the term "mutants and variants", when referring to phytate hydrolyzing enzymes, refers to phytate hydrolyzing enzymes obtained by alteration of the naturally occurring amino acid sequence and/or structure thereof, such as by alteration of the DNA nucleotide sequence of the structural gene and/or by direct substitution and/or alteration of the amino acid sequence and/or structure of the phytate hydrolyzing enzyme.

The term "derivative" or "functional derivative" as it relates to phytase is used herein to indicate a derivative of phytase which has the functional characteristics of phytase of the present invention. Functional derivatives of phytase encompass naturally occurring, synthetically or recombinantly produced peptides or peptide fragments, mutants or variants which may have one or more amino acid deletions, insertions or substitutions which have the general characteristics of the phytase of the present invention.

The term "functional derivative" as it relates to nucleic acid sequences encoding phytase is used throughout the specification to indicate a derivative of a nucleic acid sequence which has the functional characteristics of a nucleic acid sequence which encodes phytase. Functional derivatives of a nucleic acid sequence which encode phytase of the present invention encompass naturally occurring, synthetically or recombinantly produced nucleic acid sequences or fragments, mutants or variants thereof which may have one or more nucleic acid deletions, substitutions or insertions and encode phytase characteristic of the present invention. Variants of nucleic acid sequences encoding phytase according to the invention include alleles and variants based on the degeneracy of the genetic code known in the art. Mutants of nucleic acid sequences encoding phytase according to the invention include mutants produced via site-directed mutagenesis techniques (see for example, Botstein, D. and Shortle, D., 1985, Science 229:1193-1201 and Myers, R. M., Lerman, L. S., and Maniatis, T., 1985, Science 229: 242-247), error-prone PCR (see for example, Leung, D. W., Chen, E., and Goeddel, D. V., 1989, Technique 1:11-15; Eckert, K. A. and Kunkel, T. A., 1991, PCR Methods Applic. 1: 17-24; and Cadwell, R. C. and Joyce, G. F., 1992, PCR Methods Applic. 2: 28-33) and/or chemical-induced mutagenesis techniques known in the art (see for example, Elander, R. P., Microbial screening, Selection and Strain Improvement, in Basic Biotechnology, J. Bullock and B. Kristiansen Eds., Academic Press, New York, 1987, 217).

"Expression vector" means a DNA construct comprising a DNA sequence which is operably linked to a suitable control sequence capable of effecting the expression of the DNA in a suitable host. Such control sequences may include a promoter to effect transcription, an optional operator sequence to control such transcription, a sequence encoding suitable ribosome-binding sites on the mRNA, and sequences which control termination of transcription and translation. Different cell types are preferably used with different expression vectors. A preferred promoter for use in *Trichoderma reesei* is cbh1. A preferred promoter for vectors used in *Bacillus subtilis* is the AprE promoter; a preferred promoter used in *E. coli* is the Lac promoter and a preferred promoter used in *Aspergillus niger* is glaA. The vector may be a plasmid, a phage particle, or simply a potential genomic insert. Once transformed into a suitable host, the vector may replicate and function independently of the host genome, or may, under suitable conditions, integrate into the genome itself.

In the present specification, plasmid and vector are sometimes used interchangeably. However, the invention is intended to include other forms of expression vectors which serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage 1, e.g., NM989, and other DNA phages, e.g., M13 and filamentous single stranded DNA phages, yeast plasmids such as the 2 m plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences.

Expression techniques using the expression vectors of the present invention are known in the art and are described generally in, for example, Sambrook et al., Molecular Cloning: A Laboratory Manual, Second Edition, Cold Spring Harbor Press (1989); Sambrook et al., Molecular Cloning, A Laboratory Manual, 3d Ed., Cold Spring Harbor Laboratory Press, Cold Spring Harbor, N.Y. (2001). Often, such expression vectors including the DNA sequences of the invention are transformed into a unicellular host by direct insertion into the genome of a particular species through an integration event (see e.g., Bennett & Lasure, More Gene Manipulations in Fungi, Academic Press, San Diego, pp. 70-76 (1991) and articles cited therein describing targeted genomic insertion in fungal hosts, incorporated herein by reference).

"Host strain" or "host cell" means a suitable host for an expression vector comprising DNA according to the present invention. Host cells useful in the present invention are generally procaryotic or eucaryotic hosts, including any transformable microorganism in which expression can be achieved. For example, host strains can be *Trichoderma reesei, Bacillus subtilis, Escherichia coli, Trichoderma longibrachiatum, Saccharomyces cerevisiae, Aspergillus niger*, and *Aspergillus nidulans*. Host cells are transformed or transfected with vectors constructed using recombinant DNA techniques. Such transformed host cells are capable of both replicating vectors encoding phytase and its variants (mutants) or expressing the desired peptide product.

Examples of appropriate expression hosts include: bacterial cells, such as *E. coli, Streptomyces, Salmonella typhimurium*; fungal cells, such as *Trichoderma, Aspergillus, Fusarium, Chrysosporium* and *Penicillium*; insect cells such as *Drosophila* and *Spodoptera* Sf9; animal cells such as CHO, COS, HEK 293 or Bowes melanoma; plant cells, etc. The selection of an appropriate host is deemed to be within the scope of those skilled in the art from the teachings herein. It should be noted that the invention is not limited by the particular host cells employed.

II. Phytase Enzymes and Nucleic Acid Sequences Encoding Phytase Enzymes

One aspect of the present invention provides proteins or polypeptides which are capable of catalyzing the hydrolysis of phytate and releasing inorganic phosphate; for example, enzymes having catalytic activity as defined in Enzyme Commission EC number 3.1.3.8, or in EC number 3.1.3.26. In one preferred embodiment, the invention provides a so-called 3-phytase. The present invention additionally encompasses polynucleotides (e.g., DNA) which encode such phytate hydrolyzing proteins or polypeptides.

Preferably, the phytase and/or polynucleotides encoding the phytase according to the present invention is derived from a fungus, preferably from an anaerobic fungus or thermophilic fungus and most preferably from *Trichoderma* sp., e.g., *Trichoderma reesei*. Thus, it is contemplated that the phytase or the DNA encoding the phytase according to the invention can be derived from *Absidia* sp.; *Acremonium* sp.; *Actinomycetes* sp.; *Agaricus* sp.; *Anaeromyces* sp.; *Aspergillus* sp., including *A. auculeatus, A. awamori, A. flavus, A. foetidus, A. fumaricus, A. fumigatus, A. nidulans, A. niger, A. oryzae, A. terreus, A. tubigensis* and *A. versicolor*; *Aeurobasidium* sp.; *Cephalosporum* sp.; *Chaetomium* sp.; *Chrysosporium* sp.; *Coprinus* sp.; *Dactyllum* sp.; *Fusarium* sp., including *F. conglomerans, F. decemcellulare, F. javanicum, F. lini, F. oxysporum* and *F. solani*; *Gliocladium* sp.; *Humicola* sp., including *H. insolens* and *H. lanuginosa*; *Mucor* sp.; *Myceliopthora* sp., including *M. thermophila*; *Neurospora* sp., including *N. crassa* and *N. sitophila*; *Neocallimastix* sp.; *Orpinomyces* sp.; *Penicillium* spp; *Phanerochaete* sp.; *Phlebia* sp.; *Piromyces* sp.; *Pseudomonas* sp.; *Rhizopus* sp.; *Schizophyllum* sp.; *Streptomyces* spp; *Trametes* sp.; and *Trichoderma* sp., including *T. reesei, T. longibrachiatum* and *T. viride*; and *Zygorhynchus* sp. Similarly, it is envisioned that a phytase and/or DNA encoding a phytase as described herein may be derived from bacteria such as *Streptomyces* sp., including *S. olivochromogenes*; specifically fiber degrading ruminal bacteria such as *Fibrobacter succinogenes*; and in yeast including *Candida torresii; C. parapsllosis; C. sake; C. zeylanoides; Pichia minuta; Rhodotorula glutinis; R. mucilaginosa*; and *Sporobolomyces holsaticus*.

In one preferred embodiment, the phytase and/or polynucleotides encoding the phytase according to the present invention is/are derived from (i) a grain-spoilage fungus, such as *Penicillium hordei, Penicillium piceum*, or *Penicillium brevi-compactum*; or (ii) an ectomycorrhizal fungus associated with tree roots, e.g., *Laccaria laccata, Laccaria rufus, Paxillus involutus, Hebeloma crustuliniforme, Amanita rubescens*, or *Amanita muscaria*.

According to a preferred embodiment, the phytase and/or polynucleotide encoding the phytase of the present invention is in a purified form, i.e., present in a particular composition in a higher or lower concentration than exists in a naturally occurring or wild type organism or in combination with components not normally present upon expression from a naturally occurring or wild type organism.

The invention encompasses phytate hydrolyzing proteins and peptides comprising at least 50% identity, preferably at least 55% identity, more preferably at least 60% identity, still more preferably at least 65% identity, yet more preferably at least 70% identity, even more preferably at least 75% identity, again more preferably at least 80% identity, yet again more preferably at least 85% identity, and most preferably at least 90% up to about 100% identity to the phytate hydrolyzing enzyme having the amino acid sequence disclosed in FIGS. 4 and 5.

The invention further encompasses polynucleotides, e.g., DNA, which encode phytate hydrolyzing enzymes derived from fungal sources, such as *Trichoderma* sp., which polynucleotides include a sequence having at least 65% identity, at least 70% identity, at least 75% identity, at least 80% identity, at least 85% identity, at least 90% identity and at least 95% identity to the polynucleotide sequence disclosed in any one of FIGS. 1-3, as long as the enzyme encoded by the polynucleotide is capable of catalysing the hydrolysis of phytate and releasing inorganic phosphate. In a preferred embodiment, the polynucleotide encoding the phytate hydrolyzing enzyme has the polynucleotide sequence as shown in any one of FIGS. 1-3, or is capable of hybridizing to the polynucleotide sequence as shown in any one of FIGS. 1-3 or its complement, or is complementary to the polynucleotide sequence as shown in any one of FIGS. 1-3. As will be understood by the skilled artisan, due to the degeneracy of the genetic code, a variety of polynucleotides can encode the phytate hydrolyzing enzyme disclosed in any one of FIGS. 4 and 5. The present invention encompasses all such polynucleotides.

III. Obtaining Polynucleotides Encoding a Phytate Hydrolyzing Enzyme

The nucleic acid sequence encoding a phytate hydrolyzing enzyme may be obtained by standard procedures known in the art from, for example, cloned DNA (e.g., a DNA "library"), by chemical synthesis, by cDNA cloning, by PCR, or by the cloning of genomic DNA, or fragments thereof, purified from a desired cell, such as a fungal species (See, for example, Sambrook et al., 2001, Molecular Cloning, A Laboratory Manual, 3d Ed., Cold Spring Harbor Laboratory Press, Cold Spring Harbor, N.Y.; Glover, D M and Hames, B D (Eds.), 1995, DNA Cloning 1: A Practical Approach and DNA Cloning 2: A Practical Approach, Oxford University Press, Oxford). Nucleic acid sequences derived from genomic DNA may contain regulatory regions in addition to coding regions.

In the molecular cloning of the gene from genomic DNA, DNA fragments are generated, some of which will comprise at least a portion of the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis, PCR and column chromatography.

Once nucleic acid sequence fragments are generated, identification of the specific DNA fragment encoding a phytate hydrolyzing enzyme may be accomplished in a number of ways. For example, a phytate hydrolyzing enzyme encoding gene of the present invention or its specific RNA, or a fragment thereof, such as a probe or primer, may be isolated and labeled and then used in hybridization assays to detect a generated gene. (Benton, W. and Davis, R., 1977, Science 196:180; Grunstein, M. and Hogness, D., 1975, *Proc. Natl. Acad. Sci. USA* 72:3961). Those DNA fragments sharing substantial sequence similarity to the probe will hybridize under medium to high stringency.

The present invention encompasses phytate hydrolyzing enzymes derived from fungal species (esp., *Trichoderma* species) which are identified through nucleic acid sequence hybridization techniques using one of the sequences disclosed in FIGS. 1-3, or a suitable portion or fragment thereof (e.g., at least about 10-15 contiguous nucleotides), as a probe or primer and screening nucleic acid sequences of either genomic or cDNA origin. Nucleic acid sequences encoding phytate hydrolyzing enzymes derived from fungal species and having at least 65% identity to the sequence of one of FIGS. 1-3 or a portion or fragment thereof can be detected by DNA-DNA or DNA-RNA hybridization or amplification using probes, portions or fragments of the disclosed sequences. Accordingly, the present invention provides a method for the detection of a nucleic acid sequence encoding a phytate hydrolyzing enzyme encompassed by the present invention which comprises hybridizing part or all of a nucleic acid sequence of FIG. 1, 2 or 3 with a nucleic acid sequence of either genomic or cDNA origin.

Also included within the scope of the present invention are polynucleotide sequences that are capable of hybridizing to the nucleotide sequence disclosed in FIGS. 1,2 or 3 under conditions of medium to high stringency. In one embodiment, hybridization conditions are based on the melting temperature (Tm) of the nucleic acid sequence binding complex, as taught in Berger and Kimmel (1987, Guide to Molecular Cloning Techniques, Methods in Enzymology, Vol 152, Academic Press, San Diego Calif.) incorporated herein by reference, and confer a defined stringency. In this embodiment, "maximum stringency" typically occurs at about Tm-5_C (5_C below the Tm of the probe); "high stringency" at about 5_C to 10_C below Tm; "medium" or "intermediate stringency" at about 10_C to 20_C below Tm; and "low stringency" at about 20_C to 25_C below Tm. A maximum stringency hybridization can be used to identify or detect identical or near-identical polynucleotide sequences, while an intermediate or low stringency hybridization can be used to identify or detect polynucleotide sequence homologs.

The process of amplification as carried out in polymerase chain reaction (PCR) technologies is described in Dieffenbach C W and G S Dveksler (1995, PCR Primer, a Laboratory Manual, Cold Spring Harbor Press, Plainview N.Y.). A nucleic acid sequence of at least about 10 nucleotides and as many as about 60 nucleotides from the sequences of FIGS. 1, 2 or 3, preferably about 12 to 30 nucleotides, and more preferably about 25 nucleotides can be used as a probe or PCR primer.

A preferred method of isolating a nucleic acid sequence construct of the invention from a cDNA or genomic library is by use of polymerase chain reaction (PCR) using degenerate oligonucleotide probes prepared on the basis of the amino acid sequence of the protein having the amino acid sequence as shown in FIG. 4 or 5. For instance, the PCR may be carried out using the techniques described in U.S. Pat. No. 4,683,202.

In view of the above, it will be appreciated that the polynucleotide sequences provided in FIGS. 1, 2 and 3 are useful for obtaining identical or homologous fragments of polynucleotides from other species, and particularly from fungi (e.g., the grain-spoilage fungi, or the Ectomycorrhizae) which encode enzymes having phytase activity.

IV. Obtaining Derivative or Variant Phytate Hydrolyzing Enzymes

In one embodiment, the phytase proteins are derivative or variant phytase as compared to the wild-type sequence. That is, as outlined more fully below, the derivative phytase peptide will contain at least one amino acid substitution, deletion or insertion, with amino acid substitutions being particularly preferred. The amino acid substitution, insertion or deletion may occur at any residue within the phytase peptide.

Also included in an embodiment of phytase proteins of the present invention are amino acid sequence variants. These variants fall into one or more of three classes: substitutional, insertional or deletional variants. These variants ordinarily are prepared by site specific mutagenesis of nucleotides in the DNA encoding the phytase protein, using cassette or PCR mutagenesis or other techniques well known in the art, to produce DNA encoding the variant, and thereafter expressing the DNA in recombinant cell culture as outlined above. However, variant phytase protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the phytase protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed variants screened for the optimal combination of desired activity. Techniques for making substitution mutations at predetermined sites in DNA having a known sequence are well known, for example, M13 primer mutagenesis and PCR mutagenesis. Screening of the mutants is done using assays of phytase protein activities.

Amino acid substitutions are typically of single residues; insertions usually will be on the order of from about 1 to 20 amino acids, although considerably larger insertions may be tolerated, and may occur internally or at either terminus of the encoded protein. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the phytase are desired, substitutions are generally made in accordance with the following chart of conservative substitution residues:

CHART I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| MetPhe | Leu, Ile |
| Ser | Met, Leu, Tyr |
| Thr | Thr |
| Trp | Ser |
| Tyr | Tyr |
| Val | Trp, Phe |
| | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g.

seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and may elicit the same immune response as the naturally-occurring analogue, although variants also are selected to modify the characteristics of the phytase proteins as needed. Alternatively, the variant may be designed such that the biological activity of the phytase is altered. For example, glycosylation sites may be altered or removed. Such alterations may result in altered immunogenicity, as well.

Covalent modifications of phytase polypeptides are included within the scope of this invention. One type of covalent modification includes reacting targeted amino acid residues of a phytase polypeptide with an organic derivatizing agent that is capable of reacting with selected side chains or the N- or C-terminal residues of a phytase polypeptide. Derivatization with bifunctional agents is useful, for instance, for crosslinking a phytase to another protein. Commonly used crosslinking agents include, e.g., 1,1-bis(diazoacetyl)-2-phenylethane, glutaraldehyde, N-hydroxysuccinimide esters, for example, esters with 4-azidoSallcylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl, threonyl or tyrosyl residues, methylation of the α-amino groups of lysine, arginine, and histidine side chains [T. E. Creighton, Proteins: Structure and Molecular Properties, W.H. Freeman & Co., San Francisco, pp. 7986 (1983)], acetylation of the N-terminal amine, and amidation of any C-terminal carboxyl group.

Another type of covalent modification of the phytase polypeptide included within the scope of this invention comprises altering the native glycosylation pattern of the polypeptide. "Altering the native glycosylation pattern" is intended for purposes herein to mean deleting one or more carbohydrate moieties found in native phytase, and/or adding one or more glycosylation sites that are not present in the native polypeptide.

Addition of glycosylation sites to polypeptides may be accomplished by altering the amino acid sequence thereof. The alteration may be made, for example, by the addition of, or substitution by, one or more serine or threonine residues to the native sequence phytase polypeptide (for O-linked glycosylation sites). The phytase amino acid sequence may optionally be altered through changes at the DNA level, particularly by mutating the DNA encoding the phytase polypeptide at preselected bases such that codons are generated that will translate into the desired amino acids.

Another means of increasing the number of carbohydrate moieties on the phytase polypeptide is by chemical or enzymatic coupling of glycosides to the polypeptide. Such methods are described in the art, e.g., in WO 87/05330 published 11 Sep. 1987, and in Aplin and Wriston, Crit. Rev. Biochem., pp. 259-306 (1981).

Removal of carbohydrate moieties present on the phytase may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of phytase comprises linking the phytase polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Phytases of the present invention may also be modified to form chimeric molecules comprising a phytase polypeptide fused to another, heterologous polypeptide or amino acid sequence. In one embodiment, such a chimeric molecule comprises a fusion of a phytase polypeptide with a tag polypeptide which provides an epitope to which an anti-tag antibody can selectively bind. The epitope tag is generally placed at the amino- or carboxyl-terminus of the phytase polypeptide. The presence of such epitope-tagged forms of a phytase can be detected using an antibody against the tag polypeptide. Also, provision of the epitope tag enables the phytase to be readily purified by affinity purification using an anti-tag antibody or another type of affinity matrix that binds to the epitope tag. In preferred embodiment, the chimeric molecule may comprise a fusion of a phytase polypeptide with an initial sequence or signal polypeptide, such as a secretion signal, of a different phytase or other protein. The fusion may involve the addition of a sequence from a protein, such as a phytase, which is native to the host cell in which the phytase is being expressed. Specific examples of this are provided in the Examples section, below.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8: 2159-2165 (1988)]; the c-myc tag and the 8F9, 3C7, 6E10, G4, B7 and 9E10 antibodies thereto [Evan et al., Molecular and Cellular Biology, 5: 3610-3616 (1985)]; and the Herpes Simplex virus glycoprotein D (gD) tag and its antibody [Paborsky et al., Protein Engineering, 3(6): 547-553 (1990)]. Other tag polypeptides include the Flag-peptide [Hopp et al., BioTechnology, 6: 1204-1210 (1988)]; the KT3 epitope peptide [Martin et al., Science, 255: 192-194 (1992)]; tubulin epitope peptide [Skinner et al., J. Biol. Chem., 266: 15163-15166 (1991)]; and the T7 gene 10 protein peptide tag [Lutz-Freyermuth et al., Proc. Natl. Acad. Sci. USA, 87: 6393-6397 (1990)].

Also included with the definition of phytase in one embodiment are other phytase proteins from other organisms, which are cloned and expressed as outlined below. Thus, probe or degenerate polymerase chain reaction (PCR) primer sequences may be used to find other related phytases from fungi or other organisms. As will be appreciated by those in the art, particularly useful probe and/or PCR primer sequences include the highly conserved amino acid sequences and the known binding or catalytic sequences. For example, the phosphate binding region of phytase produced in various fungi is highly conserved. As is generally known in the art, preferred PCR primers are from about 15 to about 35 nucleotides in length, with from about 20 to about 30 being preferred, and may contain inosine as needed. The conditions for the PCR reaction are well known in the art.

V. Expression and Recovery of Phytate Hydrolyzing Enzymes

The polynucleotide sequences of the present invention may be expressed by operatively linking them to an expression control sequence in an appropriate expression vector and employed in that expression vector to transform an appropriate host according to techniques well established in the art. The polypeptides produced on expression of the DNA sequences of this invention can be isolated from the fermentation of cell cultures and purified in a variety of ways according to well established techniques in the art. One of skill in the art is capable of selecting the most appropriate isolation and purification techniques.

More particularly, the present invention provides host cells, expression methods and systems for the production of phytate hydrolyzing enzymes derived from microorganisms, such as *Trichoderma* species. Once a nucleic acid sequence encoding a phytate hydrolyzing enzyme of the present invention is obtained, recombinant host cells containing the nucleic acid sequence may be constructed using techniques well known in the art. Molecular biology techniques are disclosed in Sambrook et al., Molecular Biology Cloning: A Laboratory Manual, Second Edition (1989) Cold Spring Harbor Laboratory Press, Cold Spring Harbor, N.Y. (1989) and Sambrook et al., Molecular Cloning, A Laboratory Manual, 3d Ed., Cold Spring Harbor Laboratory Press, Cold Spring Harbor, N.Y. (2001).

In one embodiment, nucleic acid sequences encoding phytate hydrolyzing enzymes derived from *Trichoderma* species and having at least 50%, at least 60%, at least 65%, at least 70%, at least 75%, at least 80%, at least 85%, at least 90% and at least 95% identity to the nucleic acid sequence of any one of FIGS. 1, 2 and 3 or a functional derivative thereof, or which is capable of hybridizing under conditions of intermediate to high stringency to the nucleic acid sequence of any one of FIGS. 1, 2 and 3, or which is complementary to the nucleic acid sequence of any one of FIGS. 1, 2 and 3 are obtained and transformed into a host cell using appropriate vectors.

The nucleic acid sequences encoding phytate hydrolyzing enzymes can include a leader sequence capable of providing for the secretion of the encoded phytase. Depending on whether the phytase is to be expressed intracellularly or is secreted, a DNA sequence or expression vector of the invention can be engineered such that the mature form of the phytase is expressed with or without a natural phytase signal sequence or a signal sequence which functions in a fungus (e.g., *Aspergillus niger*), other prokaryotes or eukaryotes. Expression can also be achieved by either removing or partially removing said signal sequence.

A variety of vectors and transformation and expression cassettes suitable for the cloning, transformation and expression in fungus, yeast, bacteria, insect and plant cells are known by those of skill in the art. Typically, the vector or cassette contains sequences directing transcription and translation of the nucleic acid sequence, a selectable marker, and sequences allowing autonomous replication or chromosomal integration. Suitable vectors comprise a region 5' of the gene which harbors transcriptional initiation controls and a region 3' of the DNA fragment which controls transcriptional termination. These control regions may be derived from genes homologous or heterologous to the host as long as the control region selected is able to function in the host cell.

Initiation control regions or promoters, which are useful to drive expression of the phytate hydrolyzing enzymes in a host cell are known to those skilled in the art. A nucleic acid sequence encoding the phytate hydrolyzing enzyme is linked operably through initiation codons to selected expression control regions for effective expression of such enzyme. Once suitable cassettes are constructed, they are used to transform the host cell.

In cases where plant expression vectors are used, the expression of a sequence encoding phytase may be driven by any of a number of promoters. For example, viral promoters such as the 35S and 19S promoters of CaMV (Brisson et al (1984) Nature 310:511-514) may be used alone or in combination with the omega leader sequence from TMV (Takamatsu et al (1987) EMBO J. 6:307-311). Alternatively, plant promoters such as the small subunit of RUBISCO (Coruzzi et al (1984) EMBO J. 3:1671-1680; Broglie et al (1984) Science 224:838-843); or heat shock promoters (Winter J and Sinibaldi R M (1991) Results Probl Cell Differ 17:85-105) may be used. These constructs can be introduced into plant cells by direct DNA transformation or pathogen-mediated transfection. For reviews of such techniques, see Hobbs S or Murry L E (1992) in McGraw Hill Yearbook of Science and Technology, McGraw Hill, New York, N.Y., pp 191-196; or Weissbach and Weissbach (1988) Methods for Plant Molecular Biology, Academic Press, New York, N.Y., pp 421-463.

General transformation procedures are taught in Current Protocols In Molecular Biology (3rd edition, edited by Ausubel et al., John Wiley & Sons, Inc. 1995, Chapter 9) and include calcium phosphate methods, transformation using PEG and electroporation. For *Aspergillus* and *Trichoderma*, PEG and Calcium mediated protoplast transformation can be used (Finkelstein, D B 1992 Transformation. In Biotechnology of Filamentous Fungi. Technology and Products (eds by Finkelstein & Bill) 113-156. Electroporation of protoplast is disclosed in Finkelestein, D B 1992 Transformation. In Biotechnology of Filamentous Fungi. Technology and Products (eds by Finkelstein & Bill) 113-156. Microprojection bombardment on conidia is described in Fungaro et al. (1995) Transformation of *Aspergillus nidulans* by microprojection bombardment on intact conidia, FEMS Microbiology Letters 125 293-298. *Agrobacterium* mediated transformation is disclosed in Groot et al. (1998) *Agrobacterium tumefaciens*-mediated transformation of filamentous fungi, Nature Biotechnology 16 839-842 and U.S. Pat. No. 6,255,115. For transformation of *Saccharomyces*, lithium acetate mediated transformation and PEG and calcium mediated protoplast transformation as well as electroporation techniques are known by those of skill in the art.

Host cells which contain the coding sequence for a phytate hydrolyzing enzyme of the present invention and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid sequence or protein.

It should also be noted that the invention contemplates in vitro expression of the phytase enzymes described herein.

In preferred embodiments of the invention, phytase is produced in fungal cells. In one embodiment of the present invention, a polynucleotide sequence encoding a phytate hydrolyzing enzyme derived from *Trichoderma reesei* (deposit no. ATCC 13631) is isolated and expressed in *Trichoderma reesei*. In this embodiment, the phytase may be expressed under conditions in which it might not otherwise be expressed, or the phytase will be overexpressed under conditions that the indigenous phytase is expressed. In another embodiment, a polynucleotide sequence encoding a phytate hydrolyzing enzyme derived from *Trichoderma reesei* is isolated and expressed in *Aspergillus niger*, and in another embodiment is expressed in *Aspergillus nidulans*. The expressed phytase can then be recovered, e.g., as described below.

In preferred embodiments of the invention, the phytase is expressed in plants. Transgenic plant, as used herein, refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant and parts of said plant, for instance grains, seeds, flowers, leaves, roots, fruit, pollen, stems, etc.

The present invention is applicable to both dicotyledonous plants (e.g. tomato, potato, soybean, cotton, tobacco, etc.) and monocotyledonous plants, including, but not limited to graminaceous monocots such as wheat (*Triticum* spp.), rice (*Oryza* spp.), barley (*Hordeum* spp.), oat (*Avena* spp.), rye (*Secale* spp.), corn (*Zea mays*), sorghum (*Sorghum* spp.) and millet (*Pennisetum* spp). For example, the present invention can be employed with barley genotypes including, but not limited to Morex, Harrington, Crystal, Stander, Moravian III, Galena, Salome, Steptoe, Klages, Baronesse, and with wheat genotypes including, but not limited to Yecora Rojo, Bobwhite, Karl and Anza. In general, the invention is particularly useful in cereals.

Standard molecular biology methods and plant transformation techniques can be used to produce transgenic plants that produce seeds containing phytase protein. The following description provides general guidance as to the selection of particular constructs and transformation procedures.

The present invention utilizes recombinant constructs that are suitable for obtaining expression of phytase in plant seeds relative to non-transformed plant seeds. In their most basic form, these constructs may be represented as Pr-Ph, wherein Pr is a seed-specific promoter and Ph is a nucleic acid sequence encoding phytase. In another embodiment, a peptide signal sequence that targets expression of the phytase polypeptide to an intracellular body may be employed. Such constructs may be represented as Pr-SS-Ph, wherein SS is the signal peptide. Nucleic acid molecules that may be used as the source of each of these components are described in the Definitions section above.

Each component is operably linked to the next. For example, where the construct comprises the hordein D-promoter (P), the hordein D-signal sequence (SS) encoding the hordein signal peptide, and an open reading frame encoding a phytase (Ph), the hordein promoter is linked to the 5' end of the sequence encoding the hordein signal sequence, and the hordein signal sequence is operably linked to the 5' end of the phytase open reading frame, such that C terminus of the signal peptide is joined to the N-terminus of the encoded protein.

The construct will also typically include a transcriptional termination region following the 3' end of the encoded protein ORF. Illustrative transcriptional termination regions include the nos terminator from *Agrobacterium* Ti plasmid and the rice alpha-amylase terminator.

Standard molecular biology methods, such as the polymerase chain reaction, restriction enzyme digestion, and/or ligation may be employed to produce these constructs comprising any nucleic acid molecule or sequence encoding a phytase protein or polypeptide.

Introduction of the selected construct into plants is typically achieved using standard transformation techniques. The basic approach is to: (a) clone the construct into a transformation vector; which (b) is then introduced into plant cells by one of a number of techniques (e.g., electroporation, microparticle bombardment, *Agrobacterium* infection); (c) identify the transformed plant cells; (d) regenerate whole plants from the identified plant cells, and (d) select progeny plants containing the introduced construct. Preferably all or part of the transformation vector will stably integrate into the genome of the plant cell. That part of the transformation vector which integrates into the plant cell and which contains the introduced Pr-Ph or Pr-SS-Ph sequence (the introduced "phytase transgene") may be referred to as the recombinant expression cassette.

Selection of progeny plants containing the introduced transgene may be made based upon the detection of phytase expression in seeds, or upon enhanced resistance to a chemical agent (such as an antibiotic) as a result of the inclusion of a dominant selectable marker gene incorporated into the transformation vector.

Successful examples of the modification of plant characteristics by transformation with cloned nucleic acid sequences are replete in the technical and scientific literature. Selected examples, which serve to illustrate the knowledge in this field of technology include:

U.S. Pat. No. 5,571,706 ("Plant Virus Resistance Gene and Methods");
U.S. Pat. No. 5,677,175 ("Plant Pathogen Induced Proteins");
U.S. Pat. No. 5,510,471 ("Chimeric Gene for the Transformation of Plants");
U.S. Pat. No. 5,750,386 ("Pathogen-Resistant Transgenic Plants");
U.S. Pat. No. 5,597,945 ("Plants Genetically Enhanced for Disease Resistance");
U.S. Pat. No. 5,589,615 ("Process for the Production of Transgenic Plants with Increased Nutritional Value Via the Expression of Modified 2S Storage Albumins");
U.S. Pat. No. 5,750,871 ("Transformation and Foreign Gene Expression in *Brassica* Species");
U.S. Pat. No. 5,268,526 ("Overexpression of Phytochrome in Transgenic Plants");
U.S. Pat. No. 5,780,708 ("Fertile Transgenic Corn Plants");
U.S. Pat. No. 5,538,880 ("Method For Preparing Fertile Transgenic Corn Plants");
U.S. Pat. No. 5,773,269 ("Fertile Transgenic Oat Plants");
U.S. Pat. No. 5,736,369 ("Method For Producing Transgenic Cereal Plants");
U.S. Pat. No. 5,610,049 ("Methods For Stable Transformation of Wheat").

These examples include descriptions of transformation vector selection, transformation techniques and the construction of constructs designed to express an introduced transgene.

The transgene-expressing constructs of the present invention may be usefully expressed in a wide range of higher plants to obtain seed- or grain-specific expression of selected polypeptides. The invention is expected to be particularly applicable to monocotyledonous cereal plants including barley, wheat, rice, rye, maize, triticale, millet, sorghum, oat, forage, and turf grasses. In particular, the transformation methods described herein will enable the invention to be used with genotypes of barley including Morex, Harrington, Crystal, Stander, Moravian III, Galena, Golden Promise, Steptoe, Klages and Baronesse, and commercially important wheat genotypes including Yecora Rojo, Bobwhite, Karl and Anza.

The invention may also be applied to dicotyledenous plants, including, but not limited to, soybean, sugar beet, cotton, beans, rape/canola, alfalfa, flax, sunflower, safflower, brassica, cotton, flax, peanut, clover; vegetables such as lettuce, tomato, cucurbits, cassava, potato, carrot, radish, pea, lentils, cabbage, cauliflower, broccoli, Brussels sprouts, peppers; and tree fruits such as citrus, apples, pears, peaches, apricots, and walnuts.

A number of recombinant vectors suitable for stable transformation of plant cells or for the establishment of transgenic plants have been described including those described in Weissbach and Weissbach, (1988), and Gelvin et al., J. Bacteriol. 172(3): 1600-1608 (1990). Typically, plant transformation vectors include one or more ORFs under the transcriptional control of 5' and 3' regulatory sequences and a dominant selectable marker with 5' and 3' regulatory sequences. The selection of suitable 5' and 3' regulatory sequences for constructs of the present invention is discussed above. Dominant selectable marker genes that allow for the ready selection of transformants include those encoding antibiotic resistance genes (e.g., resistance to hygromycin, kanamycin, bleomycin, G418, streptomycin or spectinomycin) and herbicide resistance genes (e.g, phosphinothricin acetyltransferase).

Methods for the transformation and regeneration of both monocotyledonous and dicotyledonous plant cells are known, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium* mediated transformation. Typical procedures for transforming and regenerating plants are described in the patent documents listed at the beginning of this section.

Following transformation, transformants are preferably selected using a dominant selectable marker. Typically, such a marker will confer antibiotic or herbicide resistance on the seedlings of transformed plants, and selection of transformants can be accomplished by exposing the seedlings to appropriate concentrations of the antibiotic or herbicide. After transformed plants are selected and grown to maturity to allow seed set, the seeds can be harvested and assayed for expression of phytase.

The phytase of the invention can be recovered from culture medium or from host cell lysates. If membrane-bound, it can be released from the membrane using a suitable detergent solution (e.g. Triton-X 100) or by enzymatic cleavage. Cells employed in expression of phytase can be disrupted by various physical or chemical means, such as freeze-thaw cycling, sonication, mechanical disruption, or cell lysing agents. It may be desired to purify the phytase from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants; and metal chelating columns to bind epitope-tagged forms of the phytase. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular form of phytase produced.

In a preferred embodiment, the phytase(s) is/are produced in transgenic non-human animals. Methods of producing such transgenic animals are described, for example, in U.S. Pat. No. 6,291,740. Methods for the successful production of transgenic bovine (e.g., U.S. Pat. Nos. 6,080,912 and 6,066,725), swine (e.g., U.S. Pat. Nos. 6,271,436 and 5,942,435), goats (e.g., U.S. Pat. No. 5,907,080) and fish (e.g., U.S. Pat. No. 5,998,697) are available in the art. Furthermore, organ-specific expression, particularly expression in milk produced by the transgenic animals, is within the skill of the ordinary artisan (e.g., e.g., U.S. Pat. Nos. 6,268,545 and 6,262,336). The disclosure of each of these patents is incorporated herein in its entirety.

VI. Assaying for Phytase Activity

Assays for phytase activity are well known in the art. Perhaps the most widely used is the classic assay for liberation of inorganic phosphate developed by Fiske and SubbaRow, *Journal of Biological Chemistry* 66:375-392 (1925). A variation of this method is found in Mitchell et al., *Microbiol.* 143:245-252 (1997). A preferred method is described in Food Chemicals Codex, 4th Edition, Committee on Food Chemicals Codex, Institute of Medicine, National Academy Press, Washington, D.C., 1996 at pages 809-810. Each of these references are incorporated herein.

Generally, the assay involves allowing a measured weight or volume of a phytase sample to react with phytate in solution for a measured period of time. The reaction is stopped and a color solution containing ammonium molybdate (AM) is added to the reaction solution. Colorimetry is then performed using a spectrophotometer and compared to controls of known concentration of inorganic phosphate ($P_i$) and/or controls produced by reactions with enzymes having known phytase activity. A Unit of activity is determined as the amount of enzyme sample required to liberate 1 µmol $P_i$ per minute from phytate under defined reaction conditions.

Enzyme reactions are frequently run at pH 5.5 and 37° C. However, pH and temperature conditions may be varied to determine optimum reaction conditions and tolerances for a given phytase. When different reaction conditions are tested, Units of activity should still be related to a single specific set of reaction conditions.

The reaction may be stopped and then the color solution added, or a stop/color solution may be used that both arrests the enzyme activity and adds a product whose spectral absorbance is measurably affected by the concentration of $P_i$ in a predictable and calculatable manner. As discussed above, the color solutions generally contain AM. Various examples of such solutions are available in the relevant literature. In U.S. Pat. No. 6,039,942, the reaction is stopped using trichloroactetate (TCA) and the color solution added thereafter contained ferrous sulfate and AM. In other examples wherein the reaction was first stopped with TCA, different color solution contained sulfuric acid, AM and ascorbic acid (U.S. Pat. No. 6,221,644) and sulfuric acid, AM and ferrous sulfate (U.S. Pat. No. 6,190,897). In other cases, the color and stop solution are the same. For example, in both U.S. Pat. Nos. 6,139,902 and 6,261,592, the solution contained sulfuric acid, AM and acetone, after which a solution containing acetic acid was added. In a preferred embodiment, the color/stop solution contains ammonium vanadate, AM and nitric acid (see *Food Chemicals Codex*, above).

Wavelength-specific absorption by the final solution, containing the reaction solution and stop/color solution(s), is measured using a spectrophotometer. Many such instruments are available and their use is routine in the art. The wavelength used for absorption measurement can vary with the components of the color solution. For example, the references cited above measured absorbance at 380, 415, 690, 700 or 750 nm. Any of these may provide adequate indication of $P_i$ concentration in these solutions. However, the wavelength used should generally be the one described in a given protocol. The skilled artisan can easily determine empirically which wavelength provides optimum discrimination of differences in $P_i$ concentration by comparing the linearity of absorption change between serially diluted control solutions of known $P_i$ concentration at different wavelengths.

VII. Applications of Phytate Hydrolyzing Enzymes

The phytase and derivatives thereof as taught herein can be used in a variety of applications where it is desirable to separate phosphorous from phytate. Several exemplary applications are set forth below.

For example, the invention provides for the use of cells or spores capable of producing phytase according to the invention as a probiotic or direct fed microbial product. Preferred embodiments for said uses are phytase-producing *Trichoderma* sp. and *Aspergillus* sp. of the invention.

In addition, the invention contemplates the use of phytase as described herein in food or animal feed.

The present invention provides food or animal feed including phytase as described herein. Preferably, said food or animal feed comprises phytase as an additive which is active in the digestive tract, preferably the crop and/or small intestine, of livestock, such as poultry and swine, and aquatic farm animals including fish and shrimp. Said additive is also preferably active in food or feed processing.

In an alternative embodiment, phytase or phytase producing organisms are added as a pretreatment to food or animal feed, such as in the processing of the food or feed. In this embodiment, the phytase is active prior to consumption of the food or feed, but may or may not be active at the time the food or animal feed is consumed.

Compositions comprising polypeptides or proteins possessing phytase activity may be prepared in accordance with methods known in the art and may be in the form of a liquid or a dry composition. The polypeptide to be included in the composition may be stabilized in accordance with methods known in the art.

The invention additionally provides food or animal feed comprising cells, spores or plant parts, including seeds, capable of expressing phytase as described herein.

Still further, the present invention contemplates a method for the production of a food or animal feed, characterized in that phytase according to the invention is mixed with said food or animal feed. Said phytase is added as a dry product before processing or as a liquid before or after processing. According to one embodiment, wherein a dry powder is used, the enzyme is diluted as a liquid onto a dry carrier such as milled grain.

Liquid compositions need not contain anything more than the phytase enzyme, preferably in a purified form. Usually, however, a stabilizer such as glycerol, sorbitol or mono propylene glycol is also added. The liquid composition may also comprise one or more other additives, such as salts, sugars, preservatives, pH-adjusting agents (i.e., buffering agents), proteins, or phytate (a phytase substrate). Typical liquid composition are aqueous or oil-based slurries. The liquid compositions can be added to a food or feed after an optional pelleting thereof.

Dry compositions may be spraydried compositions, in which case the composition need not contain anything more than the enzyme in a dry form. Usually, however, dry compositions are so-called granulates which may readily be mixed with for example food or feed components, or more preferably, form a component of a pre-mix. The particle size of the enzyme granulates preferably is compatible with that of the other components of the mixture. This provides a safe and convenient means of incorporating enzymes into for example an animal feed.

Agglomeration granules are prepared using agglomeration techniques in a high shear mixer (e.g., Lodige) during which a filler material and the enzyme are co-agglomerated to form granules. Absorption granulates are prepared by having cores of a carrier material to adsorb/be coated by the enzyme.

Typical filler materials are salts such as disodium sulphate. Other fillers are kaolin, talc, magnesium aluminum silicate and cellulose fibers. Optionally, binders such as dextrins are also included in agglomeration granules.

Typical carrier materials are starch, e.g., in the form of cassava, corm, potato, rice and wheat. Salts may also be used.

Optionally, the granulates are coated with a coating mixture. Such mixture comprises coating agents, preferably hydrophobic coating agents, such as hydrogenated palm oil and beef tallow, and if desired other additives, such as calcium carbonate or kaolin.

Additionally, phytase compositions may contain other substituents such as coloring agents, aroma compounds, stabilizers, vitamins, minerals other feed or food enhancing enzymes and the like. This is so in particular for the so-called premixes.

A "feed" and a "food," respectively, means any natural or artificial diet, meal or the like or components of such meals intended or suitable for being eaten, taken in, digested, by an animal and a human being, respectively.

A "food or feed additive" is an essentially pure compound or a multi component composition intended for or suitable for being added to food or feed. It usually comprises one or more compounds such as vitamins, minerals or feed enhancing enzymes and suitable carriers and/or excipients, and it is usually provided in a form that is suitable for being added to animal feed.

The phytases of the invention can also be used in poultry food to improve egg shell quality (reduction of losses due to breaking), see for example, The Merck Veterinary Manual (Seventh Edition, Merck & Co., Inc., Rahway, N.J., USA, 1991, page 1268); Jeroch et al. Bodenkultur Vo. 45(4): 361-368 (1994); Poultry Science, 75(1): 62-68 (1996); Canadian Journal of Animal Science 75(3): 439-444 (1995); Poultry Science 74(5): 784-787 (1995) and Poultry Science 73(10): 1590-1596 (1994).

An effective amount of the polypeptide in food or feed is typically from about 10 to 50,000 U/kg feed or food; preferably from about 10 to 15,000, more preferably from about 10 to 10,000, in particular from about 100 to 5,000, especially from about 100 to about 2,000 U/kg feed or food.

The present invention also provides a method for the production of a food or animal feed, characterized in that cells, plant parts, including seeds, and/or spores capable of expressing phytase according to the invention are added to said food or animal feed. Such cells or spores, may be of any origin, bacterial, plant, or animal.

Further, the present invention provides for the use of the phytase described herein with or without accessory phosphatases in the production of inositol and inorganic phosphate, and phytate intermediates.

Also provided is a method for the reduction of levels of phosphorous in animal manure, characterized in that an animal is fed an animal feed according to the invention in an amount effective in converting phytate contained in said animal feed.

In one embodiment, the transgene protein, for example phytase expressed in plants, especially seeds or grains, using the methods described herein, is used in the production and synthesis of phytase. The phytase transgene expressed by the recombinant nucleic acid of the invention may be harvested at any point after expression of the protein has commenced. When harvesting from the seed or grain or other part of a plant for example, it is not necessary for the seed or grain or other part of the plant to have undergone maturation prior to harvesting. For example, transgene expression may occur prior to seed or grain maturation or may reach optimal levels prior to seed or grain maturation. The transgene protein may be isolated from the seeds or grain, if desired, by conventional protein purification methods. For example, the seed or grain can be milled, then extracted with an aqueous or organic extraction medium, followed by purification of the extracted phytase protein. Alternatively, depending on the nature of the intended use, the transgene protein may be partially purified, or the seed or grain may be used directly without purification of the transgene protein for food or animal feed, food processing or other purposes.

Alpha-amylases break down starch 1-4 linkages. Amylases are enzymes fundamental to the brewing and baking industries. Amylases are required to break down starch in malting and in certain baking procedures carried out in the absence of added sugars or other carbohydrates. Obtaining adequate activity of these enzymes is problematic especially in the malting industry. It has been known for some time that phytate has an inhibitory effect on amylases. A method of adequately increasing the activity of amylases with a physiologically acceptable system, leads to more rapid malting methods and, owing to increased sugar availability, to alcoholic beverages such as beers with reduced carbohydrate content.

Accordingly, seeds or grains with phytase expression provide advantages in the production of malt and beverages produced by a fermentation process. Enhanced activity of amylases in grain increases the speed and efficiency of germination, important in malting, where malt is produced having increased enzymatic activity resulting in enhanced hydrolysis of starch to fermentable carbohydrates, thereby, improving the efficiency of fermentation in the production of alcoholic beverages, for example, beer and scotch whiskey. Enhanced fermentation processes also find use in the production of alcohols that are not intended for human consumption, i.e., industrial alcohols.

The phytase and phytate-derived intermediates of the invention also find use in many other agricultural, industrial, medical and nutritional applications. For example phytase and phytate-derived intermediates can be used in grain wet milling. Phytate is used in cleaning products, rust removal products and in the removal of metals and other polycations from such diverse materials as waste products and carbonated beverages. Phytate and phytases may be used in the isolation and recovery of rare metals. Phytases may be used to produce lower phosphate homologs of phytate, which may be used in dentifrice and other dental care products as well as potential treatments or preventatives of bone resorption (e.g., in osteoporosis) and renal calculi (kidney stones). Phytate and derivatives have found use in the production of tofu, and chelation of minerals (e.g., iron, zinc, calcium or magnesium) with phytate, followed by release with addition of phytase may provide a unique means of providing these nutrients. Phytases may be used in the production of inositol from phytate its use in food products. Phytases may also be used in the chemical and biochemical synthesis of phosphate containing materials. Phytases, phytate and lower phosphate phytate derivatives find many other uses in personal care products, medical products and food and nutritional products, as well as various industrial applications, particularly in the cleaning, textile, lithographic and chemical arts.

The following examples are offered for illustrative purposes only, and are not intended to limit the scope of the present invention in any way. The skilled artisan will appreciate that the methods disclosed may be applied to any number of different species, including to obtain all sequences disclosed herein. All patent and literature references cited in the present specification are hereby incorporated by reference in their entirety.

EXAMPLES

Example 1

Induction and Isolation of Phytase mRNA from *T. reesei*

*T. reesei* (ATCC 13631) was grown under different conditions to generate mycelium expressing growth condition-specific mRNA profiles. The RNA was then isolated, pooled and cDNA libraries were generated.

1A. Growth of *T. reesei* Mycelia

All cultures were grown in yeast extract/glucose (YEG) liquid medium overnight at 28□ C. They were then transferred to the following conditions and cultured for the time stated at 28□ C, unless otherwise indicated:

Experiment 1:
  A. Vogel's+2% avicel, 3 days and 6 days
  B. Vogel's+2% solkafloc, 3 days and 6 days
  C. Vogel's+2% wheat bran, 6 days
  D. Vogel's+2% beet pulp, 6 days
  E. Solid state culture on wheat bran (15 g wheat bran, 1 g Proflo, 1 g solkafloc, 30 ml water), 7 days
  F. Solid state culture on beet pulp (15 g beet pulp, 1 g Proflo, 1 g solkafloc, 30 ml water), 9 days Experiment 2:
  A. Vogel's+2% glucose, 24 h
  B. Vogel's+2% lactose, 24 h
  C. Vogel's+2% xylose, 24 h
  D. Vogel's+2% fructose, 24 h
  E. Vogel's+2% maltose, 24 h
  F. Vogel's w/o any carbon added, 24 h
  G. Vogel's w/o any nitrogen added, 24 h
  H. Vogel's+2% wheat bran, 3 days
  I. Vogel's+2% wheat bran, 6 days
  J. Vogel's+2% solkafloc, 3 days
  K. Vogel's+2% solkafloc, 6 days
  L. Vogel's+2% avicel, 3 days
  M. Vogel's+2% avicel, 6 days
  N. Vogels+2% phosphoric swollen cellulose, 3 days
  O. Solid state (15 g wheat bran, 1 g Proflo, 1 g solkafloc, 30 mL water), 6 days
  P. YEG, 42□C for 1.5 h (heat shock)

Q. YEG, 20 mM DTT for 1.5 h (redox stress)
R. YEG, unagitated in closed container for 1.5 h at RT (anoxia)

Media Preparations

Yeast Extract/Glucose medium—1 liter

| | |
|---|---|
| 1. dH20 | 1000 ml |
| 2. Yeast extract | 5 g |
| 3. Glucose | 20 g |

Vogel's Solution—1 liter

| | |
|---|---|
| 1. 50× Vogels Stock Solution | 25 ml |
| 2. dH2O | 975 ml |
| 3. Autoclave | |

50× Vogel's Stock Solution—1 liter

| | |
|---|---|
| 1. Na3 citrate | 150 g |
| 2. KH2PO4 | 250 g |
| 3. NH4NO3 | 100 g |
| 4. MgSO4*7H2O | 10 g |
| 5. CaCl2*2H2O | 5 g |
| 6. Trace Element Solution | 5 ml |
| 7. Biotin Solution | 2.5 ml |
| 8. in dH2O, bring to a final volume of 1 liter | |

Trace Element Solution—1 liter

| | |
|---|---|
| 1. Citric Acid | 50 g |
| 2. ZnSO4*7H2O | 50 g |
| 3. Fe(NH4)2SO4*6H2O | 10 g |
| 4. CuSO4*5H2O | 2.5 g |
| 5. MnSO4*4H2O | 0.5 g |
| 6. H3BO3 | 0.5 g |
| 7. NaMoO4*2H2O | 0.5 g |
| 8. in dH2O, bring to a final volume of 1 liter | |

Biotin Solution—1 liter

| | |
|---|---|
| 1. d-Biotin | 0.1 g |
| 2. in dH2O, bring to a final volume of 1 liter | |

1B. Isolation of RNA

Total RNA was isolated using Life Technologies☐ TRIZOL® Reagent (Catalog No. 15596-026) and a slight modification of its accompanying RNA isolation protocol (incorporated herein in its entirety). Unless otherwise stated, the procedure was carried out at 15 to 30☐ C, and reagent a at 15 to 30☐ C.

*T. reesei* mycelium from the different cultures described in 1A was filtered to remove excess liquid and frozen in liquid nitrogen. The frozen mycelium was ground in a mortar and pestle and added to TRIZOL Reagent (approximately 9 ml per 1 ml of ground mycelium). The homogenate was then centrifuged at 12,000×g for 10 minutes at 2 to 8☐C. The cleared homogenate solution (supernatant) was transferred to a fresh tube.

The homogenized samples were incubated for 5 minutes at 15 to 30☐C to permit the complete dissociation of nucleoprotein complexes. Then, 0.2 mL of chloroform per 1 mL of TRIZOL Reagent was added and the sample tubes were capped securely. The tubes were shaken vigorously by hand for 15 seconds, then incubated at 15 to 30☐C for 2 to 3 minutes. The samples were then centrifuged at no more than 12,000×g for 15 minutes at 2 to 8☐C. Following centrifugation, the mixture separates into a lower red, phenol-chloroform phase, an interphase, and a colorless upper aqueous phase. The aqueous phase (about 60% of the volume of reagent) was then transferred to a fresh tube.

The RNA from the aqueous phase was precipitated by adding 0.25 mL of isopropanol followed by 0.25 mL of a high salt precipitation solution (0.8 M sodium citrate and 1.2 M NaCl) per 1 mL of TRIZOL Reagent used for the homogenization. The resulting solution was mixed and the samples were incubated at 15 to 30☐C for 10 minutes, then centrifuged at no more than 12,000×g for 10 minutes at 2 to 8☐ C.

The supernatant was removed and the gel-like RNA pellet was washed once with 75% ethanol (made with RNase-free water), using at least 1 mL of 75% ethanol per 1 mL of TRIZOL Reagent used for the initial homogenization. The sample was then mixed by vortexing and centrifuged at no more than 7,500×g for 5 minutes at 2 to 8☐ C.

The supernatant was again removed and the RNA pellet was briefly dried (air-dry or vacuum-dry for 5-10 minutes). The RNA was dissolved in RNase-free water by passing the solution a few times through a pipette tip and then incubating for 10 minutes at 55 to 60° C.

Purity of the isolated RNA was checked by gel electrophoresis.

1C. Construction of cDNA Library

Equal volumes of RNA obtained from each of the growth conditions described for Experiment 1 in 1A was pooled and a total of 2 mg was forwarded to Life Technologies (Rockville, Md.) for construction of a cDNA library. Similarly, RNA from Experiment 2 in 1A was pooled and forwarded to Life Technologies for cDNA construction. The cDNA libraries were produced using standard procedures in the art. The following is a summary of the steps taken.

Poly-A RNA was isolated from the total RNA by chromatography. The total RNA was run on an oligo(dT) cellulose column, and the poly-A RNA (mRNA) was subsequently eluted.

From the mRNA, cDNA were generated by Life Technologies (Rockville, Md.) using the Life Technologies☐ cDNA Synthesis System (the Instruction Manual for which is hereby incorporated in its entirety). The following outlines procedures to be used.

First Strand Synthesis

Reaction components for production of a first strand of cDNA from the isolated *T. reesei* mRNA are combined in a 1.5 ml microcentrifuge tube on ice. The reaction mixture, in a volume of 50 µl, contains the following components:

50 mM Tris-HCl (pH 8.3)
75 mM KCl
3 mM $MgCl_2$
10 mM DTT
500 µM each dATP, dCTP, dGTP and dTTP
50 µg/ml oligo(dT)$_{12-18}$
100 µg/ml poly (A) RNA (from *T. reesei*)
10,000 units/ml Moloney Murine Leukemia Virus (M-MLV) reverse transcriptase The reverse transcriptase is added last, with mixing, to initiate the reaction. Optionally, a 10 µl aliquot is immediately removed and transferred to a separate tube containing 1 µCi [☐-$^{32}$P]dCTP tracer. Both tubes are then incubated at 37☐C for 1 hour. The tubes are placed back on ice after incubation and the reaction is terminated by adding 1 µl of 0.25 M Na$_2$EDTA (pH 7.5). The 40 µl reaction mixture is used for second strand cDNA synthesis.

If made, the tracer mixture is diluted with 89 µl water and duplicate 5 µl aliquots are spotted onto filters (e.g., glass fiber filters). The second filter is washed three times (sequentially), 5 minutes each, with about 50 ml per wash of ice-cold TCA. The second filter is then washed with 50 ml of 95% ethanol for about 5 minutes at room temperature, then dried. The two filters are counted in standard scintillant to determine the amount of $^{32}$P in the mixture (from the first filter) and the amount of $^{32}$P incorporated in the first strand cDNA (from the second filter) to determine the yield of first strand cDNA.

The remainder of the tracer mixture is extracted with phenol and ethanol precipitated. The pellet is isolated and gel electrophoresis using alkaline agarose gel is performed to determine the size of the single strand products.

Second Strand Synthesis

Double stranded cDNA may be produced using a procedure tailored for the production of cDNA to which linkers will be added.

In a 1.5 ml microcentrifuge tube on ice, components are added to 40 µl of the first strand reaction product to produce 300 µl of a second strand reaction mixture. The components are added in the following order: DEPC-treated water, dNTP mixture, concentrated buffer/salt solution, E. coli DNA polymerase 1, E. coli RNase H and E. coli DNA ligase. The final reaction mixture has the following composition, in addition to the original components in the first strand reacion product:

25 mM Tris-HCl (pH 8.3)
100 mM KCl
10 mM (NH$_4$)$_2$SO$_4$
5 mM MgCl$_2$
250 µM ea. dATP, dCTP (including 10 µCi of [□-$^{32}$P] dCTP), dGTP, dTTP
0.15 mM NAD
5 mM DTT
250 U/ml DNA polymerase I
8.5 U/ml RNase H
30 U/ml DNA ligase The tube is vortexed gently to mix and incubated at 16□C for 2 hours. The tube is then placed on ice and 25 µl of Na$_2$EDTA (pH 7.5) is added.

A 10 µl amount of the mixture is added to 90 µl water. A 5 µl aliquot of this is spotted onto a first glass fiber filter and dried. Another 10 µl amount of the undiluted mixture is spotted onto a second glass fiber filter, which is washed three times, 5 minutes each, with 50 ml ice-cold TCA each wash. The second filter is then washed once at room temperature with 95% ethanol for 5 minutes. The filters are counted in standard scintillant, the first to be used to determine the amount of $^{32}$P in the mixture (specific activity) and the second to be used to determine the amount of $^{32}$P incorporated into the cDNA.

The remainder of the reaction mixture is extracted in phenol and precipitated with ethanol. The pellet is then dissolved in 200 µl of sterile TE buffer (10 mM Tris-HCl (pH 7.5), i mM Na$_2$EDTA), to which 100 µl of 7.5 M ammonium acetate, followed by 500 µl of ethanol are then added to precipitate. The pellet is dried, then dissolved in 20 µl of sterile TE buffer. 2 µl are removed and analyzed by alkaline agarose gel electrophoresis. Linkers or adapters are added to the remainder for incorporation into a vector.

For linker addition, the cDNA is first methylated with a methylase specific for the linker to be used to protect internal restriction sites. The termini of the cDNA are repaired with T4 DNA polymerase, and linkers are then added by blunt end ligation. Linkers should be provided at a high concentration for efficient addition. The cDNA is digested with the selected restriction endonuclease(s), then purified from the small digestion products (e.g., by column chromatography). The vector is digested with the same restriction endonuclease(s) and combined with the cDNA, which are then ligated into the vector as an insert.

The linkers or adapters added to the cDNA contained restriction endonuclease sites such that a SalI site is found 5□ to the cDNA sequence corresponding to the original mRNA and a NotI site 3□ to the cDNA sequence corresponding to the original mRNA. The cDNA were then inserted into a pREP3Y shuttle vector. The pREP3Y vector is a modified pREP3X vector (ATCC number 87603), wherein the vector was digested with BamHI endonuclease, and a synthetic oligonucleotide inserted to add restriction sites. The resulting vector has the following restriction sites in the polylinker region: Xho1, Sall, Xbal, BamHl, Smal, Notl and Smal. The vector and cDNA were digested with Sall/Notl and the cDNA inserted into the vector.

E coli strain DH12S was transformed with the vector to create the cDNA library. An unamplified library was returned to the inventors. Individual clones were then plated and grown.

Example 2

Identification and Sequence Analysis of a Phytase from *T reesei*

The plasmid containing a cDNA insert was isolated from clones of the libraries described in Example 1 and a single pass 5□ sequence of the cDNA insert was obtained from approximately 10,000 clones at North Carolina State University (Fungal Genomics Laboratory, College of Agriculture and Life Sciences, Raleigh, N.C.). Sequences of the cDNA were obtained using a primer corresponding to the vector sequence adjacent to the 5□ end of the cDNA insert. Clones containing cDNA sequences similar to known phytases were identified for further investigation using the BLAST program (BLASTX and BLASTN) using default parameters.

Once cDNA from clones of interest were identified, as described above, additional sequencing was performed. Sequence analysis was performed on double stranded plasmid DNA by BaseClear (P.O. Box 1336, 2303 BH Leiden, Netherlands). Forward and reverse primers were first used, based on sequences of the vector adjacent to the insert (Sall-Notl fragment).

```
Forward primer, LTF1:
TAATTATTTCAATCTCATTCTCAC        (SEQ ID NO: 15)

Reverse primer, LTR1:
ATCGTAATATGCAGCTTGAATGGG        (SEQ ID NO: 16)
```

A second set of forward and reverse primers specific for the phytase disclosed herein was subsequently synthesized, based on the phytase cDNA sequences obtained using the first set.

```
Forward primer, PhytF2:
CGAGGTTCAACTCAAAGACAGC        (SEQ ID NO: 17)

Reverse primer, PhytF3:
TCTGGCTTGGCGTCTTCGG           (SEQ ID NO: 18)
```

Sequence analysis using both sets of primers and eliminating the vector sequence allowed elucidation of a full length sequence of the original mRNA (FIG. 1). This sequence was analyzed using the DNAstar software package. An open reading frame (ORF) was deduced (FIG. 2) using DNA EditSeq and an encoded amino acid sequence was derived therefrom (FIG. 4).

The amino acid sequence of the *T. reesei* phytase was compared with sequences of known phytase. Sequences were aligned using the CLUSTAL method with the PAM250 residue weight table. The *T. reesei* phytase was determined to be 41-49% identical to known phytases from other filamentous fungi. Very high sequence identity was found with active regions of all of the known filamentous fungi phytases, such as the phosphate binding region.

The alignment revealed a long N-terminal sequence that distinguished the *T. reesei* amino acid sequence from the other phytases. One interpretation of this is that the ORF of the mRNA is not as large as deduced using the software analysis. FIG. 3 shows an alternative ORF, which has a start codon downstream from the larger deduced ORF and encodes a protein which is more consistent in size to the other known fungal phytases (FIG. 5). The analysis suggests that the *T. reesei* phytase mRNA sequence has two potential translation start sites. It is possible that the mRNA encodes alternate forms of the protein.

Example 3

Preparation of Genomic DNA Encoding Phytases

Genomic DNA is prepared for *Trichoderma reesei* for the purpose of undertaking a PCR reaction to determine the sequences of the gene encoding phytase, including sequences 3☐ and 5☐ to the transcribed region, as well as sequences of any introns.

Genomic DNA is obtained from *Trichoderma reesei* (deposit no. ATCC 13631) and isolated according to standard methods. As the skilled artisan will recognize, probes for genomic nucleic acid sequences are readily obtained from any of the *T. reesei* phytase cDNA sequences disclosed in FIGS. 1-3. Such probes may be used, following the PCR methods described below, to obtain genomic sequences.

The following is an alternate method for obtaining genomic phytase sequences in *T. reesei*.

Alignments were performed for several known phytase sequences, including those from *Aspergillus Niger, Aspergillus ficum, Aspergillus terreus* 59, *Aspergillus terreus* 60, *Aspergillus fumigatus, Emericella nidulans, Talaromyces thermophylus* and *Myceliopthora thermophila*. From these, several "boxes" have been identified as being largely conserved, and from these primers are developed.

The following DNA primers have been constructed for use in amplification of phytase genes from the libraries constructed from the various microorganisms. All symbols used herein for protein and DNA sequences correspond to IUPAC IUB Biochemical Nomenclature Commission codes.

BOX1: primers coding for (V/L)L(A/S)RHGAR (SEQ ID NO: 19)

```
                              (SEQ ID NO: 20)
forward primer    BTIYTIKCIMGICAYGGIHCIMG (SEQ ID NO: 21)
forward primer    BTIYTIAGYMGICAYGGIHCIMG
```

BOX2: primers coding for NNTL(D/E/H) (SEQ ID NO: 22)

```
                              (SEQ ID NO: 23)
forward primer    AAYAAYACIYTISA (SEQ ID NO: 24)
reverse primer    TSIARIGTRTTRTT
```

BOX3: primers coding for LSPFC (SEQ ID NO: 25)

```
                              (SEQ ID NO: 26)
forward primer    YTTTCICCITTYTGY (SEQ ID NO: 27)
forward primer    YTIAGYCCITTYTGY (SEQ ID NO: 28)
reverse primer    RCARAAIGGIGAIAR (SEQ ID NO: 29)
reverse primer    RCARAAIGGRCTIAR
```

BOX4: primers coding for G(N/S)PLGP (SEQ ID NO: 30)

```
                              (SEQ ID NO: 31)
forward primer    GGIWVICCIYTIGGICC (SEQ ID NO: 32)
reverse primer    CCIARIGGIBWICC
```

BOX5: primers coding for DFSHD (SEQ ID NO: 33)

```
                              (SEQ ID NO: 34)
forward primer    GAYTTYTCICAYGAY (SEQ ID NO: 35)
forward primer    GAYTTYAGYCAYGAY (SEQ ID NO: 36)
reversed primer   RTCRTGIGARAARTC (SEQ ID NO: 37)
reversed primer   RTCRTGRCTRAARTC
```

BOX6: primers coding for VR(A/V)I(I/V)NDR (SEQ ID NO: 38)

```
                              (SEQ ID NO: 39)
*reverse primer   CKRTCRTTIAYIARIRCICKIAC
```

Boxes have also been developed according to the methods of Pasamontes et al. *Appl. Evir. Microbiol.* 63(5): 1696-1700

(1997) (expressly incorporated herein) to provide the following primers.

BOX2.5: coding for MDMCSFD (SEQ ID NO: 40)

```
                                         (SEQ ID NO: 41)
    forward primer      ATGGAYATGTGYTCNTTYGA
```

BOX4□: coding for YGHGAG (SEQ ID NO: 42)

```
                                         (SEQ ID NO: 43)
    reverse primer      TTRCCRGCRCCRTGNCCRTA
```

PCR is performed on a standard PCR machine such as the PTC-150 Mini Cycler from MJ Research Inc. (Watertown, Mass.), the Eppendorf Mastercycler (Hamburg, Germany) or the Hybaid Touchdown thermocycler (Middlesex, UK).

PCR conditions for Pwo polymerase (Boehringer Mannheim, Cat # 1644-947) comprise a 100 microliter solution made of 10 microliter of 10× reaction buffer (10× reaction buffer comprising 100 mM Tris HCl, pH 8-8.5; 250 mM KCl; 50 mM $(NH_4)_2SO_4$; 20 mM $MgSO_4$); 0.2 mM each of dATP, dTTP, dGTP, dCTP (final concentration), 1 microliter of 100 nanogram/microliter genomic DNA, 1 microliter of PWO at 1 unit per microliter, 500 mM primers (final concentration) and water to 100 microliters. The solution is overlaid with mineral oil.

Two approaches have been developed for amplification of phytase genes from the genomic DNA:

A) A first PCR is run using BOX1 and BOX6 primers; the products are run on an agarose gel and approximately 1 kb fragments are isolated and run in a second PCR using nested primers. For the second PCR run, best results have been obtained using primers from BOX1-BOX5 or from BOX5-BOX6 or BOX2.5/BOX4□.

Protocol A:
  PCR1:
    2□ at 94□C (1 cycle)
    45□ at 94□ C; 1□30□ at 40□C; 1□30□ at 72□C (30 cycles)
    7□ at 72□C (1 cycle)
    hold at 4□C Fragments are put on a 1% low melting gel and fragments around the expected size (0.0-1.2 kb) are sliced from the gel, isolated and used as a template for the second PCR run (PCR2). PCR 2 follows the same cycling protocol as PCR1.

B) Touchdown PCR is performed using BOX2.5/BOX40 primers. Using this technique, a specific fragment can be isolated, cloned into a TOPO vector (Invitrogen Corp., Carlsbad, Calif.), and sequenced without further processing.

Protocol B:
  3□ at 95□C (1 cycle)
  1□ at 95□C; 1□ at 60□C, decreasing to 50□C; 30□ at 72□C (20 cycles, so that the temperature drops 0.5□C each cycle in the annealing step)
  1□ at 95□C; 1□ at 50□C; 30□ at 72□C (10 cycles)
  hold at 4□C From the sequenced fragments, it is possible to use the RAGE technique (rapid amplification of genomic ends) to rapidly obtain the sequence of the full length gene. Using the GenomeWalker□ Kit from Clontech Laboratories, Inc (Palo Alto, Calif.) and manufacturer's protocol (GenomeWalker□ Kits User Manual, published Nov. 10, 1999, expressly incorporated herein), adapter ligations are derived from the fragment sequences to further determine upstream gene sequence. Sequences of phytase genes are determined from chromosomal DNA of various species.

Example 4

Cloning a Phytase Using Degenerate Primers

Degenerate primers are designed to clone a *Trichoderma* phytase from genomic DNA using PCR. Primers have been designed based upon regions of homology in previously known phytases.

The following degenerate primers have been designed:

```
                                         (SEQ ID NO: 44)
        225F            GAYTTYWSICAYGAYAA (SEQ ID NO: 45)
        226F            GCIGAYTTYWSICAYGA (SEQ ID NO: 46)
        227R            AYIACICKRTCRTTSAC (SEQ ID NO: 47)
        228R            AYIACICKRTCRTTWAC
```

Four primer pairs are used:
a) 225F+227R
b) 225F+228R
c) 226F+227R
d) 226F+228R

The PCR reaction mixtures are as follows:
Into 0.2 ml Ready-To-Go PCR Beads (Amersham Pharmacia Biotech, Inc., Piscataway, N.J.), place in the following order,
1 ul *Trichoderma* genomic DNA
1 ul forward primer (@50 picomoles/μl)
1 ul reverse primer (@50 picomoles/ul)
22 ul distilled water
50 ul mineral oil Amplification conditions are as follows using an Eppendorf Mastercycler (Hamburg, Germany)
step 1 95° C., 3'
step 2 94° C., 45'
step 3 40° C., 1'
step 4 72° C., 2'
step 5 go to step 2, repeat 40 times
step 6 72° C., 5'
step 7 hold at 5° C.

After amplification, 7.5 ul of each PCR reaction product is run on a 4% agarose gel. Attention is paid primarily to any bands running at approximately 250 nucleotides in size, consistent with the length expected from a new phytase gene. A preferred PCR reaction product is cloned into TOPO TA (Invitrogen Corporation, Carlsbad, Calif.) and DNA sequenced. The obtained sequence is translated and the amino acid sequence is deduced.

The deduced amino acid is analyzed for sequence homology to other fungal phytases to indicate it is a member of this family, as well as for sequence divergence to indicate novel properties.

To clone the rest of the *Trichoderma* phytase, phytase primers are designed based upon the discovered DNA sequence. Multiplex PCR is used to clone the remaining 5' upstream and 3' downstream portions of the gene (Weber, K. L., M. E. Bolander, et al., *Biotechniques* 25(3): 415-9 (1998), expressly incorporated herein). The skilled artisan will appreciate that other standard techniques known in the art could be used to clone the rest of the gene, including southern hybridization of a genomic library of *H. grisea*.

Example 5

Construction of a *Trichoderma* Chimera Phytase Expression Strain

A vector for expression of a *Trichoderma reesei* chimeric phytase is constructed and used to transform a phytase expression host such as *Aspergillus niger* or *Aspergillus nidulans*. The vector is designed to enable high level expression of a *Trichoderma* phytase without having to clone the mRNA or otherwise determine the start codon of the genomic clone of the phytase gene. The expressed phytase can then be used for characterization of the enzyme. Amino acids at the N-terminal end are coded for by the host *Aspergillus* phytase gene sequence. The remaining amino acids are coded for by a *Trichoderma* phytase gene sequence. Additionally, the signal sequence of the chimeric protein also is coded for by the host *Aspergillus* phytase.

The expression vector is constructed by combining two gene fragments: an N-terminal portion of the host *Aspergillus* DNA sequence with the DNA sequence from *Trichoderma*. PCR is used to amplify the two gene sequences to be combined into a single DNA segment, as further described below.

5A. Production of a Fusion Nucleic Acid

As an example, to amplify the *A. niger* sequence, primer 322F (below) and a primer which overlaps both the *A. niger* sequence and the *Trichoderma* sequence are used as forward and reverse primers, respectively. From this, fragment "A" is obtained. Primer 322F contains a BgI II restriction site conveniently at the 5' end for the purposes of cloning into the final expression vector. The primer which overlaps both the *A. niger* sequence and the *Trichoderma* sequence to allows for fusion of the two fragments by a second PCR reaction. Forward and reverse primers are constructed and used to amplify the *Trichoderma* sequence to obtain fragment "B". The reverse primer contains a restriction site, such as the Xba I site, for the purposes of cloning into the expression vector. The forward primer overlaps both the *A. niger* sequence and the *Trichoderma* sequence to allow for a subsequent fusion by a second PCR reaction.

Primer 322F (SEQ ID NO: 48)
CGGGAGATCTCAGCAATGGGCGTCTCTGCTGTTCTAC

PCR Amplification of A and B Fragments

The PCR reaction mixtures are as follows:
Into 0.5 ml Hot Start 100 tubes (Molecular Bio-Products, Inc., San Diego, Calif.) place, in the following order,
1 ul forward primer (@50 picomoles/ul)
1 ul reverse primer (@50 picomoles/ul)
2 ul nucleotide mix (Boehringer Mannheim)
5 ul 10×Pwo PCR Buffer (Boehringer Mannheim)
41 ul distilled water
heated at 95° C. for 90", placed onto ice for 5'
5 ul 10×Pwo PCR Buffer
44 ul distilled water
1 ul *Aspergillus niger* or *Fusarium* genomic DNA (@ 0.5 ug/ul DNA)
0.75 ul Pwo DNA Polymerase (Boehringer Mannheim, 5 U/ul)

Amplification conditions are as follows using a PTC-150 Mini Cycler (MJ Research, Watertown, Mass.):
step 1 95° C., 2'
step 2 94° C., 30"
step 3 60° C., 40'
step 4 72° C., 3'
step 5 GOTO step 2, 34 times
step 6 72° C., 10'
step 7 hold at 4° C.

Fragments A and B are electrophoresed through agarose, bands of the appropriate size are cut out and the DNA recovered from the agarose using Qiaquick Gel Extraction Kit (Qiagen, Inc., Valencia, Calif.).

Fusion PCR to Combine the *Aspergillus* N-Terminus (Fragment A) with the *Trichoderma* Gene (Fragment B)

The PCR reaction mixtures are as follows:
Into 0.5 ml Hot Start 100 tubes (Molecular Bio-Products, Inc., San Diego, Calif.) place, in the following order,
1 ul forward primer 332F (@50 picomoles/ul)
1 ul reverse primer 335R (@50 picomoles/ul)
2 ul nucleotide mix (Boehringer Mannheim)
5 ul 10×Pwo PCR Buffer (Boehringer Mannheim)
41 ul distilled water
heat at 95° C. for 90", place onto ice for 5'
5 ul 10×Pwo PCR Buffer
44 ul distilled water
0.5 ul recovered fragment A (@ 0.25 ug/ul DNA)
0.5 ul recovered fragment B (@ 0.75 ug/ul DNA)
0.75 ul Pwo DNA Polymerase (Boehringer Mannheim, 5 U/ul)

Amplification conditions are as follows using a PTC-150 Mini Cycler (MJ Research, Watertown, Mass.):
step 1 95° C., 2'
step 2 94° C., 30"
step 3 60° C., 40"
step 4 72° C., 3'
step 5 go to step 2, repeat 30 times
step 6 72° C., 10'
step 7 hold at 4° C.

The resulting fusion PCR amplification product is electrophoresed through agarose, the appropriate sized band is cut out and the DNA recovered from the agarose using Qiaquick Gel Extraction Kit (Qiagen, Inc., Valencia, Calif.).

5B. Production of an Expression Vector for *Aspergillus niger*

The recovered fusion fragment is digested with BgI II and Xba I, and inserted into the appropriate *Aspergillus* vector, such as pGAPT-PG for *Aspergillus niger*, which has also been digested with the same enzymes.

The following elements are present in the final expression vector. In brief these elements are: the phytase chimera gene, the *A. awamori* glucoamylase (glaA) promoter, the *A. niger* glaA terminator and the *A. nidulans* pyrG gene which is used as a selectable marker for transformation. The pyrG gene may be PCR amplified from *Aspergillus nidulans* strain FGSC4 obtainable from the Fungal Genetics Stock Center, Department of Microbiology, University of Kansas Medical Center, Kansas City, Kans. 66160-7420 USA. The *A. awamori* glaA promoter and the *A. niger* terminator DNA sequences may be obtained from the GenBank sequence database. The *A. nidulans* pyrG sequence is disclosed in B. R. Oakley, J. E. Rinehart, et al., *Gene* (1987) 61(3): 385-99. The elements are arranged in the *E. coli* plasmid pGAPT-PG in such a way that the strong glucoamylase promoter to drive expression of the chimeric phytase gene product. This vector is used to transform an *Aspergillus* expression strain from which active chimeric phytase is recovered.

5C. Expression of Chymeric Phytase

Production of phytase is achieved through transformation of the phytase expression vectors into a host *A. niger* strain. Transformation of *Aspergillus* is known in the art and is described for example in B. Oakley et al., *Gene,* 61 (1987) pp. 385-399. The transformed *A. niger* strains were grown in shake flask culture as described in Dunn-Coleman et al. (1991) *Biotechnology (NY)* 9(10): 976B-1.

Example 6

Evidence of Phytate Hydrolyzing Activity in Liquid Culture

A selected fungal species is grown in defined media containing various concentrations of inorganic phosphate, and growth characteristics and phytase production are assayed and compared. Spore suspensions are used ($2\times10^6$ spores/ml final con) to inoculate a minimal media (Vogels) where the phosphate concentration is altered to see how this will affect growth and phytase production. Cultures are grown in 50 ml of medium in shake flask culture at 25° C. to 30° C. Cultures are harvested at 24, 48, 72 and 96 hours. Culture supernatants are assayed for phytase activity using the method of Fiske and SubbaRow, *Journal of Biological Chemistry* 66:375-392 (1925). Growth may be determined by dry weight or OD readings.

6A. Effect of Different Media Conditions on Growth and Morphology

A series of fungal growth curves are produced to look at the effect of available P In the medium on growth and phytase production. In some instances, when the P level is reduced, morphological changes in the growth of the fungus are observed which are associated with a stressed condition (e.g., mycelial fragmentation, pelleting, heterogeneous growth and an overall appearance of a pale yellow color). This physiological strain may be related to the appearance of phytase activity at a point in the growth curve, for example approaching late exponential phase. Morphological evidence of phytic acid utilization may be observed in cultures of low P (e.g., 0.57 mM) supplemented after 24 hours growth with 1 mM phytate as a phosphorus source. The morphological changes seen without added phytate may not be apparent, indeed the supplement samples may resemble cultures in media of higher P which were not limiting. This response would indicate that a phytic acid specific hydrolyzing activity was being produced so that P could be supplied to the growing fungus. As a caveat, it is possible that higher concentrations of phytate (e.g., 5 mM) supplementing the cultures result in a lack of cell growth. Such a result would suggest that the high level of phytate in the medium chelates essential minerals resulting in a medium that cannot support fungal growth and nutrition.

In an exemplary study, the fungus is grown in media containing

High phosphate (1.14 mM)

Low phosphate (0.57 mM)

Low phosphate plus 1 mM supplemented phytate.

Growth is monitored over 0, 24, 48, 72 and 96 hours by dry weight measurements, and the morphological characteristics in response to the different media conditions are also observed. In a situation where phytate hydrolysing activity which allows the fungus to access phosphate from phytate, and so circumvent phosphate starvation stresses that the culture may otherwise experience, the major observations that would be expected are:

1. Good growth in high phosphate, consistent fungal morphology indicative of healthy culture.
2. Markedly poorer growth in low phosphate condition, fungal morphology heterogenous with evidence of clumping and mycelial fragmentation. The culture may have a sickly yellow appearance.
3. Similar cultures as for (2), when supplemented with phytate (the substrate), no longer appear to be under the same physiological stress. Biomass growth is similar to condition (1) and the fungal morphology is the same as for the high phosphate condition.
4. Growth curves and photographic evidence support these observations.

6B. Phytase Activity in Culture Supernatants

Phytase activity in the supernatants of fungi growing on media with variable levels of inorganic P can be measured. Supernatant samples are used to compare activities at a specified time post inoculation. Phytase activity may be expressed as the number of mmoles P released per minute per ml culture supernatant. Sample activities are calculated from triplicate culture flasks where supernatants are assayed for phytase in duplicate. Activities are shown as mean_SD. Along with the observations above, a clear physiological stress associated with cultures where phosphate is limited, which adversely affected growth, may be observed and linked to the appearance of phytase activity.

6C. Concentration of Culture Supernatants

Additional evidence of phytase activity can be expected from concentrated supernatant (concentrated protein). For example, concentrated protein samples can be obtained from:
1. Cultures of fungus from conditions of stress and low phosphate (where phytase is expected to be expressed),
2. Cultures of fungus of high phosphate and no stress, where phytase is not expected to be produced, and
3. Cultures supplemented with low phosphate and supplemental phytate.

Silver stained SDS-PAGE gels of these concentrated protein samples are expected to show a protein profile demonstrating the appearance of a protein band (putative phytase band) in concentrated protein from condition 1 (above) which is not present in condition 2. A similar appearance of this band is also expected in condition 3, albeit at a lower level. Based on the amino acid sequence of a specific phytase, and on whether it appears to be an extracellular enzyme, the size of the protein may be approximated. It should be noted, however, that glycosylation modification on the extracellular enzyme may increase the MW.

Example 7

PCR amplification of Phytase Gene Fragments

7A. Degenerate Primer Design

Based on alignments of published phytase amino acid sequences, a range of degenerate primers are designed against conserved structural and catalytic regions. Such regions included those that are highly conserved among the phytases, as well as those known to be important for enzyme structure and function.

For example, amino acid sequences for published phytases are aligned. It should be noted that many phytase sequences are publicly available from GenBank, and each is incorporated herein by reference.

Particular regions are chosen to meet the criteria above, and a range of forward and reverse primers designed from the amino acid sequences. Using the genetic code for codon usage, degenerate nucleotide PCR primers are synthesized.

As another example, primers are designed from the published amino acid sequence for different phytases from a single species (e.g., *A. niger*). These primers may be designed as follows:
1. Primer 1: Forward (5'-3') primer from, for example, the phosphate binding domain of a phytase, which should be essential for catalytic activity.
2. Primer 2: Reverse primer from a central phytase region which seems to be conserved relatively well.

All primers may be synthesized in the 5'-3' direction. The standard genetic code is used to change from amino acid to triplet codon, and standard IUB code for mixed base sites are used (e.g. to designate I for A/C/T/G).

As can be seen from the alignment of sequences for *A. niger* PhyA and PhyB, the phosphate-binding domain is well conserved with only a single amino acid difference between PhyA (RHG<u>A</u>RYP; van Hartingsveldt et al., 1993) and PhyB (RHG<u>E</u>RYP; Piddington et al., 1993). A degenerate primer may be designed complementary to this region in the PhyA version of the sequence only, i.e. using RHGARYPT as the basis for primer design. This would be to bias the primer towards a PhyA type phosphate binding domain. A second conserved region, which may serve as the basis for primer 2 for *A. niger*-derived primers, occurs in the middle of the PhyA and PhyB amino acid sequence. This conserved central phytase-specific domain in PhyA (FTHDEWI)-corresponds to amino acids 285-291. In PhyB, the amino acid sequence (FTQDEWV) corresponds to amino acids 280-286.

Degenerate primers developed as described above may be used to amplify a phytase encoding region from other species by PCR, as described next.

7B. PCR Amplification of Phytase Gene Fragments

Genomic DNA from a species of interest may be used as a template for PCR amplification of putative phytase gene fragments using combinations of primers made as described above. PCR is carried out using the PCR Ready-to-go Beads from Amersham Pharmacia. Conditions are determined by individual experiments, but typically thirty cycles are run in a Techne thermal cycler. Successful amplification is verified by electrophoresis of the PCR reaction on a 1% agarose gel. A PCR phytase product that is amplified by the primers may be anticipated by a correct expected size. The product is then purified by gel extraction using the Qiaquick Spin Gel Extraction kit from Qiagen. The purified PCR product is ligated into the commercial pGEM-T Easy vector System (Promega Corporation) to facilitate cloning. Ligation reactions are incubated at 4° C. overnight in a total volume of 10 ml containing 0.1 volumes of 10× ligase buffer and 1 ml (1 U·ml$^{-1}$) of T4 DNA ligase. Typically insert DNA is used in the reaction in a 1-4:1 molar ratio of insert to vector DNA. A 100 ml aliquot of CaCl$_2$ competent *E. coli* XL-1 Blue cells are removed from −80° C. storage and thawed on ice for transformation. 3 ml of ligation mix is added to the cells and the mixture incubated on ice for 20 min. The cells are then heat shocked at 42□C for 1 min. and returned to ice for 5 min. The transformation mixture is added to 0.9 mL of L-broth, and the cells incubated with shaking and without selection to allow expression of the ampicillin resistance gene product before selection is applied (37_C, 1 h). Aliquots of 200, 300 and 400 ml of this culture are then spread directly on selective agar plates.

Plates are incubated at 37□C overnight. Colonies containing recombinant plasmids are visualized using blue/white selection. For rapid screening of recombinant transformants, plasmid DNA is prepared from cultures of putative positive (white) colonies. DNA is isolated by the method of Birnboim and Doly following the protocol in Sambrook et al (1989). The presence of the correct insert (650 bp) in the recombinant plasmid is confirmed by restriction analysis. DNA is digested with restriction enzymes (e.g., Not1-pPst1) overnight at 37° C., and digest products visualized by agarose gel electrophoresis. A number of clones may contain the correct sized insert and can be selected for manual sequencing to see if the insert is a phytase gene fragment. Inserts are sequenced using the dideoxy chain termination method of Sanger et al (1977) with a modified form of T7 DNA polymerase (Sequenase version 2.0). The reactions are carried out using reagents supplied in the Sequenase version 2.0 kit (Amersham Life Science-United States Biochemical Corporation), following the manufacturer's protocol. Partial sequence from the ends clones may indicate that a phytase gene fragment had been cloned. Full sequencing of the double-stranded inserts is performed on plasmid DNA from these clones.

7C. Sequence Analysis

The sequences are analyzed by BLAST and protein translation sequence tools. BLAST comparison at the nucleotide level may show various levels of homology to published phytase sequences. Initially, nucleotide sequences are submitted to BLAST (Basic BLAST version 2.0) by accessing the BLAST database on the world wide web. The web site used is at ncbi.nlm.nih.gov/cgi-bin/BLAST. The program chosen is blastn, and the database chosen is nr. Standard/default parameter values are employed. Sequence data for putative gene fragments are entered as sequence in FASTA format and the query submitted to BLAST to compare these sequences to those already in the database.

The sequences are then subjected to a DNA-to-protein translation tool called Protein machine. This tool is also available on the web at medkem.gu.se/edu/translat.html. Another suitable translation tool is known as Translation Machine, available on the web at www2.ebi.ac.uk/translate/. The DNA sequences of putative phytase gene fragments are inserted into the analysis block, and the standard genetic code is used as the basis for the translation. Translations are carried out in all three frames and on forward and reverse strands. The translated amino acid sequence is delivered on the screen by the analysis tool as amino acid sequence in one letter code. Ideally, analysis of the amino acid sequence will show that the fragment contains both correct ends (as used to design the primers), contains the essential P binding motif and perhaps other residues which are also present in published phytase sequences. From this, it may be concluded that the fragment cloned is a phytase gene fragment.

Sequence alignments and analysis of those alignments is carried out at the nucleotide and amino acid level using the ALIGN program (Alignment Editor Version 4/97; Dominick Hepperle, Fontanestr. 9c, D016775, Neuglobsow, Germany). In performing the analysis, subject sequences are pasted in, and the PHYLIP Interleaved format employed. The homology analysis is carried out using the "Analyze" section of the program, and specifically the option entitled "Distance Analysis." This calculates % homologies and the number of different sites between species, using a minimum of two amino acid sequences (i.e., two "species"). Minimal and maximal homologies are calculated as %. The basis for homology analysis is done as % identity, on the calculation of "number of identical amino acids (or bases) divided by the total number of amino acids (or bases) multiplied by 100" to give a percentage value. Amino acid sequences are placed into the ALIGN program along with published phytase sequences and a manual alignment at the amino acid level is carried out. From this, the deduced translation for the PCR product obtained using degenerate primers may be obtained.

Example 8

Southern Analysis for Library Production

Genomic DNA from different species is digested with a range of restriction enzymes overnight at 37° C. Successfully digested DNA is run out on a 1% agarose gel in preparation for transfer to the nylon membrane. After completion of electrophoresis, the agarose gel is soaked for 10 min. in 0.2M HCl to depurinate the DNA and then rinsed briefly in ddH$_2$O. The DNA is transferred to the Hybond☐-N+ membrane (Amersham International PLC) by alkali capillary blotting. The blot is set up so that the nylon filter is sandwiched between the gel and a stack of absorbent paper towels. A wick of Whatman 3MM paper (Schleicher and Schuell, Dassel, Germany) is prepared on a glass plate over a reservoir of transfer buffer (0.4M NaOH). The gel is inverted on the wick, taking care to avoid the formation of air bubbles, and surrounded by strips of Nescofilm to prevent the blotting action of the paper towels from by-passing the gel at its edges. The gel is covered with an equal sized piece of Hybond☐-N+ membrane which had been cut in the corner to match the gel and pre-wetted in 3×SSC. Next, 3-5 pieces of 3MM paper are placed on top of the filter and the blot completed by adding a 10 cm stack of blotting paper followed by a 0.5 kg weight. The blot is left for 8-24 h to transfer the DNA. The membrane is then washed briefly in 2×SSC at RT and baked in a vacuum oven at 80° C. to fix the DNA to the membrane. An isolated fragment from the procedures above is used to probe the Southern blot. It is firstly labelled with $^{32}$P isotope by use of the High Prime DNA Labelling Kit (Boehringer Mannheim). Denatured fragment is added into a random primed labelling reaction which incorporates radio-labelled adenine. The Southern blot is pre-hybridised for 1 hour at 42° C. in 12 mL of Easy-Hyb buffer (Boehringer Mannheim) in a hybridisation tube. Radiolabelled probe is denatured and added to 5 mL of Easy-Hyb hybridisation buffer and left to hybridise overnight at 42° C. Following hybridisation, the blot is washed by incubation in 40 mL 3×SSC, 0.1% SDS for 15 min at 42° C. This low stringency wash is repeated with fresh wash solution. After stringency washing, the lot is rinsed in 3×SSC, sealed in clear plastic and exposed to x-ray film. This is left for 2 hours and the film developed.

Strong hybridizing bands may be observed for a given species digest. Such results indicate that the fragment can be used as a probe for library screening.

Example 9

Isolation of a Polynucleotide Sequence from the Genome of a Species of Interest Encoding a Phytase 9A. Genomic Library Generation and Screening Following the Southern hybridization analysis, a partial genomic library may be made in order to clone a full-length phytase gene. A size restricted plasmid library targeting a digestion fragment (as estimated from Southern analysis) is generated. Digested genomic DNA is run out on a 1.25% agarose gel. The digested fragments of a preferred approximate size are extracted from the gel, and purified by Glass-Max (Gibco-BRL, Scotland). Purified genomic fragments are used in a shotgun ligation reaction with restriction nuclease linearized pSK II Bluescript vector (Stratagene). The vector is first dephosphorylated before ligation, and the ligation reaction is carried out at 14° C. overnight. The library is produced by transformation of E. coli XL-10 Gold ultracompetent cells (Stratagene). 100 ml aliquots of cells are removed from −80° C. storage and thawed on ice for transformation. 4 mL of b-mercaptoethanol is added to the cells on ice. 3 ml of ligation mix is added to the mixture and the mixture incubated on ice for 20 min. The cells are then heat shocked at 42☐C for 30 sec and returned to ice for 2 min. The transformation mixture is added to 0.9 mL of NZY-broth, and the cells incubated with shaking and without selection to allow expression of the ampicillin resistance gene. The transformed cells are plated out on blue/white selection LB-agar plates, and left to incubate overnight at 37° C. The colonies are lifted onto nitrocellulose filters by the method of Maniatis (10% SDS—lysis, 3 min; 1.5M NaOH-denaturation, 5 min; 1.5M TricHCl—neutralisation, 5 min; 3×SSC—rinse, 5 min). The filters are then baked for 2 hours at 80° C. under vacuum to fix the DNA. The library is screened with $^{32}$P radiolabelled 636 bp probe in the same manner as for Southern hybridisation. After hybridisation the filters are washed twice in 3×SSC, 0.1% SDS, 42° C., 15 min. The filters are then rinsed in 3×SSC, sealed in plastic and exposed to X-ray film overnight at −80° C. Positive hybridizing spots are identified on the film. These are aligned to the agar plates containing the transformants. The hybridising spots may match up to more than one single colony on the agar plates. All colonies in the radius of the hybridizing spot are picked up using sterile loops and used to inoculate 2 mL of Luria broth. The cultures are grown at 37° C. for 2 hours. Dilutions of the cultures are made from $10^{-1}$ to $10^{-5}$ and 100 mL of each sample is plated out on LB-amp agar plates and incubated overnight at 37° C. The plates which have between 10 and 150 colonies on them are chosen to go forward for a secondary screen. Colony lifts are done as before, and filters are processed using the same procedures. Fresh $^{32}$P labelled probe is prepared, and the filters screened in the same way as outlined previously. Stringency washes are carried out using 2×SSC, 0.1% SDS at 42° C. for 15 min. Filters are then rinsed in 2×SSC, sealed in plastic and exposed to X-ray film for 2 hours. The developed film should show hybridizing spots, consistent with amplification of the positive colonies from the primary screen. The film is then aligned to the plates, and the spots coordinated to see if they corresponded to single isolated colonies. The best positives that match up to single colonies are picked and used to inoculate Luria broth for plasmid DNA preparations. Plasmid DNA is purified by Qiaspin Mini-Prep kit (Qiagen) and restriction analysis carried out to estimate the size of the inserts. Clones that give the same restriction profile can be used to suggest an insert size. Clones may be partially sequenced to determine if they are the correct gene/gene fragment. The full sequence of these clones are then determined.

9B. Percentage Identity Comparison Between Fungal Phytases

The deduced polypeptide product of the cloned phytase gene fragment is used for homology analysis with published phytases. The analysis shows percent identities and, together with analysis of the translated sequence, may provided evidence that the gene fragment cloned is a homolog of a specific phytase.

9C. Generation and Screening of SalI-Based Size-Restricted Genomic Library to Isolate Remainder of Phytase Gene In order to isolate the remaining portion of a gene, a second restriction enzyme may be used to generate a second partial genomic library, and fragments may then be subcloned together. The restriction endonuclease recognition sites present within a cloned phytase sequence are identified using Webcutter. Of particular interest are sites for enzymes that are used in the Southern analysis discussed above. Very large fragments (e.g., 8 Kb), would be difficult to clone in a plasmid-based library a low degree of hybridisation with a specific restriction enzyme band argues against use of such in a library screen, and the presence of two bands in a restriction enzyme lane is likely to complicate the screening process. The library is made as before in pBluescript SKII, and screened using the same probe. A selection of positive hybridising colonies are chosen and aligned to colonies on the plates. Matching colonies are picked for plasmid DNA preparations. Restriction analysis may show how many clones have inserts. These clones are then fully sequenced.

9D. Amplification of Contiguous Phytase Gene for Heterologous Expression

A composite phytase sequence is produced from genomic clones and used to design a number of upstream and downstream primers which could be used to amplify a contiguous phytase gene sequence. PCR amplification is also designed to facilitate cloning and expression of the complete phytase gene in to a heterologous expression vector (e.g., pGAPT-PG, a 5.1 Kb construct provided by Genencor International, Inc.). Restriction enzyme sites within the multiple cloning site of the vector which are not present within the phytase gene sequence are determined. A number of 5' and 3' flanking primers may be designed using the phytase gene sequence, and modified to include the restriction enzyme recognition sites for these enzymes.

Restriction enzyme recognition sites are designed into the primer sequences to facilitate cloning into the expression vector. The upstream and downstream flanking regions used to design the primers are arbitrarily chosen at approximately 100 bp upstream from the ATG (start) codon and downstream from the TAG (stop) codon respectively. The gene sequence used is also chosen to contain as equal balance of bases as possible.

Amplification of the phytase gene by PCR may be done using genomic DNA combinations of primers. PCR should amplify a region corresponding to the full-length phytase gene. The desired product produced by amplification with the primers is cloned into a vector and several clones which contain the correct size of insert are selected for sequencing. Homology analysis of the clone sequences is then performed and a full length phytase sequence determined.

PCR amplification genomic DNA is carried out using a combination of 5' primers and 3' primers, and using a high fidelity DNA polymerase, Pfu, to minimise error for expression of the phytase gene. This polymerase is Pfu DNA polymerase (Stratagene) and comes as part of the Pfu DNA polymerase kit for PCR. For these reactions, reaction buffer, dNTPs, target DNA and primers are mixed together, and 2.5 units of Pfu polymerase added in a final reaction volume of 50_L. After amplification, a 5_L aliquot of the reaction mixture is analysed by gel electrophoresis. Selected fragments are cloned directly into the vector pCR-Blunt II TOPO (Invitrogen), and a select number of clones analysed to confirm the presence of the correct insert. (Blunt-ended PCR products that are generated by Pfu DNA polymerase are cloned into the Zero Blunt_TOPO_PCR cloning kit (Invitrogen). This vector contains a MCS site and a kanamycin gene for anitbiotic resisistance, but also allows selection based on disruption of the lethal *E. coli* gene ccdb, as opposed to blue-white selection. Purified PCR product (50-200 ng) is added to 1_L of pCR-BluntII-TOPO vector and the reaction volume made up to 5_L with sterile water. This is mixed gently at left to incubate for 5 min at room temperature. 1_L of 6×TOPO Cloning Stop Solution is added, and the reaction left on ice or frozen at −20° C. for up to 24 hours for transformation.) The integrity of the engineered restriction sites are also confirmed by this analysis. A number of clones are prepared and sequenced. Sequence analysis may confirm the presence of a full-length phytase gene. This gene may then be taken forward for expression in a heterologous system, and subsequent biochemical characterisation of the enzyme.

9E. Analysis of Phytase Sequence

An alignment is made of the isolated sequence and published phytases and homology analysis done, on a % identity basis.

Example 10

Cloning, Expression and Characterization of the Phytase

Over-expression of the phytase gene in a heterologous host may be done to produce enough protein to carry out characterization of the enzyme.

10A. Cloning of Phytase Gene into Expression Vector and Transformation in to a Host The full-length phytase gene is amplified with a high-fidelity DNA polymerase, is produced using primers that engineered to contain two restriction enzyme sites (e.g., EcoRV and AgeI). These sites are used to facilitate cloning into the expression vector (e.g., pGAPT-PG). The phytase clones are digested with the enzymes to produce a single insert fragment. The vector is also digested with these enzymes and linearised. The phytase gene fragment is ligated to the expression vector, and a number of transformants produced. A selection of these clones is analyzed to confirm the presence of the insert. The phytase clones are then used to transform swollen spores of *A. nidulans* by electroporation.

The transformation of host such as *A. niger* strain FGSC A767 and *A. nidulans* FGSC A1032 by electroporation is adapted from the protocol of O. Sanchez and J. Aguirre developed for *A. nidulans*. 50 mL of YG medium (0.5% yeast extract, 2% glucose, supplemented with 10 mM uridine and 10 mM uracil) is inoculated at $10^7$ spores/mL with appropriate spore suspension. The cultures are grown for 4 hr at 25□C at 300 rpm on rotary shaker. Swollen spores are collected by centrifugation at 4000 rpm for 5 min at 4□C. Spores are resuspended in 200 mL ice-cold sterile water and centrifuged at 4000 rpm for 5 min at 4□C. The supernatant is poured off and the spores are resuspended in 12.5 ml YED media pH 8.0 (1% yeast extract, 1% glucose, 20 mM HEPES) and incubated for 60 min at 30° C. at 100 rpm on rotary shaker. The spores are collected by centrifugation at 400 rpm for 5 min, then resuspended in 1 mL of ice-cold EB buffer (10 mM tris-HCl, pH 7.5, 270 mM sucrose, 1 mM Lithium acetate) at a concentration of $10^9$ conidia.mL$^{-1}$ and kept on ice. 50_L of the swollen spore suspension is mixed with 1 to 2 µg DNA in a total volume of 60 µl in sterile eppendorfs and kept on ice for 15 min. The suspension is transferred to 0.2 cm electroporation cuvette. Electroporation is carried out in a BioRad electroporation device (settings 1 kV, 400 W, 25 µF). 1 mL of ice-cold YED is added to the suspension after electroporation, and the combined mix is transfered to a pre-chilled sterile 15 mL Falcon tube and kept on ice for 15 min. This is then incubate at 30□C for 90 min at 100 rpm on rotary shaker, with the tubes in a horizontal position. The spores are plated out and transformants are observed after 36-48 hours.

Circular plasmid DNA may be used. *A. niger* strain FGSC A767 and *A. nidulans* strain FGSC A1032 can be obtained from the Fungal Genetics Stock Center, University of Kansas Medical Center, 3901 Rainbow Boulevard, Kansas City, Kans., USA.

10B. Preliminary Characterisation of Transformants

Transformants are selected for further analysis. Spores from each of these transformants are used to inoculate selective media, and spore supensions of each clone are made. These are used to inoculate liquid cultures of the transformants which are screened for phytase activity. Cultures are grown over 72 hours, and the supernatants collected. Samples are desalted in PD-10 columns, and the protein samples eluted in 0.25 M sodium acetate. Phytase assays are carried out in the standard conditions (pH 5.5, 37° C. for 30 min). Clones are identified having phytase activity. These are taken forward for further analysis.

10C. Time of Maximal Expression of Phytase in Liquid Culture

In order to assess when the level of phytase production is at its highest for subsequent biochemical characterisation, a series of liquid cultures of clones are generated over a 2-day to 7-day period. Cultures are inoculated with spore suspension of the appropriate transformants, and harvested at each day over this period. Culture supernatants are processed as standard, and the desalted culture supernatant is assayed under standard phytase conditions. The time point of highest phytase activity is then determined.

Liquid cultures are harvested at each time point, desalted and eluted in 0.25 mM sodium acetate pH 5.5. Phytase assays are carried out under standard conditions (pH 5.5, 37° C., 30 min) in duplicate. Activity is expressed in phytase units per mL of culture supernatant (μmoles of Pi released min-1 mL-1).

Untransformed host may also be assayed across these timepoints as a control. Protein samples from selected supernatant samples (day 4 and day 6), both before and after desalting are analyzed by SDS-PAGE to determine levels of secretion.

10D. Southern Analysis of Transformants

Although there may be evidence that the phytase gene has been successfully cloned into the expression vector, and that expression of an active enzyme had been achieved, molecular evidence may also be obtained. Genomic DNA preparations are made from the transformed host, and from the original untransformed host. The DNA is digested with a restriction enzyme, preferably one where there is no internal site within the phytase gene, and Southern hybridisation analysis of the transformants is carried out. The Southern blots are analysed with a phytase probe from species under investigation. Single strong hybridising bands seen for the transformants under conditions of medium to high stringency (3×SSC) indicate successful cloning. If there is no evidence of any other hybridising bands, it can be concluded that a single-copy of the phytase gene is present in the transformed host. A lack of hybridising bands in the untransformed sample indicates that there is no homology between the phytase of interest and any phytases present in the host genome.

10E. Biochemical Characterisation of a Phytase

To prove that the cloned gene represents a specific phytase activity, and to characterise that activity, a range of biochemical analyses are carried out on the over-expressed enzyme. Preliminary characterisation may indicate that the gene is producing a phytic-acid hydrolysing activity. This analysis can be extended to examine activity at different pHs, temperatures and against different substrates.

Transformant are taken forward for these analyses, and cultures are harvested at optimum expression time, as determined above. With phytic acid as the substrate, the pH effect on enzyme activity can be shown. The purified enzyme sample is desalted from culture supernatant, and eluted in 0.025 mM sodium acetate pH 5.0. This is then added to substrate which is made in solutions of the following buffers: pH 3.0: 0.4M glycine-HCl, pH 4.0: 0.4M Sodium acetate, pH 5.0: 0.4M Sodium acetate, pH 6.0: 0.4M imidazole-HCl, pH 7.0: 0.4M Tris-HCl, pH 8.0: 0.4M Tris-HCl pH 9.0: 0.4M Tris-HCl. An optimum pH for the phytase activity may be determined, as well. Little activity seen when 4-nitrophenyl-phosphate is used as the substrate indicates a high level of specificity for the phytic-acid substrate.

The temperature profile of the enzyme is characterised using pH 5.0 buffer, over a range of temperatures, using phytic acid as the substrate. The phytase temperature activity range and ooptimum activity temperature can be determined.

Preliminary stability studies may also be carried out on the phytase. Samples of the protein are left at −20° C., 4° C., and 37° C. overnight, and then assayed under standard conditions. Samples may also be exposed to high temperature (e.g., 85° C. for 20 minutes, and 100° C. for 10 minutes) to determine the thermostability of the phytase activity. Residual activity is based on comparison to phytase activity determinations taken from the samples before exposure to each condition. Samples may be assayed afterwards in the same assay conditions.

Of course, it should be understood that a wide range of changes and modifications can be made to the preferred embodiment described above. It is therefore intended that the foregoing detailed description be understood in the context of the following claims, including all equivalents, which are intended to define the scope of this invention.

The invention claimed is:

1. A method of producing an enzyme having phytase activity, comprising:
   (a) providing a host cell transformed with an expression vector comprising a polynucleotide which codes for a enzyme having phytase activity having the amino acid sequence with at least 90% sequence identity over the entire length of SEQ ID NO:5, wherein the phosphate binding region has a sequence (V/L)L(A/S)RHGAR;
   (b) culturing said transformed host cell under culture conditions for production of said enzyme; and
   (c) recovering said enzyme wherein said phytase hydrolyzes phytate to inositol in a phytase assay.

2. The method of claim 1, wherein said host cell is an *Aspergillus* species.

3. The method of claim 1, wherein said host cell is a *Trichoderma* species.

4. A purified enzyme having phytase activity, produced by the method of claim 1, said enzyme having an amino acid sequence with at least 90% sequence identity to SEQ ID NO:5, wherein the phosphate binding region has a sequence (V/L)L(A/S)RHGAR.

5. The method according to claim 1, wherein the polynucleotide codes for an enzyme having phytase activity having at least 95% sequence identity to SEQ ID NO:5.

6. The method according to claim 1, wherein the polynucleotide has at least 85% sequence identity to the nucleotide sequence disclosed in SEQ ID NOS: 1, 2 or 3.

7. An enzyme composition comprising the purified enzyme of claim 4.

8. The method of claim 2, wherein the *Aspergillus* species is *A. niger*.

9. The method of claim 3, wherein the *Trichoderma* species is *T. reesei*.

10. The method according to claim 5, wherein the polynucleotide codes for an enzyme comprising SEQ ID NO:5.

11. An enzyme composition comprising the recovered enzyme of claim 1.

12. The method of claim 1, wherein at least one of the domains selected from the group consisting of: Box 2, Box 4, box 5, and Box 6 in SEQ ID NO:5 is conserved.

* * * * *